United States Patent
Grimm et al.

(10) Patent No.: US 12,162,952 B2
(45) Date of Patent: Dec. 10, 2024

(54) HUMAN-DERIVED ANTI-(POLY-GA) DIPEPTIDE REPEAT (DPR) ANTIBODY

(71) Applicants: Biogen MA Inc., Cambridge, MA (US); Neurimmune AG, Schlieren (CH)

(72) Inventors: Jan Grimm, Dübendorf (CH); Fabio Montrasio, Schindellegi (CH); Isin Dalkilic-Liddle, Watertown, MA (US); Mia Marie Rushe, Everett, MA (US); Joseph Walter Arndt, Swampscott, MA (US)

(73) Assignees: Neurimmune AG, Schlieren (CH); Biogen MA Inc., Cambridge, MA (US)

( * ) Notice: Subject to any disclaimer, the term of this patent is extended or adjusted under 35 U.S.C. 154(b) by 783 days.

(21) Appl. No.: 17/050,353

(22) PCT Filed: Apr. 25, 2019

(86) PCT No.: PCT/US2019/029109
§ 371 (c)(1),
(2) Date: Oct. 23, 2020

(87) PCT Pub. No.: WO2019/210054
PCT Pub. Date: Oct. 31, 2019

(65) Prior Publication Data
US 2022/0153874 A1    May 19, 2022

Related U.S. Application Data

(60) Provisional application No. 62/772,809, filed on Nov. 29, 2018.

(30) Foreign Application Priority Data

Apr. 27, 2018 (EP) ..................... 18169888

(51) Int. Cl.
| | | |
|---|---|---|
| C07K 16/00 | (2006.01) | |
| A61K 47/68 | (2017.01) | |
| A61K 49/00 | (2006.01) | |
| A61K 51/10 | (2006.01) | |
| C07K 16/44 | (2006.01) | |
| G01N 33/53 | (2006.01) | |

(52) U.S. Cl.
CPC .......... C07K 16/44 (2013.01); A61K 47/6835 (2017.08); A61K 49/0002 (2013.01); A61K 51/10 (2013.01); C07K 2317/24 (2013.01); C07K 2317/56 (2013.01); C07K 2317/565 (2013.01)

(58) Field of Classification Search
CPC ................. A61P 25/28; A61P 21/00
See application file for complete search history.

(56) References Cited

U.S. PATENT DOCUMENTS

| | | |
|---|---|---|
| 5,122,464 A | 6/1992 | Wilson et al. |
| 5,658,570 A | 8/1997 | Newman et al. |
| 5,736,137 A | 4/1998 | Anderson et al. |
| 5,837,821 A | 11/1998 | Wu |
| 6,159,730 A | 12/2000 | Reff |
| 6,193,980 B1 | 2/2001 | Efstathiou et al. |
| 6,413,777 B1 | 7/2002 | Reff et al. |
| 10,392,447 B2 | 8/2019 | Montrasio et al. |
| 10,961,322 B2 | 3/2021 | Montrasio et al. |
| 2003/0157641 A1 | 8/2003 | Reff et al. |
| 2004/0110938 A1 | 6/2004 | Parekh et al. |
| 2010/0040606 A1 | 2/2010 | Lantto et al. |
| 2011/0027268 A1 | 2/2011 | Kahnert et al. |
| 2013/0164293 A1 | 6/2013 | Florio et al. |
| 2013/0315821 A1 | 11/2013 | D'Souza et al. |
| 2014/0206102 A1 | 7/2014 | Petrucelli et al. |
| 2014/0303033 A1 | 10/2014 | Ehricht et al. |
| 2017/0059586 A1 | 3/2017 | Petrucelli et al. |
| 2017/0247471 A1 | 8/2017 | Montrasio et al. |
| 2017/0355756 A1 | 12/2017 | Julien et al. |
| 2017/0369590 A1 | 12/2017 | De Goeij et al. |
| 2020/0010567 A1 | 1/2020 | Montrasio et al. |

FOREIGN PATENT DOCUMENTS

| | | |
|---|---|---|
| WO | WO 1986/005807 | 10/1986 |
| WO | WO 1989/001036 | 2/1989 |
| WO | WO 1994/009817 | 5/1994 |
| WO | WO 2000/030680 | 6/2000 |
| WO | WO 2002/060955 | 8/2002 |
| WO | WO 2002/096948 | 12/2002 |
| WO | WO 2005/018572 | 3/2005 |
| WO | WO 2008/068048 | 6/2008 |
| WO | WO 2012/158948 | 11/2012 |

(Continued)

OTHER PUBLICATIONS

Paul, Fundamental Immunology, 3rd Edition, 1993, pp. 292-295.*
Rudikoff et al, Proc. Natl. Acad. Sci. USA, 79(6):1979-1983, Mar. 1982.*
MacCallum et al , J. Mol. Biol., 262, 732-745, 1996.*
Casset et al, Biochemical and Biophysical Research Communications, 2003, vol. 307, pp. 198-205.*
Holm et al (Molecular Immunology, 2007, vol. 44, pp. 1075-1084.*
Colman P. M. (Research in Immunology, 145:33-36, 1994.*
Altschul et al., "Basic local alignment search tool", Journal of Molecular Biology, Oct. 1990, 215(3):403-410.
Beck et al., "Strategies and challenges for the next generation of therapeutic antibodies," Nature reviews immunology, 2010, 10(5):345-352.

(Continued)

Primary Examiner — Mark Halvorson
(74) Attorney, Agent, or Firm — Jones Day

(57) ABSTRACT

Provided are novel dipeptide repeat (DPR) specific antibodies (e.g., human-derived antibodies) as well as synthetic variants and biotechnological derivatives thereof, capable of binding C9orf72 poly-glycine-alanine DPRs, as well as methods and uses related thereto. The antibody of the present invention can be used in pharmaceutical and diagnostic compositions for DPR protein-targeted immunotherapy and diagnostics.

18 Claims, 11 Drawing Sheets

Specification includes a Sequence Listing.

(56) References Cited

FOREIGN PATENT DOCUMENTS

| WO | WO 2014/114303 | 7/2014 |
|----|----------------|--------|
| WO | WO 2014/114660 | 7/2014 |
| WO | WO/2016/050822 | 4/2016 |
| WO | WO 2017/136313 | 8/2017 |
| WO | WO 2018/018031 | 1/2018 |

OTHER PUBLICATIONS

Biology-Online, "Expression vector," 2019, [retrieved on Mar. 8, 2019], 2 pages.

Chen et al., "Enhancement and destruction of antibody function by somatic mutation: unequal occurrence is controlled by V gene combinatorial associations," The EMBO Journal, 1995, 14(12):2784-2794.

Cockett et al., "High Level Expression of Tissue Inhibitor of Metalloproteinases in Chinese Hamster Ovary Cell using Glutamine Synthetase Gene Amplification", Nature Biotechnology, 1990, 8(7):662-667.

Davidson et al,. "Hetergeneous ribonuclear protein A3 (hnRNP A3) is present in dipeptide repeat protein containing inclusions in Frontotemporal Lobar Degeneration and Motor Neurone Disease associated with expansions in C9ORF72 gene", Acta. Neuropathologica Communications, 2017, 31:1-27.

Dejesus-Hernandez et al., "Expanded GGGGCC Hexanucleotide Repeat in Noncoding Region of C9ORF72 Causes Chromosome 9p-Linked FTD and ALS", Neuron, Oct. 2011, 72(2):245-256.

Extended European Search Report in European Application No. 14187180, dated Jul. 28, 2015, 14 pages.

Foecking et al., "Powerful and Versatile Enhancer-Promoter Unit for Mammalian Expression Vectors", Gene, 1986, 45(1):101-105.

Freibaum et al., "The role of dipeptide repeats in C9ORF72-related ALS-FTD," Frontiers in molecular neuroscience, 2017, 10:35.

Garcia-Murias et al., "'Costa da Morte' ataxia is spinocerebellar ataxia 36: Clinical and Genetic Characterization", Brain, 2012, 135(5):1423-1435.

Haberger et al., "Assessment of chemical modifications of sites in the CDRs of recombinant antibodies", mABs, Mar./Apr. 2014, 6(2):327-339.

Harms et al., "Lack of C0ORF72 coding mutations supports a gain of function for repeat expansions in ALS", Neurobiol. Aging, Sep. 2013, 34(9):2234.e13-2234.e19.

Hazenbos et al., "Novel staphylococcal glycosyltransferases SdgA and SdgB mediate immunogenicity and protection of virulence-associated cell wall proteins," PLoS pathogens, 2013, 9(10):e1003653.

Ikeda et al., "Clinical features of SCA36: A novel spinocerebellar ataxia with motor neuron involvement (Asidan)", Neurology, 2012, 79(4):333-341.

International Preliminary Report on Patentability for International Patent Application No. PCT/EP2015/072516, issued Apr. 4, 2017 (15 pages).

International Search Report and Written Opinion for International Patent Application No. PCT/EP2015/072516, mailed Apr. 19, 2016 (22 pages).

Karlin et al., "Applications and statistics for multiple high-scoring segments in molecular sequences", Proc. Natl. Aca. Sci., Jun. 1993, 90:5873-5877.

Kohler et al., "Immunoglobulin chain loss in hybridoma lines", Proceedings of the National Academy of Sciences, 1980, 77(4):2197-2199.

Koybayashi et al., "Expansion of Intronic GGCCTG Hexanucleotide Repeat in NOP56 Causes SCA36, a Type of Spincerebellar Ataxia Accompanied by Motor Neuron Involvement", AJHG, Jul. 2011, 89(1):121-130.

Kussie et al., "A single engineered amino acid substitution changes antibody fine specificity," The Journal of Immunology, 1994, 152(1):146-152.

Langer, R., "New methods of drug delivery", Science, 1990, 249(4976):1527-1533.

Lippow et al., "Computational design of antibody affinity improvement beyond in vivo maturation," Nature Biotechnology, 2007; 25 (10): 1171-1176.

Liu et al., "Heterogeneity of Monoclonal Antibodies", Journal of Pharmaceuticals Sciences, 2008, 97(7):2426-2447.

Lodish, "DNA cloning with plasmid vectors," Molecular Cell Biology, 4th Edition, 2000, 8 pages.

Mackenzie et al., "Dipeptide repeat protein pathology in C9ORF72 mutation cases: clinicopathological correlations," Acta Neuropathol. 126(6):859-79 (2013).

Mann et al., "Dipeptide repeat proteins are present in the p62 positive inclusions in patients with frontotemporal lobar degeneration and motor neuron disease associated with expansions in C9ORF72," Acta Neuropathologica Communications. 1:68 (2013) (13 pages).

May et al., "C9orf72FTLD/ALS-asnociated Gly-Ala dipeptide repeat proteins cause neuronal toxicity and Unc119 sequestration", ACTA Neuropathologica, Springer Verlag, Berlin, DE., 2014, 128(4):485-503.

Mis et al., "Development of Therapeutics for C9ORF72 ALS/FTD-Related Disorders", Molecular Neurobiology, 2017, 54:4466-4476.

Mizielinska et al., "C9orf72 repeat expansions cause neurodegeneration in *Drosophila* through arginine-rich proteins," Science. 345(6201):1192-4 (2014).

Mori et al., "Bidirectional transcripts of the expanded C9ORF72 Hexanucleotide repeat are translated into aggregating dipeptide repeat proteins", Acta. Neuropathol. 2013, 126:881-893.

Mori et al., "The C9orf72 GGGGCC repeat is translated into aggregating dipeptide-repeat proteins in FTLD/ALS," Science. 339(6125):1335-8 (2013).

Partial European Search Report in European Application No. 14187180. 6, dated Mar. 19, 2015, 9 pages.

PCT International Preliminary Report on Patentability in International Appln. No. PCT/US2019/029109, dated Aug. 12, 2019, 8 pages.

PCT International Search Report and Written Opinion in International Appln. No. PCT/US2019/029109, dated Aug. 12, 2019, 11 pages.

Proudfoot, N. J., "Transcriptional interference and termination between duplicated a-globin gene constructs suggests a novel mechanism for gene regulation", Nature, Aug. 1986, 322:562-565.

Rajpal et al., "A general method for greatly improving the affinity of antibodies by using combinatorial libraries," PNAS, 2005; 102, 8466-8471.

Renton et al., "A Hexanucleotide Repeat Expansion in C9ORF72 is the cause of Chormosome 9p21-Linked ALS-FTD", Neuron, Oct. 2011, 72(2):257-268.

Steinitz, "Three decades of human monoclonal antibodies: past, present and future developments," Hum Antibodies. 18(1-2):1-10 (2009).

Vajdos et al., "Comprehensive Functional Maps of the Antigen-binding Site of an Anti-ErbB2 Antibody Obtained with Shotgun Scanning Mutagenesis," J. Mol. Biol., 2002; 320 (2): 415-428.

Vance et al., "Familial amyotrophic lateral sclerosis with frontotemporal dementia is linked to a locus on chromosome 9p13.2-21.3", Brain, 2006, 129:868-876.

Zhou et al., "Antibodies Inhibt transmission and aggregation of C9orf72 poly-GA dipeptide repeat proteins", EMBO Molecular Medicine, Mar. 28, 2017, 9(5):687-702.

Zu et al., "RAN proteins and RNA foci from antisense transcripts in C9ORF72 ALS and frontotemporal dementia," Proc Natl Acad Sci U S A. 110(51):E4968-77 (2013).

U.S. Appl. No. 15/508,343, U.S. Pat. No. 10,392,447, filed Mar. 2, 2017, Montrasio.

U.S. Appl. No. 16/434,654, U.S. Pat. No. 10,961,322, filed Jun. 7, 2019, Montrasio.

Mirsky et al., "Antibody-specific model of amino acid substitution for immunological inferences from alignments of antibody sequences," Mol. Biol. Evol., Mar. 2015, 32(3):806-819.

U.S. Appl. No. 15/508,343, 2017/0247471, U.S. Pat. No. 10,392,447, filed Mar. 2, 2017, Montrasio.

U.S. Appl. No. 16/434,654, 2020/0010567, U.S. Pat. No. 10,961,322, filed Jun. 7, 2019, Montrasio.

U.S. Appl. No. 17/183,894, filed Feb. 24, 2021, Montrasio.

(56) References Cited

OTHER PUBLICATIONS

U.S. Appl. No. 17/507,223, filed Oct. 21, 2021, Montrasio.
U.S. Appl. No. 17/731,697, filed Apr. 28, 2022, Montrasio.
U.S. Appl. No. 18/074,736, filed Dec. 5, 2022, Montrasio.
U.S. Appl. No. 18/492,146, filed Oct. 23, 2023, Montrasio.

* cited by examiner

(A) NI-308.5J10 VH (variable heavy chain sequence VH) (SEQ ID NO: 2)
```
FR1--------------------------CDR1-FR2----------CDR2--------
QVQLQESGPGLVKPSETLSLTYTVLGGSVSDYYWSCIRQPAGKGLEWIGRTYTNGKTTYTYN
-----FR3-----------------------------CDR3----------FR4--------
PSLESRLSLSIDTSMNQFSLKLTSVTAADTAVYYCARWGAVTGDYYYGMDVWGPGTLVTVSS
```

NI-308.5J10 VK (variable light chain sequence VK) (SEQ ID NO: 7)
```
FR1-------------------CDR1-----------FR2------------CDR2---
EIVLTQSPLSLSVTPGEPASISCRSPRSLLHTNGYTYLDWYLQRPGQSPQLLIFLASNRAS
FR3--------------------------CDR3-----FR4-------
GVPDRFSGSGSGTNFTLRISGVEADDVGVYYCMQGLQPSWTFGQGTKVEIK
```

(B) NI-308.5J10 VH N54S (variable heavy chain sequence VH N54S) (SEQ ID NO: 12)
```
FR1--------------------------CDR1-FR2----------CDR2--------
QVQLQESGPGLVKPSETLSLTYTVLGGSVSDYYWSCIRQPAGKGLEWIGRTYTSGKTTYTYN
-----FR3-----------------------------CDR3----------FR4--------
PSLESRLSLSIDTSMNQFSLKLTSVTAADTAVYYCARWGAVTGDYYYGMDVWGPGTLVTVSS
```

(C) NI-308.5J10 VH N54T (variable heavy chain sequence VH N54T) (SEQ ID NO: 15)
```
FR1--------------------------CDR1-FR2----------CDR2--------
QVQLQESGPGLVKPSETLSLTYTVLGGSVSDYYWSCIRQPAGKGLEWIGRTYTTGKTTYTYN
-----FR3-----------------------------CDR3----------FR4--------
PSLESRLSLSIDTSMNQFSLKLTSVTAADTAVYYCARWGAVTGDYYYGMDVWGPGTLVTVSS
```

(D) NI-308.5J10 VH G55S (variable heavy chain sequence VH G55S) (SEQ ID NO: 18)
```
FR1--------------------------CDR1-FR2----------CDR2--------
QVQLQESGPGLVKPSETLSLTYTVLGGSVSDYYWSCIRQPAGKGLEWIGRTYTNSKTTYTYN
-----FR3-----------------------------CDR3----------FR4--------
PSLESRLSLSIDTSMNQFSLKLTSVTAADTAVYYCARWGAVTGDYYYGMDVWGPGTLVTVSS
```

(E) NI-308.5J10 VH G55T (variable heavy chain sequence VH G55T) (SEQ ID NO: 21)
```
FR1--------------------------CDR1-FR2----------CDR2--------
QVQLQESGPGLVKPSETLSLTYTVLGGSVSDYYWSCIRQPAGKGLEWIGRTYTNTKTTYTYN
-----FR3-----------------------------CDR3----------FR4--------
PSLESRLSLSIDTSMNQFSLKLTSVTAADTAVYYCARWGAVTGDYYYGMDVWGPGTLVTVSS
```

(F) NI-308.5J10 VK N75D (variable light chain sequence VK N75D) (SEQ ID NO: 24)
```
FR1-------------------CDR1-----------FR2------------CDR2---
EIVLTQSPLSLSVTPGEPASISCRSPRSLLHTNGYTYLDWYLQRPGQSPQLLIFLASNRAS
FR3--------------------------CDR3-----FR4-------
GVPDRFSGSGSGTDFTLRISGVEADDVGVYYCMQGLQPSWTFGQGTKVEIK
```

(A) NI-308.5J10
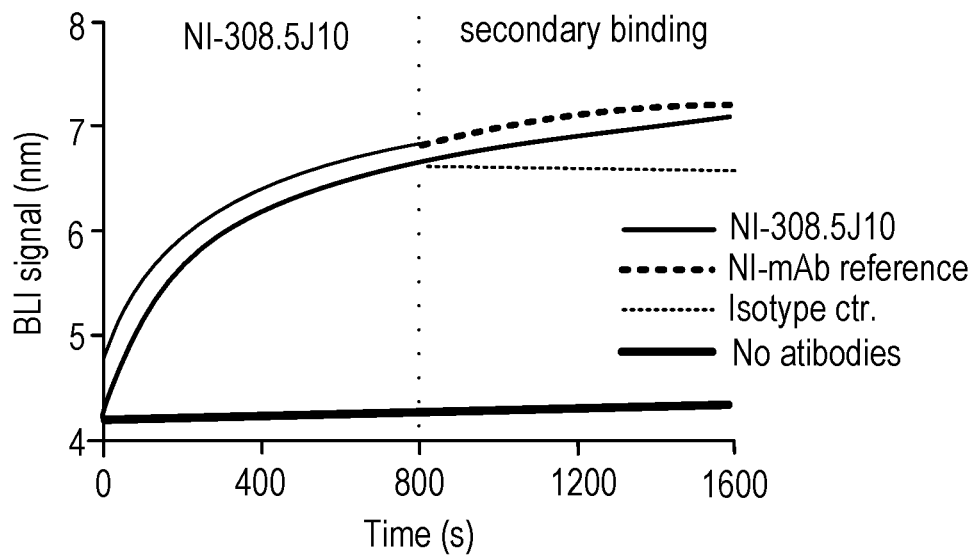
(B) NI-mAb reference
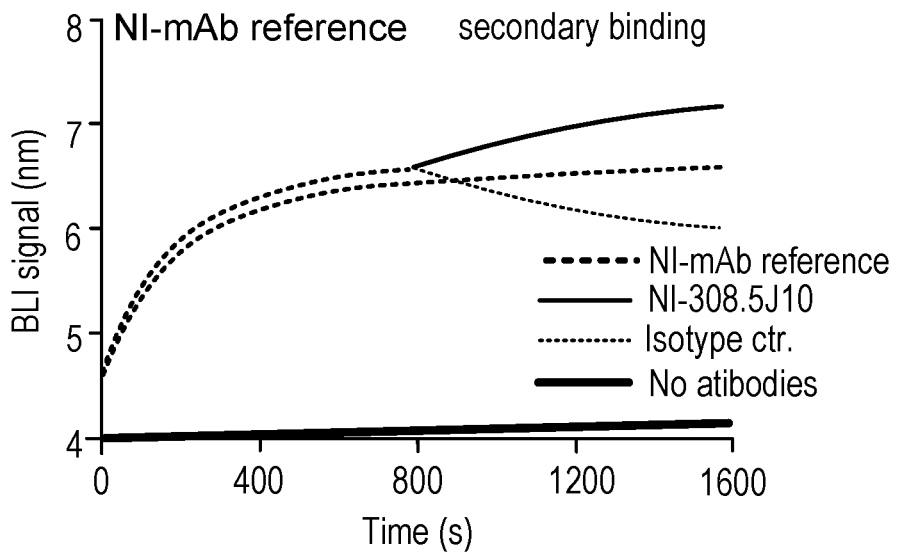
Fig. 8

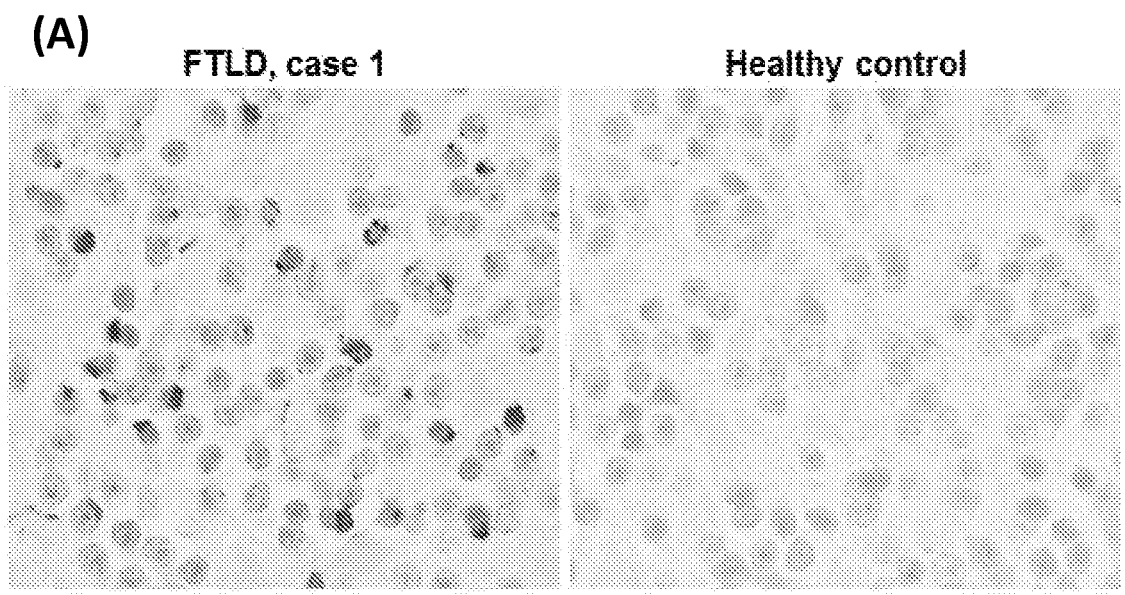
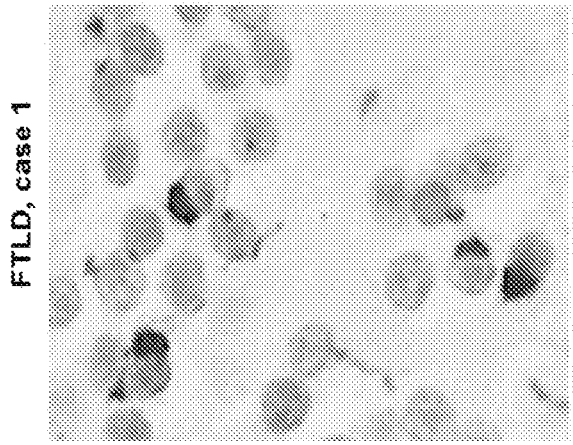
Fig. 10

FIG. 13B
Crystal structure: DPR Ab-1 Fab-GA
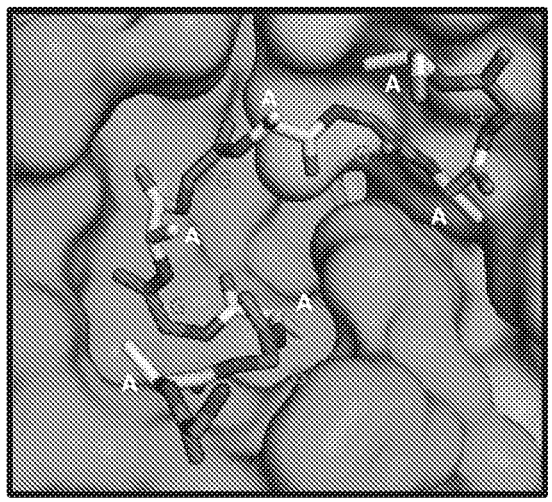
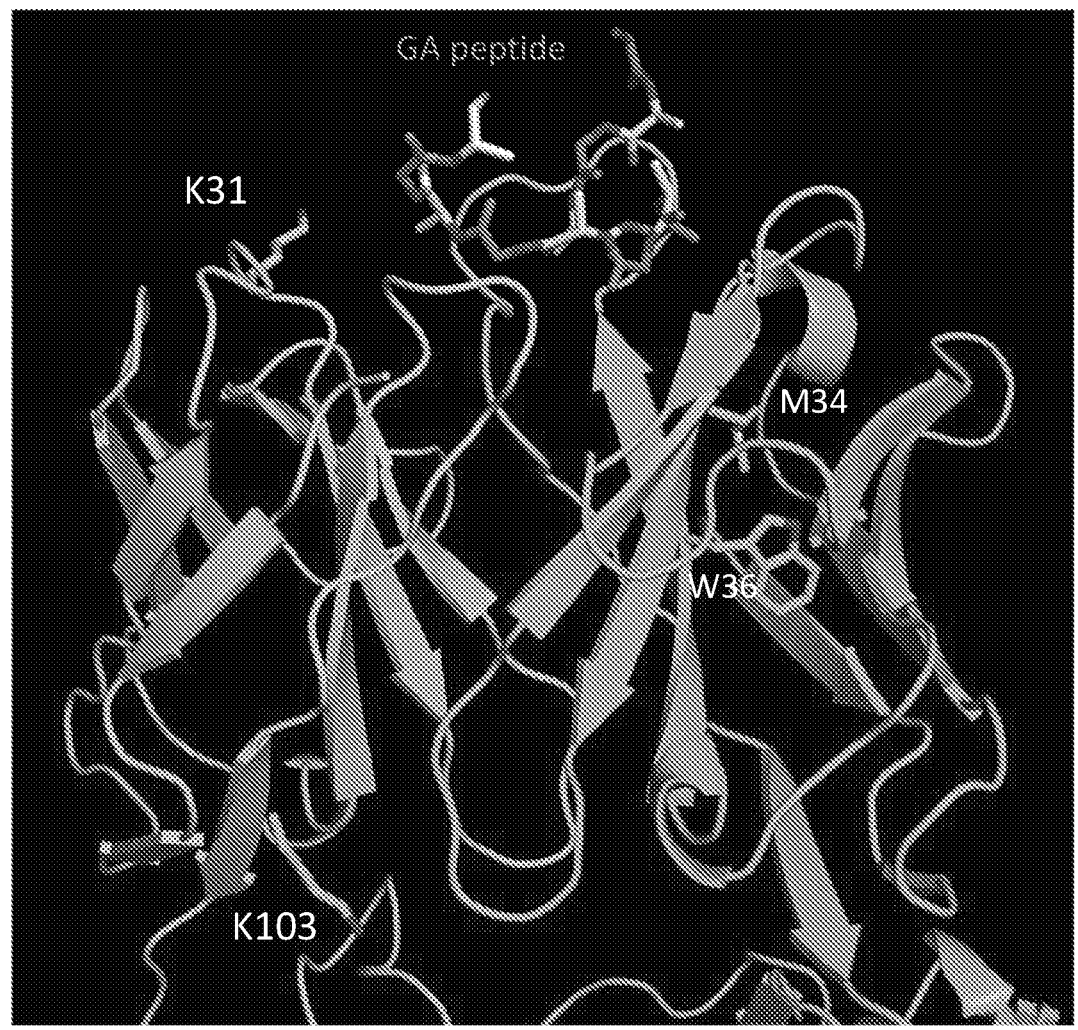

HUMAN-DERIVED ANTI-(POLY-GA) DIPEPTIDE REPEAT (DPR) ANTIBODY

CROSS-REFERENCE TO RELATED APPLICATIONS

This application is the National Stage of International Application No. PCT/US2019/029109, filed on Apr. 25, 2019, which claims priority to European Patent Application No. 18169888.7, filed Apr. 27, 2018, and U.S. Provisional Application No. 62/772,809, filed Nov. 29, 2018, the content of each of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Apr. 24, 2019, is named 13751-0309WO1_SL.txt and is 102,178 bytes in size.

FIELD OF THE INVENTION

The present invention generally relates to antibody-based therapies and diagnostic methods. In particular, the present invention relates to a novel human-derived antibody as well as fragments, derivatives and biotechnological variants thereof specifically binding to unconventional non-ATG translations, in particular hexanucleotide repeats forming poly-glycine-alanine (poly-GA) dipeptide repeats (DPRs) as found in chromosome 9 open reading frame 72 (C9orf72) and antigens comprising such DPRs, which are useful in the treatment and diagnosis of diseases and conditions induced by aggregated DPRs and DPRs containing proteins, respectively. In addition, the present invention relates to pharmaceutical and diagnostic compositions comprising the antibody and its variants and derivatives thereof valuable both as a diagnostic tool to identify diseases associated with DPRs or its aggregates and also as a passive vaccination strategy for treating such diseases, for example Frontotemporal lobar degeneration (FTLD), amyotrophic lateral sclerosis (ALS), FTLD-ALS, and spinocerebellar ataxia type 36.

BACKGROUND OF THE INVENTION

Frontotemporal lobar degeneration (FTLD) belongs to a group of clinically, pathologically and genetically heterogeneous disorders associated with atrophy in the frontal lobe and temporal lobe of the brain. It is the second most common cause of early-onset of dementia. Cognitive symptoms are variable and include dementia, changes of the behavior as well as personality, language dysfunctions, and/or psychosis with are due to the degeneration of the frontal and temporal cortex. Due to its symptoms FTLD can be divided into three groups (i) behavioral-variant frontotemporal dementia (bvFTLD), (ii) semantic dementia (SD), or (iii) progressive nonfluent aphasia (PNFA). Patients with FTLD die 5-10 years after symptom onset, since no suitable therapy is available. However, 50% of FTLD patient were shown to have a positive family history and compared to amyotrophic lateral sclerosis (ALS) seems to represent a disease continuum with a shared underlying pathogenesis. Although both autosomal dominant disorders were shown to be genetically and pathologically heterogeneous, see, e.g., Vance et al., Brain 129 (2006), 868-876, genetic analysis identified a heterozygous expanded hexanucleotide repeat (GGGGCC) located between the noncoding exons 1a and 1b of the C9orf72 gene as the most common genetic cause of FTLD and ALS; see, e.g., DeJesus-Hernandez et al., Neuron 72 (2011), 245-256 and Renton et al., Neuron 72 (2011), 257-268. In particular, it was shown that the unconventional non-ATG translation of the sense transcript in the three alternate reading frames, i.e. of the expanded hexanucleotide repeats, resulted in the production, generation and aggregation of three different polypeptides, each composed of repeating units of two amino acids (dipeptide repeats, DPRs), i.e. poly-(Gly-Ala; GA), poly-(Gly-Pro; GP) and poly-(Gly-Arg; GR). Furthermore, translation of corresponding antisense transcripts results in the generation of poly-(Pro-Arg; PR), poly-(Pro-Ala; PA), and poly-(Gly-Pro; GP). These C9orf72-dipeptide repeat (DPR) expansions were shown to account for up to 30% of FTLD, 50% of ALS and 80% of FTLD-ALS patients with the highest mutation frequencies observed in US and EU Caucasian populations. Additionally, patients with C9orf72-DPR expansion with more than 19 repeats had a lower age of onset, increased incidence of neurological disorders, and a propensity towards psychosis or hallucinations compared to patients with other forms of FTLD and/or ALS; see, e.g., Harms et al., Neurobiol. Aging 34 (2013), e13-e19.

Treatments for diseases and/or disorders associated with a dipeptide repeat (DPR) expansion, e.g. medicaments which slow down the progression of the disease, are missing. The major focus of medical care so far relied in the provision of pharmaceuticals for the treatment of the often very stressful accompanying symptoms.

The most prominent recent approaches in therapeutic targeting of the pathological expansion of C9orf72 for ALS, FTLD, and other neurodegenerative disorders focus on antisense oligonucleotides/RNA interference (RNAi) strategy, using small compounds to counteract the toxic effects directly exerted by RNA derived from the repeat transcription (foci), by the translation of dipeptide repeat proteins (DPRs) from the repeated sequence, or by the sequestration of RNA-binding proteins from the C9orf72 expansion, and gene therapy, not only for silencing the toxic RNA/protein, but also for rescuing haploinsufficiency caused by the reduced transcription of the C9orf72 coding sequence or by the diminished availability of RNA-binding proteins that are sequestered by RNA foci; see, e.g., for review Misc. et al., Mol. Neurobiol. 54 (2017), 4466-4476.

While it may be tempting to consider antibody targeting of DPR proteins in the brain of patients with the hexanucleotide repeat expansion of C9orf72, so far it appears as if this approach has not been duly considered or may suffer from the actual approach taken. For example, the group of Edbauer et al. describe the generation of antibodies against an oligopeptide consisting of dipeptide repeats of the sequence (Gly-Ala) by immunization of mice with aggregated $(GA)_{10}$ peptides (SEQ ID NO: 72), which were shown to bind to GST-fusion proteins containing GA-DPR $(GA)_{15}$ (SEQ ID NO: 66); see international application WO 2014/114660. One of those antibodies, designated GA-5F2 could be shown to inhibit transmission and aggregation of C9orf72 poly-GA dipeptide repeat proteins in co-culture assays and cell extracts in vitro; see Zhou et al., EMBO Molecular Medicine 9 (2017), 687-702.

However, besides the drawback of mouse monoclonal antibodies which are prone to eliciting a human anti-mouse antibody (HAMA) response in the human body, due to the fact that the monoclonal antibody has been raised against an artificial antigen it is not clear whether the binding of DPR-$GA_{15}$ translates to a corresponding specificity and affinity for DPR proteins from the C9orf72 gene as present in the brain of patients suffering from ALS, FTLD and other neurodegenerative disorders.

Indeed, it appears as if academics and industry still remain focusing on RNA targeted treatment strategies for C9orf72 ALS/FTLD; see, e.g., the recent publication by Simone et al., EMBO Molecular Medicine 10 (2018), 22-31 and the commentary by Schludi & Edbauer, EMBO Molecular Medicine 10 (2018), 4-6, which report on the promising results on targeting RNA G-quadruplex for amelioration of C9orf72 ALS/FTLD pathology in vitro and in vivo, in GGGGCC repeat-expressing *Drosophila*.

However, RNA based therapeutics, small organic compounds, and gene therapy suffer from several drawback such as the inherent instability of RNA, potentially immunogenic properties of the compound and requiring a delivery vehicle for efficient transport to the targeted cell as well as ethical issues regarding the application of gene therapy remain.

Accordingly, there is still a need for the development of new drugs in the therapeutic targeting of the pathological expansion of C9orf72 in the treatment of ALS, FTLD and other neurodegenerative disorders, which are specific for the disease and disorder caused by expression products of the C9orf72 gene, and optionally belong to a well investigated class of drugs and are tolerable in humans.

This technical problem is solved by the embodiments characterized in the claims and described further below and illustrated in the Examples and Figures.

SUMMARY OF THE INVENTION

The present invention provides human-derived monoclonal antibodies capable of binding dipeptide repeats (DPRs) and DPR containing proteins (DPR proteins) consisting of poly-glycine-alanine (Gly-Ala; GA) repeats as well as equivalent DPR protein-binding molecules such as DPR-binding fragments, synthetic variants and biotechnological derivatives of the antibodies exemplified herein which are particularly useful in the prophylactic or therapeutic treatment of diseases and conditions associated with DPR proteins and aggregated forms thereof.

Recently, a class of human-derived anti-DPR antibodies has been described which hold great promise for the development of antibody-based therapeutic intervention in the treatment of C9orf72-ALS and FTLD patients; see international application WO 2016/050822, the disclosure content of which is incorporated herein by reference. As described therein, the anti-DPR protein antibodies and their cDNAs encoding the variable regions, respectively, have been isolated from patients who were symptom-free of neurological and neurodegenerative conditions; see WO 2016/050822 at page 3 and in the Examples. In further experiments performed in accordance with the present invention, an anti-poly-GA DPR antibody could be identified and cloned, designated NI-308.5J10 and hereinafter also referred to as the "subject antibody", which could be shown to have unique binding characteristics as determined in different binding assays and in particular on brain tissue derived from selected human C9orf72-FTLD patients; see Example 11 and FIG. 10. Moreover, as demonstrated in Example 9 and FIG. 8, the subject antibody's binding to aggregated C9orf72 poly-GA DPR $(GA)_{15}$ (SEQ ID NO: 66) is not blocked by prior binding to the target by a reference anti-poly GA antibody (NI-mAb reference) while the binding of the reference anti-poly GA antibody to the C9orf72 DPR peptides is abrogated by the prior binding of the subject NI-308.5J10 antibody to the target.

Thus, though the subject NI-308.5J10 antibody and the reference anti-poly GA antibody both have been selected for and recognize C9orf72 poly-GA DPR protein or aggregated forms there, the subject antibody surprisingly seems to recognize additional conformational epitopes on the poly-GA peptides. This property makes the antibody in particular suitable for targeting C9orf72 DPR protein in patients carrying a C9orf72 hexanucleotide repeat expansion, since poly-GA DPR protein aggregates often co-aggregate with other DPR proteins and/or unrelated aggregating proteins such as p62 and hnRNP A3 (Mori et al., Acta Neuropathol. 126 (2013), 881-893; Mann et al., Acta Neuropathologica. Communications (2013), 1:68. doi:10.1186/2051-5960-1-68; Davidson et al., Acta Neuropathologica Communications (2017); 5:31. doi:10.1186/s40478-017-0437-5).

In addition, further experiments carried out within the scope of the present invention revealed that amino acids in the CDRs and the framework region, which are prone to deamidation or glycosylation could be substituted without losing the essential binding characteristics of the subject antibody; see Examples 12 to 15 and FIG. 11.

Thus, the present invention also provides variants and derivatives of the original human-derived anti-DPR antibody, which contain one or more amino acid substitutions within the CDRs and/or framework region that let to improved manufacturability of the antibody while the binding characteristics and stability of the antibody remained unaffected in kind or are even improved; see Examples 15 and 16. In addition, due to the only minor modification in the CDRs and/or variable region, also the subject variants and derivatives of the original NI-308.5J10 antibody are expected to be substantially non-immunogenic in humans.

In summary, the present invention as disclosed in the present application provides a human derived anti-poly GA antibody as well as variants and derivatives thereof of having properties which make them particularly suitable for targeting C9orf72 DPR protein or aggregated forms thereof in the human brain and thus for immunotherapy of C9orf72 ALS/FTLD patients.

Accordingly, the present invention generally relates to the following embodiments:

[1] An antibody capable of binding a dipeptide repeat (DPR) of poly-glycine-alanine (GA) having at least 6 repeats $(GA)_6$ (SEQ ID NO: 80) as translated from the chromosome 9 open reading frame 72 (C9orf72) gene, or a DPR-binding fragment thereof, wherein the antibody or DPR-binding fragment thereof comprises in its variable region the following six complementarity determining regions (CDRs):
  (a) VH-CDR1 comprising the amino acid sequence of SEQ ID NO: 3 (e.g., comprises SEQ ID NO: 78) or a variant thereof, wherein the variant comprises one or two amino acid substitutions,
  (b) VH-CDR2 comprising the amino acid sequence of SEQ ID NO: 4 or a variant thereof, wherein the variant comprises one or two amino acid substitutions,
  (c) VH-CDR3 comprising the amino acid sequence of SEQ ID NO: 5 or a variant thereof, wherein the variant comprises one or two amino acid substitutions,
  (d) VL-CDR1 comprising the amino acid sequence of SEQ ID NO: 8 or a variant thereof, wherein the variant comprises one or two amino acid substitutions,
  (e) VL-CDR2 comprising the amino acid sequence of SEQ ID NO: 9 or a variant thereof, wherein the variant comprises one or two amino acid substitutions,
  (f) VL-CDR3 comprising the amino acid sequence of SEQ ID NO: 10 or a variant thereof, wherein the variant comprises one or two amino acid substitutions, optionally wherein the antibody is a human-derived antibody, optionally wherein the antibody is a monoclonal antibody, optionally wherein the antibody is a human-derived monoclonal antibody.

[2] The antibody or DPR-binding fragment thereof of [1] comprising in its variable region
  (a) a variable heavy ($V_H$) chain comprising the amino acid sequence depicted in SEQ ID NO: 2 or a variant thereof, wherein the variant comprises one or more amino acid substitutions; and
  (b) a variable light ($V_L$) chain comprising the amino acid sequence depicted in SEQ ID NO: 7, or a variant thereof, wherein the variant comprises one or more amino acid substitutions; optionally wherein
    the $V_H$ and $V_L$ chain amino acid sequence is at least 90% identical to SEQ ID NO: 2 and 7, respectively.

[3] The antibody or DPR-binding fragment thereof of [1] or [2], wherein
  (a) the CDRs do not contain a deamidation-prone asparagine (N) and/or glutamine (Q); and/or
  (b) the $V_H$ and/or $V_L$ chain amino acid sequences do not contain an occupied glycosylation site.

[4] The antibody or DPR-binding fragment thereof of any one of [1] to [3], wherein the one, two or more amino acid substitutions are selected from
  (a) substitution of a deamidation-prone asparagine (N) or glutamine (Q) with a non-deamidation-prone amino acid;
  (b) substitution of a small, flexible amino acid being directly adjacent to a deamidation-prone N or Q with a larger amino acid, optionally wherein the adjacent amino acid is glycine (G);
  (c) substitution of at least one amino acid which leads to removal of a glycosylation site, optionally wherein the at least one amino acid is within the glycosylation motif NXS or NXT; and/or
  (d) substitution of one or more amino acids which are conservative amino acid substitutions.

[5] The antibody or DPR-binding fragment thereof of [4], wherein the amino acid substitution(s) of (a) and (b) are present in VH-CDR2 and the amino acid substitution(s) of (c) are present in the $V_L$ chain.

[6] The antibody or DPR-binding fragment thereof of [5], wherein
  (i) in VH-CDR2 the asparagine (N) corresponding to position 54 and/or the glycine (G) corresponding to position 55 of SEQ ID NO: 2 are substituted with another amino acid, optionally wherein the asparagine (N) is substituted with serine (S) or threonine (T) and/or wherein the glycine (G) is substituted with serine (S) or threonine (T); and/or
  (ii) in the $V_L$ chain the asparagine (N) corresponding to position 75 of SEQ ID NO: 7 is substituted with another amino acid, optionally wherein the asparagine (N) is substituted with aspartic acid (D).

[7] The antibody or DPR-binding fragment thereof of any one of [1] to [6], wherein the antibody or DPR-binding fragment has a binding affinity to a poly-$(GA)_8$ peptide (SEQ ID NO: 81) corresponding to a $K_D$ (dissociation constant) less than 30 nM with a $K_a$ (association rate) less than $5 \times 10^5$ $M^{-1}s^{-1}$ and a $K_d$ (dissociation rate) of less than $10 \times 10^{-3}$ $s^{-1}$ as determined by Surface Plasmon Resonance (SPR), optionally wherein the DPR-binding fragment has a binding affinity to corresponding to a $K_D$ (dissociation constant) of 10 nM to 30 nM with a $K_a$ (association rate) of 1 to $5 \times 10^5$ $M^{-1}s^{-1}$ and a $K_d$ (dissociation rate) of 2.5 to $10 \times 10^{-3}$ $s^{-1}$ as determined by Surface Plasmon Resonance (SPR).

[8] The antibody or DPR-binding fragment thereof of any one of [1] to [7], wherein the Fab fragment thereof has a thermal stability and melting temperature $T_m$, respectively, in the range of 78-82° C., for example, in the range of about 79-81° C. as determined by Differential Scanning calorimetry (VP-DSC).

[9] The antibody or DPR-binding fragment thereof of any one of [1] to [8], which comprises in its variable region
  (i) the following six CDRs:
    (a) a VH-CDR1 comprising the amino acid sequence of SEQ ID NO: 3 (e.g., comprises SEQ ID NO:78),
    (b) a VH-CDR2 comprising the amino acid sequence of SEQ ID NO: 13,
    (c) a VH-CDR3 comprising the amino acid sequence of SEQ ID NO: 5,
    (d) a VL-CDR1 comprising the amino acid sequence of SEQ ID NO: 8,
    (e) a VL-CDR2 comprising the amino acid sequence of SEQ ID NO: 9,
    (f) a VL-CDR3 comprising the amino acid sequence of SEQ ID NO: 10;
  (ii) the following six CDRs:
    (a) a VH-CDR1 comprising the amino acid sequence of SEQ ID NO: 3 (e.g., comprises SEQ ID NO:78),
    (b) a VH-CDR2 comprising the amino acid sequence of SEQ ID NO: 14,
    (c) a VH-CDR3 comprising the amino acid sequence of SEQ ID NO: 5,
    (d) a VL-CDR1 comprising the amino acid sequence of SEQ ID NO: 8,
    (e) a VL-CDR2 comprising the amino acid sequence of SEQ ID NO: 9,
    (f) a VL-CDR3 comprising the amino acid sequence of SEQ ID NO: 10;
  (iii) the following six CDRs:
    (a) a VH-CDR1 comprising the amino acid sequence of SEQ ID NO: 3 (e.g., comprises SEQ ID NO:78),
    (b) a VH-CDR2 comprising the amino acid sequence of SEQ ID NO: 19,
    (c) a VH-CDR3 comprising the amino acid sequence of SEQ ID NO: 5,
    (d) a VL-CDR1 comprising the amino acid sequence of SEQ ID NO: 8,
    (e) a VL-CDR2 comprising the amino acid sequence of SEQ ID NO: 9,
    (f) a VL-CDR3 comprising the amino acid sequence of SEQ ID NO: 10;
  (iv) the following six CDRs:
    (a) a VH-CDR1 comprising the amino acid sequence of SEQ ID NO: 3 (e.g., comprises SEQ ID NO:78),
    (b) a VH-CDR2 comprising the amino acid sequence of SEQ ID NO: 22,
    (c) a VH-CDR3 comprising the amino acid sequence of SEQ ID NO: 5,
    (d) a VL-CDR1 comprising the amino acid sequence of SEQ ID NO: 8,
    (e) a VL-CDR2 comprising the amino acid sequence of SEQ ID NO: 9,
    (f) a VL-CDR3 comprising the amino acid sequence of SEQ ID NO: 10; or
  (v) the following six CDRs:
    (a) a VH-CDR1 comprising the amino acid sequence of SEQ ID NO: 3 (e.g., comprises SEQ ID NO:78), (b) a VH-CDR2 comprising the amino acid sequence of SEQ ID NO: 4,
(c) a VH-CDR3 comprising the amino acid sequence of SEQ ID NO: 5,
(d) a VL-CDR1 comprising the amino acid sequence of SEQ ID NO: 8,
(e) a VL-CDR2 comprising the amino acid sequence of SEQ ID NO: 9,
(f) a VL-CDR3 comprising the amino acid sequence of SEQ ID NO: 10.

[9a] The antibody or DPR-binding fragment thereof of any one of [1] to [8], which comprises in its variable region the following six CDRs:
(a) a VH-CDR1 comprising the amino acid sequence of SEQ ID NO: 3 (e.g., comprises SEQ ID NO:78),
(b) a VH-CDR2 comprising the amino acid sequence of SEQ ID NO: 13,
(c) a VH-CDR3 comprising the amino acid sequence of SEQ ID NO: 5,
(d) a VL-CDR1 comprising the amino acid sequence of SEQ ID NO: 8,
(e) a VL-CDR2 comprising the amino acid sequence of SEQ ID NO: 9, and
(f) a VL-CDR3 comprising the amino acid sequence of SEQ ID NO: 10.

[10] The antibody or DPR-binding fragment thereof of any one of [1] to [9a] comprising in its variable region
(i) the $V_H$ and $V_L$ chain amino acid sequence as depicted in SEQ ID NO: 12 and SEQ ID NO: 24;
(ii) the $V_H$ and $V_L$ chain amino acid sequence as depicted in SEQ ID NO: 2 and SEQ ID NO: 24;
(iii) the $V_H$ and $V_L$ chain amino acid sequence as depicted in SEQ ID NO: 15 and SEQ ID NO: 24;
(iv) the $V_H$ and $V_L$ chain amino acid sequence as depicted in SEQ ID NO: 18 and SEQ ID NO: 24;
(v) the $V_H$ and $V_L$ chain amino acid sequence as depicted in SEQ ID NO: 21 and SEQ ID NO: 24;
(vi) the $V_H$ and $V_L$ chain amino acid sequence as depicted in SEQ ID NO: 12 and SEQ ID NO: 7;
(vii) the $V_H$ and $V_L$ chain amino acid sequence as depicted in SEQ ID NO: 15 and SEQ ID NO: 7;
(viii) the $V_H$ and $V_L$ chain amino acid sequence as depicted in SEQ ID NO: 18 and SEQ ID NO: 7;
(ix) the $V_H$ and $V_L$ chain amino acid sequence as depicted in SEQ ID NO: 21 and SEQ ID NO: 7; or
(x) the $V_H$ and $V_L$ chain amino acid sequence as depicted in SEQ ID NO: 2 and SEQ ID NO:7.

[10a] The antibody or DPR-binding fragment thereof of any one of [1] to [10] comprising in its variable region a $V_H$ chain comprising an amino acid sequence that is at least 90% identical to the amino acid sequence of SEQ ID NO: 12.
[10b] The antibody or DPR-binding fragment thereof of any one of [1] to [10a] comprising in its variable region a $V_L$ chain comprising an amino acid sequence that is at least 90% identical to the amino acid sequence of SEQ ID NO: 24.
[10c] The antibody or DPR-binding fragment thereof of any one of [1] to [10b] comprising in its variable region a $V_H$ chain comprising an amino acid sequence that is at least 95% identical to the amino acid sequence of SEQ ID NO: 12.
[10d] The antibody or DPR-binding fragment thereof of any one of [1] to [10c] comprising in its variable region a $V_L$ chain comprising an amino acid sequence that is at least 95% identical to the amino acid sequence of SEQ ID NO: 24.
[10e] The antibody or DPR-binding fragment thereof of any one of [1] to [10d] comprising in its variable region a $V_H$ chain comprising an amino acid sequence that is at least 99% identical to the amino acid sequence of SEQ ID NO: 12.
[10f] The antibody or DPR-binding fragment thereof of any one of [1] to [10e] comprising in its variable region a $V_L$ chain comprising an amino acid sequence that is at least 99% identical to the amino acid sequence of SEQ ID NO: 24.
[10g] The antibody or DPR-binding fragment thereof of any one of [1] to [10f] comprising in its variable region a $V_H$ chain comprising a variant of the amino acid sequence of SEQ ID NO: 12 with 1, 2, or 3 additions, substitutions, or deletions relative to the amino acid sequence of SEQ ID NO: 12.
[10h] The antibody or DPR-binding fragment thereof of any one of [1] to [10g] comprising in its variable region a $V_L$ chain comprising a variant of the amino acid sequence of SEQ ID NO: 24 with 1, 2, or 3 additions, substitutions, or deletions relative to the amino acid sequence of SEQ ID NO: 24.
[10i] The antibody or DPR-binding fragment thereof of any one of [1] to [10h] comprising in its variable region a $V_H$ chain comprising the amino acid sequence of SEQ ID NO: 12.
[10j] The antibody or DPR-binding fragment thereof of any one of [1] to [10i] comprising in its variable region a $V_H$ chain comprising the amino acid sequence of SEQ ID NO: 24.

[11] The antibody or DPR-binding fragment thereof of any one of [1] to [10j] further comprising a heterologous polypeptide sequence which is optionally heterologous to the CDRs or $V_H$ and $V_L$ chain amino acid sequence, optionally wherein the heterologous polypeptide sequence comprises a human constant domain, optionally of the IgG type, optionally of the IgG1 class or isotype.
[11a] The antibody or DPR-binding fragment thereof of [11], wherein the heterologous polypeptide sequence is heterologous to the CDRs.
[11b] The antibody or DPR-binding fragment thereof of [11], wherein the heterologous polypeptide sequence is heterologous to the $V_H$ and $V_L$.
[11c] The antibody or DPR-binding fragment thereof of any one of [11] to [11b], wherein the heterologous polypeptide sequence is a light chain constant domain, optionally of the kappa type.
[11d] The antibody or DPR-binding fragment thereof of any one of [11] to [11b], wherein the heterologous polypeptide sequence is a heterologous mammalian secretory signal peptide.
[12] The antibody or DPR-binding fragment thereof of any one of [1] to [11d], which binds to the poly-GA peptide only if the repeat number n is ≥6, optionally.
[13] The antibody or DPR binding fragment thereof of any one of [1] to [12], wherein the antibody recognizes a linear and a conformational epitope on poly-$(GA)_{15}$ peptides (SEQ ID NO: 66).
[14] The antibody or DPR-binding fragment thereof of any one of [1] to [13], wherein the antibody binds with an affinity KD of about (0.05-0.5 nM, optionally 0.1-0.2 nM) to poly-$(GA)_{15}$ peptides (SEQ ID NO: 66) with an association rate constant of ($K_a$=0.5-5×10$^5$ M$^{-1}$s$^{-1}$) and dissociation constant ($K_d$=1-5×10$^{-5}$ s$^{-1}$) as determined by biolayer interferometry.
[15] The antibody or DPR-binding fragment thereof of any one of [1] to [14], wherein the antibody binds to the poly-GA peptide coupled to BSA carrier protein with substantially the same affinity as to corresponding hydrophobically coated peptides.
[16] The antibody or DPR-binding fragment thereof of any one of [1] to [15], which has substantially no or minimal cross-reactivity to unrelated amyloidogenic proteins.

[17] The antibody or DPR-binding fragment thereof of any one of [1] to [16], wherein the antibody is capable of binding DPR-containing proteins as translated from the C9orf72 gene or aggregated forms thereof in the granule cell layer of the cerebellum of a C9orf72-FTLD patient.

[18] The antibody or DPR-binding fragment thereof of any one of [1] to [17], which if administered to a transgenic C9orf72 mouse model is capable of ameliorating at least one symptom of pathological hallmarks of C9orf72 disease such as neuronal loss, behavioral abnormalities, motor deficits and decreased survival.

[19] The antibody of any one of [1] to [18], which is selected from the group consisting of a single chain Fv fragment (scFv), an F(ab') fragment, an F(ab) fragment, and an F(ab')2 fragment.

[20] The antibody of any one of [1] to [19] which is a chimeric murine-human or a murinized antibody.

[21] One or more polynucleotide(s) encoding the antibody or DPR-binding fragment thereof of any one of [1] to [20] or an immunoglobulin $V_H$ or $V_L$ chain thereof, optionally wherein the polynucleotide is a cDNA and/or operably linked to a heterologous nucleic acid.

[21a] A polynucleotide encoding a $V_H$ chain of the antibody or DPR-binding fragment thereof of any one of [1] to [20], wherein the $V_H$ chain when paired with a $V_L$ chain comprising the amino acid sequence of SEQ ID NO:24 binds to a DPR of poly-GA having at least 6 repeats as translated from the C9orf72 gene, or a DPR-binding fragment thereof, optionally wherein the polynucleotide is a cDNA and/or operably linked to a heterologous nucleic acid.

[21b] A polynucleotide encoding a $V_L$ chain of the antibody or DPR-binding fragment thereof of any one of [1] to [20], wherein the $V_L$ chain when paired with a $V_H$ chain comprising the amino acid sequence of SEQ ID NO:12 binds to a DPR of poly-GA having at least 6 repeats as translated from the C9orf72 gene, or a DPR-binding fragment thereof, optionally wherein the polynucleotide is a cDNA and/or operably linked to a heterologous nucleic acid.

[21c] The polynucleotide(s) of any one of [21] to [21b], wherein the heterologous nucleic acid is a regulatory element.

[21d] The polynucleotide(s) of any one of [21] to [21b], wherein the heterologous nucleic acid is a promoter, an enhancer, a ribosome binding site, or a transcription terminator, optionally wherein the promoter is a cytomegalovirus immediate early promoter.

[21e] The polynucleotide(s) of any one of [21] to [21b], wherein the heterologous nucleic acid encodes a secretory signal peptide, optionally wherein the secretory signal peptide is a mammalian signal peptide.

[22] One or more vector(s) comprising the polynucleotide(s) of any one of [21] to [21e].

[23] A host cell comprising the polynucleotide(s) of any one of [21] to [21e] or the vector(s) of [22].

[24] Use of the polynucleotide(s) of any one of [21] to [21e], the vector(s) of [22], or the host cell of [30] for the production of an anti-DPR antibody.

[25] A method for preparing an anti-DPR antibody or immunoglobulin chain(s) thereof, said method comprising
  (a) culturing the cell of [23]; and
  (b) isolating the antibody or immunoglobulin chain(s) thereof from the culture.

[26] An antibody or DPR-binding fragment or immunoglobulin chain(s) thereof encoded by the polynucleotide(s) of any one of [21] to [21e] or obtainable by the method of [25] or the use of [24].

[27] The antibody or DPR-binding fragment thereof of any one of [1] to [20] or [26], which is
  (i) detectably labeled with a label selected from the group consisting of an enzyme, a radioisotope, a fluorophore, tag, flag and a heavy metal; or
  (ii) attached to a drug.

[28] A composition comprising the antibody or DPR-binding fragment thereof of any one of [1] to [20], [26] or [27], the polynucleotide(s) of any one of [21] to [21e], the vector(s) of [22] or the cell of [23].

[29] The composition of [28], which is a pharmaceutical composition and further comprises a pharmaceutically acceptable carrier, optionally wherein the composition is a vaccine.

[30] A method of preparing a pharmaceutical composition for use in the treatment of a disorder associated with or caused by DPR-containing proteins or aggregated forms thereof, the method comprising:
  (a) culturing the cell of [23];
  (b) purifying the antibody or immunoglobulin chain(s) thereof from the culture to pharmaceutical grade; and
  (c) admixing the antibody thereof with a pharmaceutically acceptable carrier

[31] The composition of [28], which is a diagnostic composition or kit, optionally further comprising reagents conventionally used in immuno based diagnostic methods.

[32] An antibody or DPR-binding fragment thereof of any one of [1] to [20], [26] or [27], the polynucleotide(s) of [21], the vector(s) of [22] or the cell of [23] for use in prophylactic treatment of disease associated with or caused by DPR-containing protein or aggregated forms thereof.

[32a] An antibody or DPR-binding fragment thereof of any one of [1] to [20], [26] or [27], the polynucleotide(s) of [21], the vector(s) of [22] or the cell of [23] for use in therapeutic treatment of disease associated with or caused by DPR-containing protein or aggregated forms thereof.

[32b] An antibody or DPR-binding fragment thereof of any one of [1] to [20], [26] or [27], the polynucleotide(s) of [21], the vector(s) of [22] or the cell of [23] for use in prophylactic and therapeutic treatment of disease associated with or caused by DPR-containing protein or aggregate forms thereof.

[33] The antibody or DPR-binding fragment thereof, the polynucleotide(s), the vector(s) or the cell for use according to any one of [32] to [32b], wherein the disease is selected from the group consisting of Frontotemporal lobar degeneration (FTLD), amyotrophic lateral sclerosis (ALS), and FTLD-ALS.

[34] The antibody or DPR-binding fragment thereof, the polynucleotide(s), the vector(s) or the cell for use according to any one of [32] to [32b] and [33], wherein the antibody when administered to a transgenic C9orf72 mouse model is capable of ameliorating at least one symptom of pathological hallmarks of C9orf72 disease such as neuronal loss, behavioral abnormalities, motor deficits and decreased survival.

[35] The antibody or DPR-binding fragment thereof of any one of [1] to [20], [26] or [27] for use in in vivo detection of or targeting a therapeutic and/or diagnostic agent to poly-GA DPR proteins, e.g., aggregated poly-GA DPR proteins, in the human or animal body.

[36] The antibody or DPR-binding fragment thereof for use according to [35], wherein said in vivo imaging comprises positron emission tomography (PET), single photon emission tomography (SPECT), near infrared (NIR), optical imaging or magnetic resonance imaging (MRI).

Furthermore, provided herein is the DPR Ab-1 antibody or a fragment thereof. Also, provided herein is an anti-DPR antibody or fragment thereof comprising complementary determining regions (CDRs), a heavy chain sequence, a light chain sequence, variable domain sequences, and/or constant domain sequences described in Table 12. In embodiments, the anti-DPR antibody or fragment thereof comprises a heavy chain having the amino acid sequence of SEQ ID NO: 38 and a light chain having the amino acid sequence of SEQ ID NO: 42.

Also provided herein is a nucleic acid molecule comprising:
(i) a nucleic acid sequence encoding a heavy chain of an anti-DPR antibody having the amino acid sequence of SEQ ID NO: 38; and/or
(ii) a nucleic acid sequence encoding a light chain of an anti-DPR antibody having the amino acid sequence of SEQ ID NO: 42, optionally wherein the nucleic acid sequences (i) and (ii) are disposed on the same nucleic acid molecule or separate nucleic acid molecules, optionally wherein the nucleic acid molecule comprises a cDNA and/or is operably linked to a heterologous nucleic acid.

Also provided herein is a nucleic acid molecule comprising one or more of the nucleotide sequences of SEQ ID NOs: 51-58.

Also provided herein is a vector comprising a nucleic acid molecule(s) described herein.

Also provided herein is a host cell comprising (i) a nucleic acid molecule(s) described herein or (ii) a vector(s) described herein.

In some aspects, provided herein is a use of a nucleic acid molecule(s), vector(s), or host cell described herein for the production of an anti-DPR antibody or fragment thereof.

In some aspects, provided herein is a method of producing an anti-DPR antibody or fragment thereof comprising: (i) culturing a host cell described herein; and (ii) isolating the antibody or fragment thereof from the culture.

Also provided herein is a composition, e.g., pharmaceutical composition, comprising an anti-DPR antibody or fragment thereof described herein, a nucleic acid molecule(s) described herein, a vector(s) described herein, or a host cell described herein. In embodiments, the pharmaceutical composition comprises a pharmaceutically acceptable carrier. In embodiments, the composition is a diagnostic composition or kit, e.g., further comprising reagents conventionally used in immuno-based diagnostic methods.

Also provided is a method of treating a disorder associated with or caused by DPR-containing protein aggregates, e.g., C9ORF72 DPR-containing protein aggregates (e.g., amyotrophic lateral sclerosis (ALS), frontotemporal lobar degeneration (FTLD), or FTLD-ALS) in a subject in need thereof, comprising administering an anti-DPR antibody or fragment thereof described herein (e.g., DPR Ab-1, e.g., containing the amino acid sequence(s) shown in Table 12) to the subject, thereby treating disorder (e.g., the ALS, FTLD, or FTLD-ALS) in the subject.

Also provided is a method of preparing a pharmaceutical composition for use in the treatment of a disorder associated with or caused by DPR-containing protein or aggregated forms thereof (e.g., ALS, FTLD, or FTLD-ALS), comprising: (i) culturing a host cell described herein; (ii) isolating and/or purifying the antibody or fragment thereof from the culture to pharmaceutical grade; and (iii) mixing the antibody or fragment thereof with a pharmaceutically acceptable carrier.

Provided herein is an anti-DPR antibody or fragment thereof described herein (e.g., DPR Ab-1, e.g., containing the amino acid sequence(s) shown in Table 12), a nucleic acid molecule(s) described herein, a vector described herein, or a host cell described herein, for use in treating (e.g., prophylactically and/or therapeutically treating) a disorder associated with or caused by DPR-containing protein or aggregated forms thereof (e.g., ALS, FTLD, or FTLD-ALS).

Provided herein is the use of an anti-DPR antibody or fragment thereof described herein (e.g., DPR Ab-1, e.g., containing the amino acid sequence(s) shown in Table 12), a nucleic acid molecule(s) described herein, a vector described herein, or a host cell described herein, for the preparation of a medicament for the treatment (e.g., prophylactically and/or therapeutically treating) of a disorder associated with or caused by DPR-containing protein or aggregated forms thereof (e.g., ALS, FTLD, or FTLD-ALS).

Further embodiments of the present invention will be apparent from the description and Examples that follow.

BRIEF DESCRIPTION OF THE DRAWINGS

FIG. 1: Amino acid sequences of the variable regions of human antibody NI-308.5J10 and its variants. Framework (FR) and complementarity determining regions (CDRs) are indicated with the CDRs being underlined. The Kabat numbering scheme was used (cf. www.bioinf.org.uk/abs/; Kabat et al., U.S. Dept. of Health and Human Services, "Sequence of Proteins of Immunological Interest" (1983) referred to in the mentioned web reference and given in Table 1 of WO 2016/050822 A2 at pages 39 and 40, incorporated herein by reference. Unless otherwise specified, references to the numbering of specific amino acid residue positions in an antibody or DPR-binding fragment, variant, or derivative thereof of the present invention are according to the Kabat numbering system, which however is theoretical and may not equally apply to every antibody of the present invention. For example, depending on the position of the first CDR the following CDRs might be shifted in either direction. Accordingly, in case of any inadvertent errors or inconsistencies regarding indication of CDRs in FIG. 1 and/or the sequence listing the person skilled in the art on the basis of the disclosure content of the present application, i.e. the variable heavy (VH) and variable light (VL) chain amino acid sequences of antibody NI-308.5J10 is well in the position to determine the correct CDR sequences in accordance with Kabat, which shall be used for defining the claimed antibody and DPR-binding fragment thereof. (A) variable heavy chain VH and light chain VK sequence of antibody NI-308.5J10 as set forth in SEQ ID NOs: 2 and 7; (B) variable heavy chain sequence VH of antibody NI-308.5J10 variant with amino acid substitution N54S as set forth in SEQ ID NO: 12. Preferred amino acid substitutions within the CDRs of the variable heavy and light chain sequences are indicated in bold including those present in variable heavy chain sequence shown in (c) to (e) and the variable light chain sequence shown in (f). As further explained in the description, within CDRs and/or framework region conservative amino acid substitutions are preferred which take into account the physicochemical properties of the original amino acid either alone or with an adjacent amino acid as illustrated in Mirsky et al., Mol. Biol. Evol. 32 (2014) 806-819 at page 813, FIG. 6 in particular the LG model, for example such that the position of two amino acids is changed, e.g., in VL-CDR3 "PS" with "SP" which has been found in the variable light chain of a human-derived anti-poly GA antibody with similar but not identical binding characteristics, probably because of otherwise more than two amino acid substitutions in one or more of the other CDRs. (C) variable heavy chain sequence VH of antibody NI-308.5J10 variant with amino acid substitution N54T as set forth in SEQ ID NO: 15; (D) variable heavy chain sequence VH of antibody NI-308.5J10 variant with amino acid substitution G55S as set forth in SEQ ID NO: 18; (E) variable heavy chain sequence VH of antibody NI-308.5J10 variant with amino acid substitution G55T as set forth in SEQ ID NO: 21; (F) variable light chain sequence VK of antibody NI-308.5J10 variant with amino acid substitution N75D as set forth in SEQ ID NO: 24.

FIG. 6 discloses SEQ ID NOS: 77, 76, 75, 74, 73, 72 and 71, respectively, in order of appearance.

FIG. 8: Characterization of NI-308.5J10 and a reference human-derived anti-poly-GA DPR antibody (NI-mAb reference) for competitive binding to poly-GA C9orf72 DPR peptides by bio-layer interferometry. Determination of the competitive binding pattern of antibodies NI-308.5J10 and NI-mAb reference for the C9orf72 DPR peptides $(GA)_{15}$ (SEQ ID NO: 66) using bio-layer interferometry. Bio-layer interferometry (BLI) sensorgrams showing the competitive binding of NI-308.5J10 (A) and NI-mAb reference (B) toward immobilized synthetic $(GA)_{15}$ peptides (SEQ ID NO: 66).

FIG. 10: NI-308.5J10 detect pathologic C9orf72 dipeptide repeat protein aggregates in a FTLD patient. (A) Human-derived NI-308.5J10 antibody revealed pathologic neuronal cytoplasmic inclusions, neuronal intranuclear inclusions and dystrophic neurites in the granule cell layer of the cerebellum of a selected C9orf72-FTLD case. In contrast, non-neurological control cerebellum was negative for NI-308.5J10 staining. (B) Representative high magnification images of neuronal C9orf72 DPR inclusions in the granule cell layer of the cerebellum of a selected C9orf72-FTLD case detected by antibody NI-308.5J10.

FIG. 13B: The Fab fragment of DPR Ab-1 bound a GA repeat peptide, as shown by a crystal structure.

DETAILED DESCRIPTION OF THE INVENTION

Figure 2:
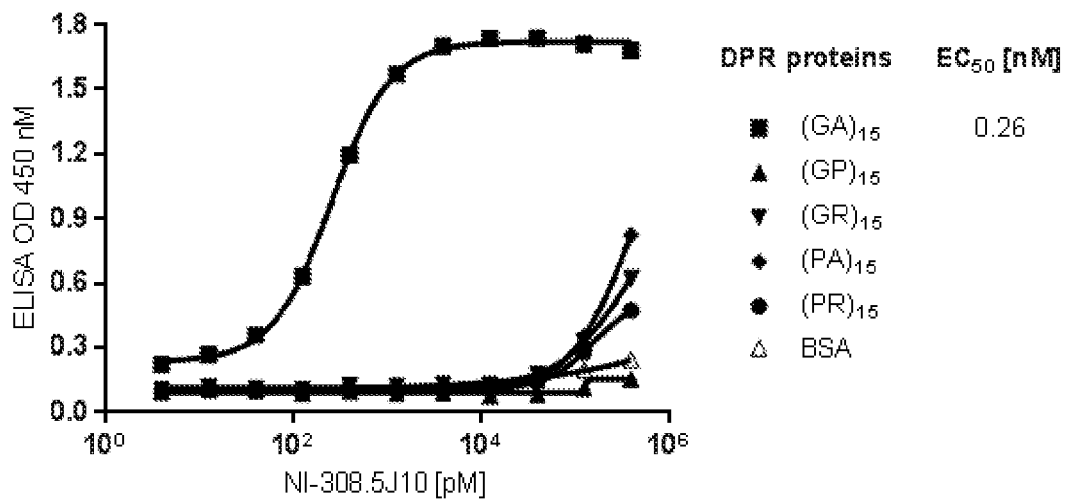
FIG. 2: Binding specificity and $EC_{50}$ determination for C9orf72 dipeptide repeat proteins. $EC_{50}$ of human-derived NI-308.5J10 antibody for C9orf72 dipeptide repeat protein peptides $(GA)_{15}$ (■)(SEQ ID NO: 66), $(GP)_{15}$ (▲)(SEQ ID NO: 67), $(GR)_{15}$ (▼)(SEQ ID NO: 68), $(PA)_{15}$ (♦)(SEQ ID NO: 69), $(PR)_{15}$ (●)(SEQ ID NO: 70) and BSA control (Δ) were determined by indirect ELISA. Antibody NI-308.5J10 specifically recognized the C9orf72 DPR protein peptide $(GA)_{15}$ (SEQ ID NO: 66) with binding affinity of 0.26 nM.
Figure 3:
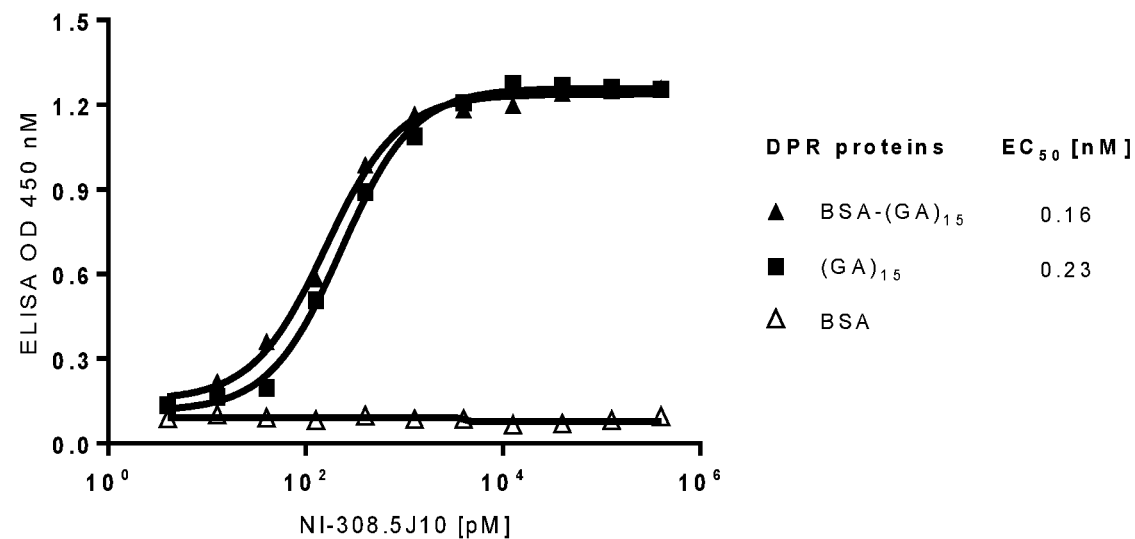
FIG. 3: $EC_{50}$ determination for BSA-coupled and uncoupled C9orf72 dipeptide repeat protein peptides. Determination of the half maximal effective concentration ($EC_{50}$) of human-derived NI-308.5J10 antibody for BSA-coupled (▲) and uncoupled (■) C9orf72 dipeptide repeat protein peptides $(GA)_{15}$ (SEQ ID NO: 66), $(GP)_{15}$ (SEQ ID NO: 67), $(GR)_{15}$ (SEQ ID NO: 68), $(PR)_{15}$ (SEQ ID NO: 69), $(PA)_{15}$ (SEQ ID NO: 70) or BSA control (Δ), using indirect ELISA. Antibody NI-308.5J10 recognized with similar binding affinities BSA-coupled (0.16 nM) and uncoupled (0.23 nM) C9orf72 DPR protein peptides.

The present invention generally relates to immunotherapy and non-invasive methods for the detection of diseases and conditions associated with the presence of dipeptide repeats (DPR) proteins and in particular aggregated forms thereof. More specifically, the present invention relates to recombinant human-derived monoclonal antibodies and DPR-binding fragments thereof, which have been generated based on sequence information obtained from selected human donor populations and are capable of binding to such DPRs, in particular poly-glycine-alanine (Gly-Ala; GA)-DPRs and proteins containing such DPRs. The recombinant human-derived monoclonal antibodies of the present invention as well as synthetic and biotechnological derivatives thereof are advantageously characterized by specifically binding to altered C9orf72 with expanded hexanucleotide repeats forming C9orf72-dipeptide repeats (DPRs). As shown in the Examples, the recombinant antibodies of the present invention are highly specific as a diagnostic reagent for the detection of DPRs and/or pathological C9orf72 without giving false positives and due to the human origin of the sequences encoding at least the variable region and CDRs, respectively, and maturation of the original antibodies in the human body can be reasonably expected to be efficacious and safe as therapeutic agent.

I. Definitions

Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Furthermore, unless stated otherwise, terms and expressions used herein in order to characterize the present invention are given the definitions as provided in WO 2016/050822 A2, in particular in subsection "I. Definitions" at pages 26 to 53, including Table 1 for the CDR Definitions at pages 39 and 40, the disclosure content of which is explicitly incorporated herein by reference. The same applies to the general embodiments disclosed in WO 2016/050822 A2 for antibodies, polynucleotides, etc.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

If not specifically indicated otherwise, the term "DPR", i.e. "dipeptide repeat" proteins, is used hereinto specifically refer to repeating units of two amino acids, in particular due to an expanded hexanucleotide repeat in a gene. The term "DPR" and "DPRs" is also used to refer collectively to all types and forms of DPRs, such as GA, GR, GP, PA, PR etc. In the following, the present invention will mainly be described with respect to antibodies specifically recognizing DPRs comprising or consisting of either GA, e.g., (GA)n (where n is 1, 2, 3, 4, 5, 6, or greater (e.g., 1, 2, 3, 4, 5, 6, 7, 8, 9, 10, 11, 12, 13, 14, 15, or greater), e.g., where n is between 6 and 15, inclusive of 6 and 15, e.g., where n is 15), for example with 15 repeats ($GA_{15}$) (SEQ ID NO: 66), GP, for example with 15 repeats ($GP_{15}$) (SEQ ID NO: 67), GR, for example with 15 repeats ($GR_{15}$) (SEQ ID NO: 68), or PR, for example with 15 repeats ($PR_{15}$) (SEQ ID NO: 70), or PA, for example with 15 repeats ($PA_{15}$) (SEQ ID NO: 69) commonly observed in C9ORF72-DPR proteins found in brain tissue of patients suffering from FLTD or ALS. In embodiments, the anti-DPR antibody described herein binds specifically to a DPR comprising a GA repeat. Though anti-C9ORF72-DPR antibodies represent a preferred embodiment, the present invention generally provides anti-DPR protein antibodies and corresponding embodiments. Accordingly, it is emphasized that in principle any embodiment and corresponding features disclosed herein and illustrated in the Examples and Figures, unless specifically applicable to the anti-C9ORF72-DPR only, is also meant to apply to any anti-DPR protein antibody in general.

Another example for a DPR related disease is spinocerebellar ataxia type 36, a slowly progressive neurodegenerative disorder and a subtype of the autosomal dominant cerebellar ataxia type 1 (ADCA type 1) characterized by adult-onset gait and limb ataxia, lower limb spasticity, dysarthria, muscle fasiculations, tongue atrophy and hyperreflexia. Some affected individuals can also develop hearing loss; see, e.g., Garcia-Murias et al., Brain 135 (2012), 1423-1435. It was shown that spinocerebellar ataxia type 36 is caused by a heterozygous expansion of the intronic GGCCTG hexanucleotide repeat in the NOP56 gene on chromosome 20p13; see, e.g., Garcia-Murias et al., Brain 135 (2012), 1423-1435. Ikeda et al., Neurology 79 (2012), 333-341, Kobayashi et al., Am. J. Hum. Genet. 89 (2011), 121-130.

The term "C9ORF72", if not specifically indicated otherwise, refers to the altered forms of chromosome 9 open reading frame 72 (C9ORF72). The term "C9ORF72" is also used to generally identify C9ORF72 hexanucleotide expansions, leading to C9ORF72-dipeptide repeats (DPRs). Therefore, the term is also used to indicate C9ORF72-DPRs. The term "C9ORF72" is also used to refer collectively to all types and forms of C9ORF72, such as mutated C9ORF72. Added letters in front of the terms C9ORF72 are used to indicate the organism the particular ortholog is originating from, e.g. hC9ORF72 for human C9ORF72 or mC9ORF72 for murine origin.

The anti-DPR antibodies disclosed herein optionally bind C9ORF72-dipeptide repeats (DPRs) and epitopes thereof. For example, disclosed herein are antibodies that specifically bind pathologically altered C9ORF72 species or fragments thereof, i.e. dipeptide repeats that are unconventionally translated from C9ORF72 transcripts of the expanded intronic C9ORF72 hexanucleotide repeats, as well as aggregated forms of C9ORF72-DPRs or fragments thereof. The term (pathologically) aggregated/aggregates of C9ORF72-DPRs is used herein to specifically refer to the aforementioned forms. The term (pathological) "aggregated forms" or "aggregates" as used herein describes the products of an accumulation or cluster formation due to C9ORF72 erroneous/pathological translation from C9ORF72 transcripts of the expanded intronic C9ORF72 hexanucleotide repeats. These aggregates, accumulations or cluster forms may be, substantially consist or consist of both C9ORF72-DPR protein and/or fragments thereof. As used herein, reference to an antibody that "specifically binds", "selectively binds", or "preferentially binds" C9ORF72-DPRs refers to an antibody that does not bind other unrelated proteins. The antibodies of the present invention do not substantially recognize unrelated amyloid-forming proteins selected from the group consisting of paired helical filament (PHF)-tau, TAU, transactive response DNA binding protein 43 (TDP-43), transthyrethin (TTR), full-length amyloid precursor protein (flAPP), and/or Huntingtin (HTT). In one example, a C9ORF72-DPR antibody disclosed herein can bind DPRs and/or C9ORF72-DPRs or an epitope thereof and shows no binding above about 2 times background for other proteins.

An antibody that "specifically binds" or "selectively binds" a DPR and/or a C9ORF72-DPR protein variant refers to an antibody that does not bind all variants of C9ORF72-DPR proteins, i.e., does not bind at least one other C9ORF72 conformer. For example, disclosed herein are antibodies that can preferentially bind to forms of C9ORF72 showing expanded hexanucleotide repeats forming DPRs both in vitro and in tissues obtained from patients with diseases associated with C9ORF72 or with a risk to develop diseases associated with C9ORF72.

The term "peptide" is understood to include the terms "polypeptide" and "protein" (which, at times, may be used interchangeably herein) within its meaning. Similarly, fragments of proteins and polypeptides are also contemplated and may be referred to herein as "peptides". Nevertheless, the term "peptide" optionally denotes an amino acid polymer including at least 5 contiguous amino acids, for example, at least 10 contiguous amino acids, for example, at least 15 contiguous amino acids, for example, at least 20 contiguous amino acids, for example, at least 25 contiguous amino acids. In addition, the peptide in accordance with present invention typically has no more than 100 contiguous amino acids, for example, less than 80 contiguous amino acids or less than 50 contiguous amino acids.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation and derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

"Recombinant peptides, polypeptides or proteins" refer to peptides, polypeptides or proteins produced by recombinant DNA techniques, i.e. produced from cells, microbial or mammalian, transformed by an exogenous recombinant DNA expression construct encoding the fusion protein including the desired peptide. Proteins or peptides expressed in most bacterial cultures will typically be free of glycan. Proteins or polypeptides expressed in yeast may have a glycosylation pattern different from that expressed in mammalian cells.

Included as polypeptides of the present invention are fragments, derivatives, analogs or variants of the foregoing polypeptides as well as synthetic or biological variants and any combinations thereof. The terms "fragment," "variant," "derivative", and "analog" include peptides and polypeptides having an amino acid sequence sufficiently similar to the amino acid sequence of the natural peptide. The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Optionally, variants will be sufficiently similar to the amino acid sequence of the preferred peptides of the present invention, in particular to altered C9ORF72 protein, such as pathological C9ORF72-DPRs as well as DPR proteins alone, variants, derivatives or analogs of either of them. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

Furthermore, the terms "fragment," "variant," "derivative", and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of DPR protein specific binding molecules, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Determination of Similarity and/or Identity of Molecules:

"Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

"Similarity" between two polynucleotides is determined by comparing the nucleic acid sequence of one polynucleotide to the sequence of a polynucleotide. A nucleic acid of one polynucleotide is similar to the corresponding nucleic acid of a second polynucleotide if it is identical or, if the nucleic acid is part of a coding sequence, the respective triplet comprising the nucleic acid encodes for the same amino acid or for a conservative amino acid substitution. The determination of percent identity or similarity between two sequences is optionally accomplished using the mathematical algorithm of Karlin and Altschul (1993) Proc. Natl. Acad. Sci USA 90:5873-5877. Such an algorithm is incorporated into the BLASTn and BLASTp programs of Altschul et al. (1990) J. Mol. Biol. 215:403-410 available at NCBI (www.ncbi.nlm.nih.gov/Blast.cge).

The determination of percent identity or similarity is performed with the standard parameters of the BLASTn programs for BLAST polynucleotide searches and BLASTp programs for BLAST protein search, as recommended on the NCBI webpage and in the "BLAST Program Selection Guide" in respect of sequences of a specific length and composition.

BLAST polynucleotide searches are performed with the BLASTn program.

For the general parameters, the "Max Target Sequences" box may be set to 100, the "Short queries" box may be ticked, the "Expect threshold" box may be set to 1000 and the "Word Size" box may be set to 7 as recommended for short sequences (less than 20 bases) on the NCBI webpage. For longer sequences the "Expect threshold" box may be set to 10 and the "Word Size" box may be set to 11. For the scoring parameters the "Match/mismatch Scores" may be set to 1, −2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "DUST Filter Settings" may be ticked and the "Mask lower case letters" box may not be ticked. In general the "Search for short nearly exact matches" may be used in this respect, which provides most of the above indicated settings. Further information in this respect may be found in the "BLAST Program Selection Guide" published on the NCBI webpage.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension: 1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

Modifications of both programs, e.g., in respect of the length of the searched sequences, are performed according to the recommendations in the "BLAST Program Selection Guide" published in a HTML and a PDF version on the NCBI webpage.

Polynucleotides:

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operable associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operable associated" or "operable linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operable associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operable associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operable associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "binding molecule" as used in the context of the present invention relates primarily to antibodies, and fragments thereof, but may also refer to other non-antibody molecules that bind dipeptide repeat (DPR) proteins, optionally which bind to altered C9ORF72, in particular (pathologically) altered C9ORF72-DPRs, including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

Antibodies:

The terms "antibody" and "immunoglobulin" are used interchangeably herein. An antibody or immunoglobulin is a binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma, \mu, \alpha, \delta, \epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to DPRs, in particular to altered C9ORF72 forming C9ORF72-DPRs is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE 1

| CDR Definitions[1] | | |
|---|---|---|
| | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply to every antibody of the present invention. For example, depending on the position of the first CDR the following CDRs might be shifted in either direction.

Antibodies or fragments thereof (e.g., antigen-binding fragments or immunospecific fragments), variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity. In a particularly preferred embodiment, the antibody of the present invention is not a polyclonal antibody, i.e. it substantially consists of one particular antibody species rather than being a mixture obtained from a plasma immunoglobulin sample.

Antibody fragments, including single-chain antibodies, may comprise the variable region(s) alone or in combination with the entirety or a portion of the following: hinge region, CH1, CH2, and CH3 domains. Also included in the invention are DPR binding fragments which comprise any combination of variable region(s) with a hinge region, CH1, CH2, and CH3 domains. Antibodies or immunospecific fragments thereof of the present invention may be from any animal origin including birds and mammals. Optionally, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain portion" or "heavy chain" or "heavy chain region" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" or "light chain" or "light chain region" includes amino acid sequences derived from an immunoglobulin light chain. Optionally, the light chain portion comprises at least one of a $V_L$ or CL domain.

The minimum size of a peptide or polypeptide epitope for an antibody is thought to be about four to five amino acids. Peptide or polypeptide epitopes optionally contain at least seven, optionally at least nine, or optionally between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, optionally at least 8, at least 9, at least 10, at least 15, at least 20, at least 25, or between about 15 to about 30 contiguous or non-contiguous amino acids of DPRs such as $GA_{15}$ (SEQ ID NO: 66) as found in C9ORF72-DPRs. Put in other words, the antibody of the present invention or biotechnological derivative thereof optionally recognizes a DPR with a repeat number of the dipeptide consisting of two different amino acids X and X' (XXX and XXX'; XaaXaa') of for example 3 to 50, optionally 10 to 40, optionally 15 to 30, or optionally 15. Thus, the epitope or antigen recognized by the antibody of the present invention or biotechnological derivative thereof if consisting of a DPR with a repeat number of 15 generally may be designated $(XX')_{15}$.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant (KD) that is less than the antibody's KD for the second epitope. In another non-limiting example, an antibody may be considered to bind a first antigen preferentially if it binds the first epitope with an affinity that is at least one order of magnitude less than the antibody's KD for the second epitope. In another non-limiting example, an antibody may be considered to bind a first epitope preferentially if it binds the first epitope with an affinity that is at least two orders of magnitude less than the antibody's KD for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind DPRs or a fragment, variant or specific conformation thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. Optionally, an antibody of the invention may be said to bind DPR proteins or a fragment, variant or specific conformation thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$. In a particularly preferred embodiment, the DPR is a DPR associated with C9ORF72, i.e. C9ORF72-DPR.

A binding molecule, e.g., an antibody or antigen-binding fragment, variant, or derivative disclosed herein may be said to bind DPR, or a fragment, variant or specific conformation thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. Optionally, an antibody of the invention may be said to bind DPR or a fragment, variant or specific conformation thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$. In one embodiment, the binding molecule may be said to bind C9ORF72-DPR, or a fragment, variant or specific conformation thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. Optionally, an antibody of the invention may be said to bind C9ORF72-DPR or a fragment, variant or specific conformation thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valences of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., KD, IC$_{50}$, are optionally made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to DPRs and/or mutated C9ORF72 species showing C9ORF72-DPRs and/or fragments thereof. Preferred binding affinities include those with a dissociation constant or Kd less than $5\times10^{-2}$ M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$ M, $10^{-6}$M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains; see Roux et al., J. Immunol. 161 (1998), 4083-4090.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, peritoneal fluid, CSF, saliva or urine. In other aspects, a sample can comprise whole blood, blood plasma, blood serum, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art.

Diseases:

Unless stated otherwise, the terms "disorder" and "disease" are used interchangeably herein and comprise any undesired physiological change in a subject, an animal, an isolated organ, tissue or cell/cell culture.

Frontotemporal lobar degeneration (FTLD) is a pathogenesis associated with an atrophy in the frontal lobe and temporal lobe of the brain. Additionally 50% of FTLD patient were also shown to have a positive family history and compared to amyotrophic lateral sclerosis (ALS). As already described above, the shared underlying cause of pathogenesis seems to be a heterozygous expanded hexanucleotide repeat located in the C9ORF72 of FTLD and ALS patients. In particular, it was shown that resulting repeating units of two amino acids (dipeptide repeats, DPRs).

However, expanded hexanucleotide repeats resulting in the repetition of two amino acids (DPRs) have also been reported in several other diseases and/or disorders. The diseases including but are not limited to Frontotemporal lobar degeneration (FTLD), amyotrophic lateral sclerosis (ALS), FTLD-ALS, and/or spinocerebellar ataxia type 36, and symptoms associated therein.

In one embodiment of the present invention the antibodies of the present invention, binding molecules having substantially the same binding specificities of any one thereof, the polynucleotides, the vectors or the cells of the present invention are used for preparation of a pharmaceutical or diagnostic composition for prophylactic and/or therapeutic treatment of diseases associated with DPRs, for monitoring disease progression and/or treatment response, and for the diagnosis of diseases associated with DPRs amyloidosis comprising Frontotemporal lobar degeneration (FTLD), amyotrophic lateral sclerosis (ALS), FTLD-ALS, and/or spinocerebellar ataxia type 36.

In some embodiments, the antibodies of the present invention bind to pathologic C9ORF72-dipeptide repeat protein or aggregated forms thereof in FTLD patients. Therefore, in a one embodiment of the present invention the antibodies, binding molecules having substantially the same binding specificities of any one thereof, the polynucleotides, the vectors or the cells of the present invention are used for preparation of a pharmaceutical or diagnostic composition for prophylactic and/or therapeutic treatment of diseases associated with C9ORF72-DPRs, for monitoring disease progression and/or treatment response, and for the diagnosis of diseases associated with C9ORF72-DPRs or aggregated forms thereof comprising Frontotemporal lobar degeneration (FTLD), amyotrophic lateral sclerosis (ALS), and/or FTLD-ALS, and symptoms associated therein.

Treatment:

As used herein, the terms "treat" or "treatment" refer to both therapeutic treatment and prophylactic or preventative measures, wherein the object is to prevent or slow down (lessen) an undesired physiological change or disorder, such as the development of cardiac deficiency. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

If not stated otherwise the term "drug," "medicine," or "medicament" are used interchangeably herein and shall include but are not limited to all (A) articles, medicines and preparations for internal or external use, and any substance or mixture of substances intended to be used for diagnosis, cure, mitigation, treatment, or prevention of disease of either man or other animals; and (B) articles, medicines and preparations (other than food) intended to affect the structure or any function of the body of man or other animals; and (C) articles intended for use as a component of any article specified in clause (A) and (B). The term "drug," "medicine," or "medicament" shall include the complete formula of the preparation intended for use in either man or other animals containing one or more "agents," "compounds", "substances" or "(chemical) compositions" as and in some other context also other pharmaceutically inactive excipients as fillers, disintegrants, lubricants, glidants, binders or ensuring easy transport, disintegration, disaggregation, dissolution and biological availability of the "drug," "medicine," or "medicament" at an intended target location within the body of man or other animals, e.g., at the skin, in the stomach or the intestine. The terms "agent," "compound", or "substance" are used interchangeably herein and shall include, in a more particular context, but are not limited to all pharmacologically active agents, i.e. agents that induce a desired biological or pharmacological effect or are investigated or tested for the capability of inducing such a possible pharmacological effect by the methods of the present invention.

By "subject" or "individual" or "animal" or "patient" or "mammal," is meant any subject, particularly a mammalian subject, e.g., a human patient, for whom diagnosis, prognosis, prevention, or therapy is desired.

Pharmaceutical Carriers:

Pharmaceutically acceptable carriers and administration routes can be taken from corresponding literature known to the person skilled in the art. The pharmaceutical compositions of the present invention can be formulated according to methods well known in the art; see for example Remington: The Science and Practice of Pharmacy (2000) by the University of Sciences in Philadelphia, ISBN 0-683-306472, Vaccine Protocols 2nd Edition by Robinson et al., Humana Press, Totowa, New Jersey, USA, 2003; Banga, Therapeutic Peptides and Proteins: Formulation, Processing, and Delivery Systems. 2nd Edition by Taylor and Francis. (2006), ISBN: 0-8493-1630-8. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. Aerosol formulations such as nasal spray formulations include purified aqueous or other solutions of the active agent with preservative agents and isotonic agents. Such formulations are optionally adjusted to a pH and isotonic state compatible with the nasal mucous membranes. Pharmaceutical compositions for oral administration, such as single domain antibody molecules (e.g., "Nanobodies™") etc. are also envisaged in the present invention. Such oral formulations may be in tablet, capsule, powder, liquid or semi-solid form. A tablet may comprise a solid carrier, such as gelatin or an adjuvant. Formulations for rectal or vaginal administration may be presented as a suppository with a suitable carrier; see also O'Hagan et al., Nature Reviews, Drug Discovery 2(9) (2003), 727-735. Further guidance regarding formulations that are suitable for various types of administration can be found in Remington's Pharmaceutical Sciences, Mace Publishing Company, Philadelphia, PA, 17th ed. (1985) and corresponding updates. For a brief review of methods for drug delivery see Langer, Science 249 (1990), 1527-1533.

II. Antibodies of the Present Invention

The present invention generally relates to anti-DPR, optionally anti-C9orf72-DPR antibodies and DPR-binding, i.e. DPR-binding fragments as well as biotechnological variants and derivatives thereof which optionally demonstrate the immunological binding characteristics and/or biological properties as outlined for the antibodies described herein, e.g., illustrated in the Examples. In some embodiments, the anti-DPR antibody is a human or human-derived antibody. In some embodiments, the anti-DPR antibody is a human monoclonal antibody. In some embodiments, the anti-DPR antibody is a human-derived monoclonal antibody. In accordance with the present invention a human monoclonal antibody specific for poly-GA DPRs has been cloned from a pool of healthy human subjects. In the course of the experiments performed in accordance with the present invention, recombinant IgG antibody derived from the original auto-antibody has been evaluated for its capacity to bind to DPRs and to other proteins including bovine serum albumin (BSA); see Examples 3 to 9 as well as FIGS. 2 to 8. As mentioned, the subject antibody could be shown to bind DPR protein or aggregated forms thereof in brain tissue derived from selected human C9orf72-FTLD patients; see Example 11 and FIG. 10. Moreover, as demonstrated in Example 9 and FIG. 8, the subject antibody's binding to aggregated C9orf72 poly-GA DPR $(GA)_{15}$ (SEQ ID NO: 66) is not blocked by prior binding to the target by a reference anti-poly GA antibody (NI-mAb reference) pointing to ability of the antibody to recognize a conformational epitope on poly-GA DPR aggregates, which may also be accessible in co-aggregates with other DPR proteins and/or amyloidogenic proteins.

Furthermore, the anti-DPR antibody, DPR-binding fragment, synthetic or biotechnological derivative or variant thereof can be optimized to have improved pharmacokinetic, manufacturability and stability properties. Therefore, at least one amino acid in the CDR or variable region, which is prone to modifications selected from the group consisting of glycosylation, oxidation, deamination, peptide bond cleavage, iso-aspartate formation and/or unpaired cysteine is substituted by a mutated amino acid that lack such alteration or wherein at least one carbohydrate moiety is deleted or added chemically or enzymatically to the antibody, see, e.g. Liu et al., J. Pharm. Sci. 97(7) (2008), 2426-2447; Beck et al., Nat. Rev. Immunol. 10 (2010), 345-352; Haberger et al., MAbs. 6 (2014), 327-339.

Figure 11:
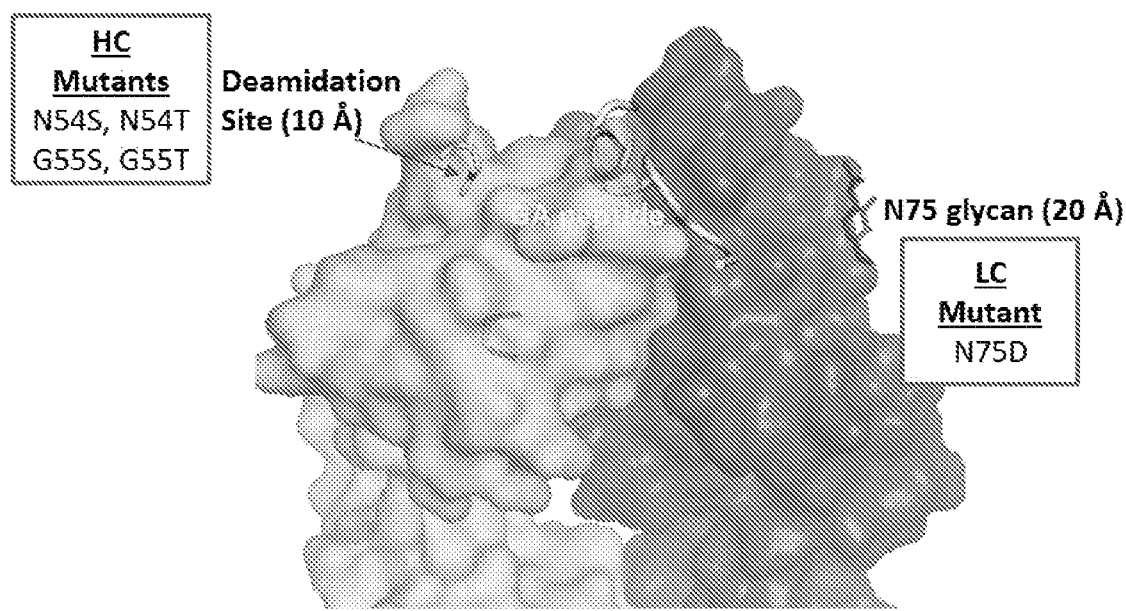
FIG. 11: Crystal structure of the NI-308.5J10 antibody into which the mutations N54S, N54T, G55S, G55T and N75D have been mapped. As can be derived from the crystal structure, the post translational modifications are far away from the binding site of the antibody.
Figure 12:
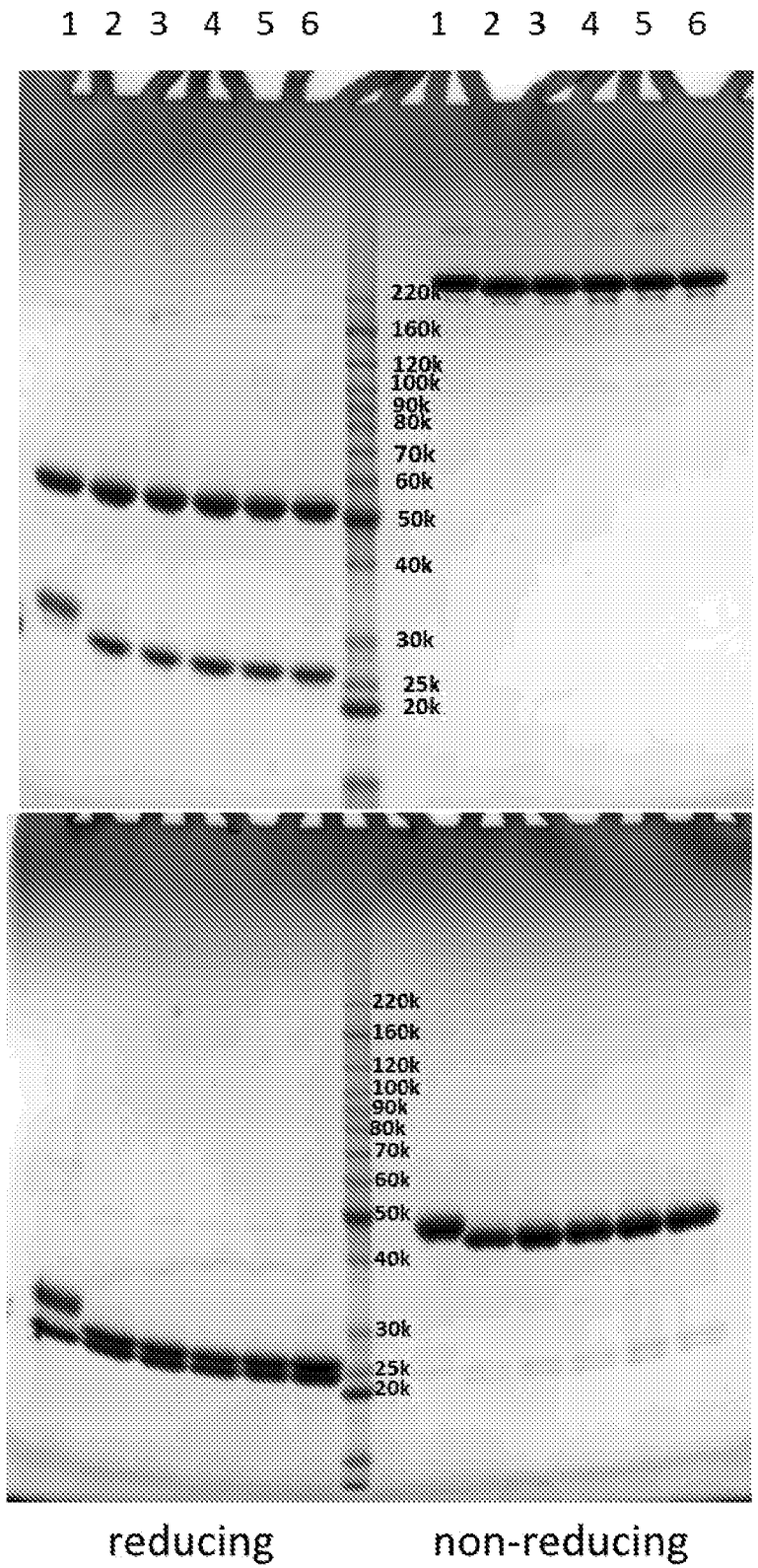
FIG. 12: Integrity analysis of NI-308.5J10 antibody variants. Engineered NI-308.5J10 antibody variants consisting of N75D light chain in combination with each of the heavy chain mutants were produced as full human IgG1 and also as a Fabs. Purified proteins were analyzed for size and homogeneity by SDS-PAGE, upper: human IgG1: lane 1, NI-308.5J10 WT/WT; lane 2, NI-308.5J10 variant WT/N75D; lane 3, NI-308.5J10 variant N54S/N75D; lane 4, NI-308.5J10 variant N54T/N75D; lane 5, NI-308.5J10 variant G55S/N75D; lane 6, NI-308.5J10 variant G55T/N75D; lower: his-tagged Fabs: lane 1, WT-Fab-6His/WT NI-308.5J10; lane 2, NI-308.5J10 variant WT-Fab-6His/N75D; lane 3, NI-308.5J10 variant N54S-Fab-6His/N75D; lane 4, NI-308.5J10 variant N54T-Fab-6His/N75D; lane 5, NI-308.5J10 variant G55S-Fab-6His/N75D; lane 6, NI-308.5J10 variant G55T-Fab-6His/N75D. All proteins showed the expected size with no apparent aggregates or proteolysis products.
Figure 13A:
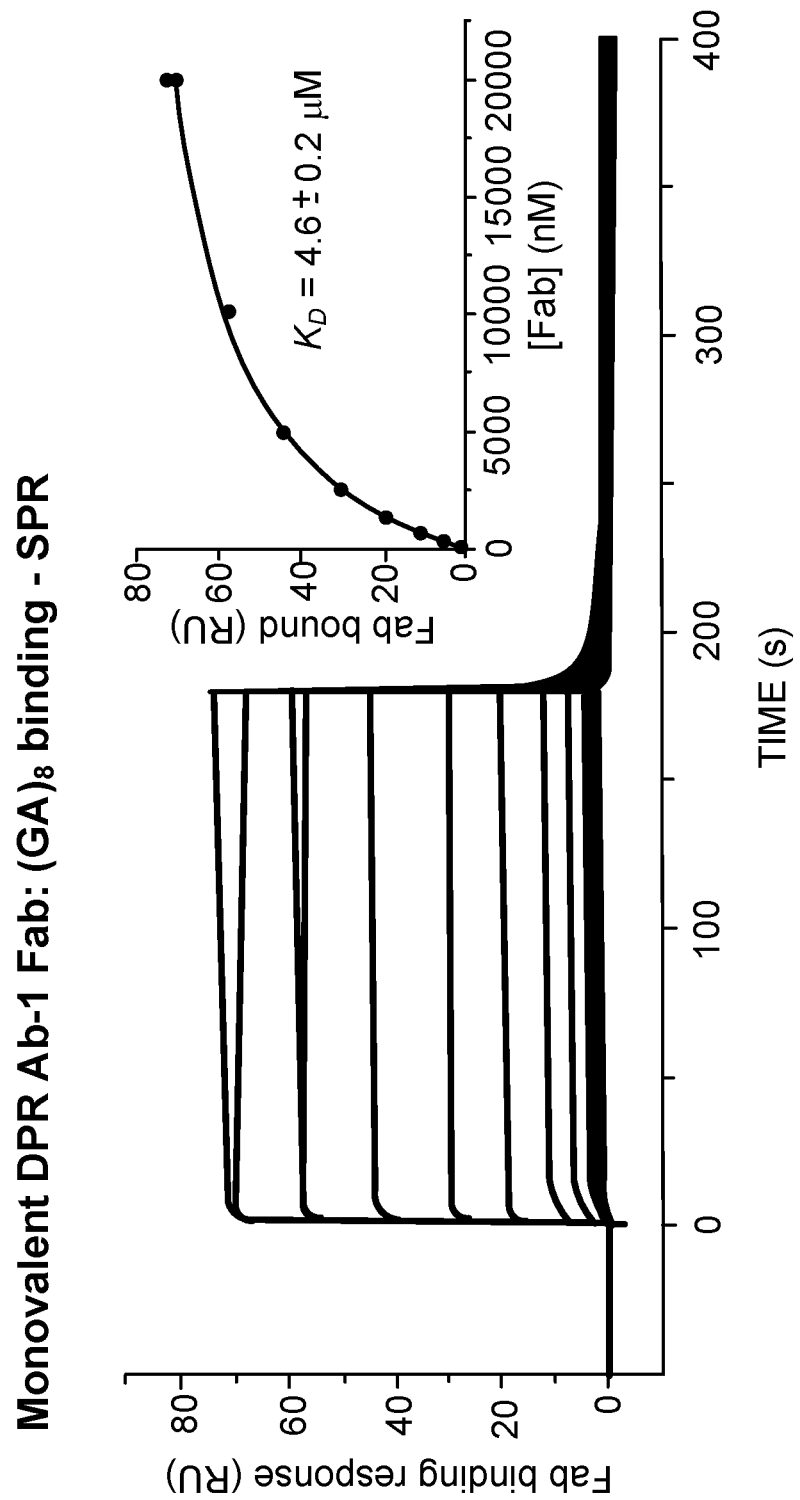
FIG. 13A: DPR Ab-1 Fab binding to GA (e.g., poly(GA). The Fab fragment of DPR Ab-1 bound $(GA)_8$ repeats (SEQ ID NO: 81), as shown by surface plasmon resonance.

In order to investigate amino acid substitutions which could possibly render the original antibody more stable and/or improving manufacturability while keeping the essential binding characteristics of the parent subject antibody, the crystal structure of a Fab fragment of the subject NI-308.5J10 antibody with a poly-$(GA)_8$ peptide (SEQ ID NO: 81) had been prepared and analyzed; see Examples 12 to 16 and FIGS. 11 and 12. For monitoring the binding affinity of the different variants of the original NI-308.5J10 antibody, Fab fragments were generated and tested to quantify the intrinsic monovalent affinities, without complications from multivalent interactions. Since the modified Fab fragments substantially retained the affinity of the Fab fragment of the parent antibody, the corresponding full IgG antibodies are expected to have substantially the same binding affinity as the parent antibody for poly-$(GA)_{15}$ peptide (SEQ ID NO: 66); see item [14] and the appended Examples.

Thus, the present invention generally relates to recombinant human-derived monoclonal anti-DPR antibodies and DPR-binding fragments, synthetic and biotechnological derivatives and variants thereof wherein the antibody or DPR-binding fragment thereof comprises in its variable region the following six complementarity determining regions (CDRs):
  (a) VH-CDR1 comprising the amino acid sequence of SEQ ID NO: 3 (e.g., comprises SEQ ID NO:78) or a variant thereof, wherein the variant comprises one or two amino acid substitutions,
  (b) VH-CDR2 comprising the amino acid sequence of SEQ ID NO: 4 or a variant thereof, wherein the variant comprises one or two amino acid substitutions,
  (c) VH-CDR3 comprising the amino acid sequence of SEQ ID NO: 5 or a variant thereof, wherein the variant comprises one or two amino acid substitutions,
  (d) VL-CDR1 comprising the amino acid sequence of SEQ ID NO: 8 or a variant thereof, wherein the variant comprises one or two amino acid substitutions,
  (e) VL-CDR2 comprising the amino acid sequence of SEQ ID NO: 9 or a variant thereof, wherein the variant comprises one or two amino acid substitutions,
  (f) VL-CDR3 comprising the amino acid sequence of SEQ ID NO: 10 or a variant thereof, wherein the variant comprises one or two amino acid substitutions;
wherein the antibody or DPR-binding thereof display any one of the properties illustrated for the subject NI-308.5J10 antibody and specific variants thereof in the appended Examples and Figures, optionally wherein the antibody or DPR-binding thereof has one or more of the properties as summarized in items [1] to [36], optionally in combination as indicated by the dependency of the items from each other. For example, in one embodiment the antibody or DPR-binding thereof is capable of binding a dipeptide repeat (DPR) of poly-glycine-alanine (GA) having at least 6 repeats $(GA)_6$ (SEQ ID NO: 80) as translated from the chromosome 9 open reading frame 72 (C9orf72) gene. The synthetic or biotechnological derivative or variant of the subject NI-308.5J10 may contain one, two, three, four, five or six variant CDRs as specified herein. For example, the synthetic or biotechnological derivative or variant antibody or DPR-binding thereof may contain three, optionally two, or optionally only one variant VH-CDR while the VL-CDRs remain unchanged or only one VL-CDR represents a variant vice versa. In addition, or alternatively, the antibody or DPR-binding fragment thereof of the present invention comprises in its variable region
  (a) a variable heavy ($V_H$) chain comprising the amino acid sequence depicted in SEQ ID NO: 2 or a variant thereof, wherein the variant comprises one or more amino acid substitutions; and
  (b) a variable light ($V_L$) chain comprising the amino acid sequence depicted in SEQ ID NO: 7, or a variant thereof, wherein the variant comprises one or more amino acid substitutions; optionally wherein
    the $V_H$ and $V_L$ chain amino acid sequence is at least 90% identical to SEQ ID NO: 2 and 7, respectively.
Preferred criteria for selecting appropriate amino acids for substitutions and positions within the CDRs are shown in FIG. 1 and explained in the figure legend to FIG. 1, supra.

As illustrated in Example 12 to 16, post translational modifications of the NI-308.5J10 hIgG1 antibody have been identified, i.e. light chain glycosylation and heavy chain Asn54 deamidation, which have been removed by corresponding amino substitutions. Thus, in one embodiment of the antibody or DPR-binding fragment thereof of the present invention, the CDRs do not contain a deamidation-prone asparagine (N) and/or glutamine (Q) and/or the $V_H$ and/or $V_L$ chain amino acid sequences do not contain an occupied glycosylation site. In one embodiment, one or more glycosylation site(s) in the $V_H$ and/or $V_L$ chain amino acid sequences has been mutated to be incapable of being an occupied glycosylation site.

In a preferred embodiment, the one, two or more amino acid substitutions in the antibody or DPR-binding fragment thereof are selected from
  (a) substitution of a deamidation-prone asparagine (N) or glutamine (Q) with a non-deamidation-prone amino acid;
  (b) substitution of a small, flexible amino acid being directly adjacent to a deamidation-prone N or Q with a larger amino acid, optionally wherein the adjacent amino acid is glycine (G);
  (c) substitution of at least one amino acid which leads to removal of a glycosylation site, optionally wherein the at least one amino acid is within the glycosylation motif NXS or NXT; and/or
  (d) substitution of one or more amino acids which are conservative amino acid substitutions; optionally, wherein the amino acid substitution(s) of (a) and (b) are present in VH-CDR2 and the amino acid substitution(s) of (c) are present in the $V_L$ chain.

Also here in case of aiming at improving the stability and manufacturability of the subject antibody and DPR-binding fragments thereof, respectively, the amino acids used for substitution are optionally selected according to above mentioned considerations. Optionally, in accordance with the Examples in VH-CDR2 the asparagine (N) corresponding to position 54 and/or the glycine (G) corresponding to position 55 of SEQ ID NO: 2 are substituted with another amino acid, optionally wherein the asparagine (N) is substituted with serine (S) or threonine (T) and/or wherein the glycine (G) is substituted with serine (S) or threonine (T); and/or in the $V_L$ chain the asparagine (N) corresponding to position 75 of SEQ ID NO: 7 is substituted with another amino acid, optionally wherein the asparagine (N) is substituted with aspartic acid (D).

Figure 6:
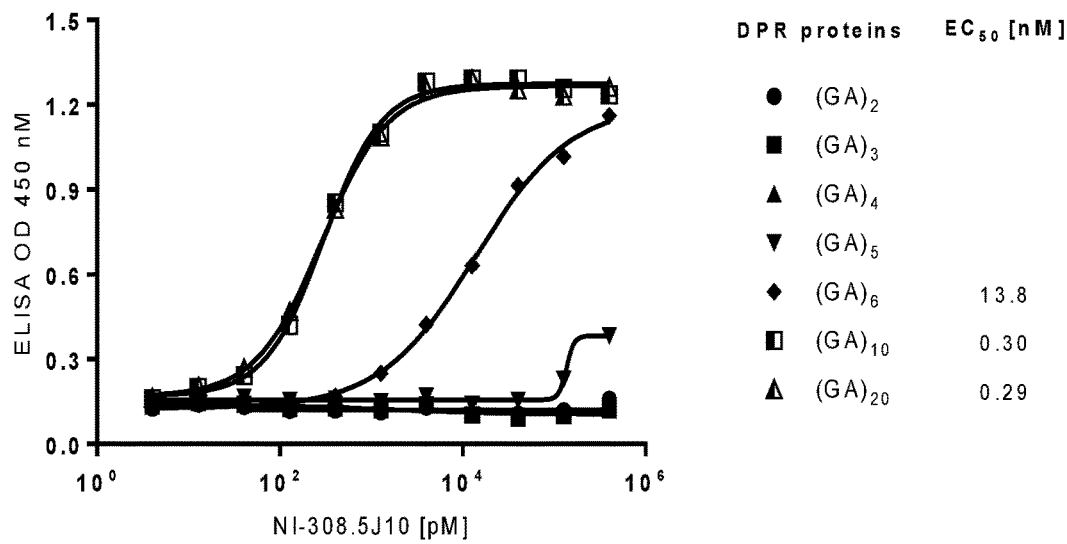
FIG. 6: C9orf72 DPR proteins repeat-length dependent binding of antibody NI-308.5J10. Determination of dipeptide repeat-length dependent binding specificity and the half maximal effective concentration ($EC_{50}$) of human-derived NI-308.5J10 antibody for C9orf72 poly-GA dipeptide repeat protein peptides by indirect ELISA. Antibody NI-308.5J10 targeted the DPR protein peptides $(GA)_{6}$ (SEQ ID NO: 80), $(GA)_{10}$ (SEQ ID NO: 79) and $(GA)_{20}$ (SEQ ID NO: 82) with binding affinity at $EC_{50}$ of 13.8 nM, 0.30 nM and 0.29 nM, respectively.

Optionally, the anti-DPR antibody, DPR-binding fragment or biotechnological derivative or variant thereof if analyzed in form of an IgG, optionally IgG1 has a binding affinity corresponding to an $EC_{50}$ (half maximal effective concentration) value of <15 nM for binding DPR protein $(GA)_6$ (SEQ ID NO: 80)—see Example 7—and/or an $EC_{50}$ value of ≤5 nM, optionally ≤2 nM, optionally ≤1 nM, or optionally ≤0.5 nM for binding DPR protein $(GA)_{10}$ (SEQ ID NO: 79), $(GA)_{15}$ (SEQ ID NO: 66) and/or $(GA)_{20}$ (SEQ ID NO: 82); see Examples 3, 4 and 7 as well as FIGS. 2 and 6. In one embodiment, the subject binds to the poly-GA peptide only if the repeat number n is ≥6; see Example 7 and FIG. 6. In addition, or alternatively, the antibody at least in form of an IgG binds with an affinity KD of about (0.5-2.0 nM) to poly-$(GA)_{15}$ (SEQ ID NO: 66), optionally a KD of about (0.05-0.5 nM) and optionally a KD of about (0.1-0.2 nM) to poly-$(GA)_{15}$ peptides (SEQ ID NO: 66) with an association rate constant of $(K_a=0.5-5\times10^5\ M^{-1}s^{-1})$ and dissociation constant $(K_d=1-5\times10^{-5}\ s^{-1})$ as determined by biolayer interferometry; see Example 8 and FIG. 7.

Accordingly, for high affinity and the mentioned $EC_{50}$ and KD values, the anti-DPR antibody, DPR-binding fragment or biotechnological derivative or variant thereof optionally further comprises a polypeptide sequence which is optionally heterologous to the CDRs or $V_H$ and $V_L$ chain amino acid sequence, optionally wherein the polypeptide sequence comprises a human constant domain, optionally of the IgG type, optionally of the IgG1 class or isotype.

On the other hand, DPR-binding fragments of the subject NI-308.5J10 antibody, especially Fab fragments prove particularly useful for designing and investigating synthetic and biotechnological derivatives or variants, optionally in context with smaller poly GA repeats, i.e. $(GA)_8$ (SEQ ID NO: 81); see Examples 13 to 16 and FIGS. 11 and 12. Thus, in another embodiment the antibody or DPR-binding fragment thereof of the present invention has a binding affinity to a poly-$(GA)_8$ (SEQ ID NO: 81) peptide corresponding to a $K_D$ (dissociation constant) less than 30 nM with a $K_a$ (association rate) less than $5\times10^5\ M^{-1}s^{-1}$ and a $K_d$ (dissociation rate) of less than $10\times10^{-3}\ s^{-1}$ as determined by Surface Plasmon Resonance (SPR), optionally wherein the DPR-binding fragment has a binding affinity to corresponding to a $K_D$ (dissociation constant) of 10 nM to 30 nM with a $K_a$ (association rate) of 1 to $5\times10^5\ M^{-1}s^{-1}$ and a $K_d$ (dissociation rate) of 2.5 to $10\times10^{-3}\ s^{-1}$ as determined by Surface Plasmon Resonance (SPR). In addition, or alternatively, the antibody or DPR-binding fragment thereof is optionally characterized in that the Fab fragment thereof has a thermal stability and melting temperature $T_m$, respectively, in the range of 78-82° C., optionally in the range of about 79-81° C. as determined by Differential Scanning calorimetry (VP-DSC); see Example 16.

Some antibodies are able to bind to a wide array of biomolecules, e.g., proteins. As the skilled artisan will appreciate, the term specific is used herein to indicate that other biomolecules than DPR do not significantly bind to the antibodies of the present invention. Optionally, the level of binding to a biomolecule other than DPRs results in a binding affinity which is at most only 20% or less, 10% or less, only 5% or less, only 2% or less or only 1% or less (i.e. at least 5, 10, 20, 50 or 100 fold lower, or anything beyond that) of the affinity to DPRs. In particular, as mentioned above and illustrated in the Examples and Figures, in accordance with the present invention the anti-DPR antibody or DPR-binding fragment thereof or biotechnological derivative or variant thereof optionally displays one, two, three, four or all five of the following binding characteristics: (i) recognizing a conformational epitope on poly-$(GA)_{15}$ peptides (SEQ ID NO: 66), i.e. being still able to bind poly-GA DPR aggregates after previous binding of a different anti-poly-GA DPR antibody (Example 9 and FIG. 8); (ii) binding to the poly-GA peptide coupled to BSA carrier protein with substantially the same affinity as to corresponding hydrophobically coated peptides (Example 3 and 4 as well as FIGS. 2 and 3); (iii) having substantially no or minimal cross-reactivity to unrelated amyloidogenic proteins at least those tested in Example 5 and shown in FIG. 4; (iv) being capable of binding aggregates comprising DPR-containing proteins as translated from the C9orf72 gene in the granule cell layer of the cerebellum of a C9orf72-FTLD patient (Example 11 and FIG. 10).

As mentioned before, accumulation of DPR protein aggregates in the frontal and temporal lobe of the brain is a hallmark of the neurodegenerative disorder FTLD. Patients with DPR aggregates in neuronal cytoplasmic inclusions, neuronal intranuclear inclusions and dystrophic neurites in the granule cell layer of the cerebellum often show an altered cognitive function. In particular, patients with FTLD show dementia, changes of the behavior as well as personality, language dysfunctions, and/or psychosis with are due to the degeneration of the frontal and temporal cortex, as described supra. Therefore, in one embodiment the antibody or DPR-binding fragment thereof of the present invention is useful for the treatment of diseases and/or disorders associated with DPRs. In a preferred embodiment, the antibody or DPR-binding fragment thereof of the present invention is useful in the treatment of FTLD and symptoms thereof. The therapeutic utility of the subject antibody or DPR-binding fragment thereof of the present invention can be validated in cellular assays such as those described in the background section (see also Example 17) and optionally such that if administered to a transgenic C9orf72 mouse model the antibody is capable of ameliorating at least one symptom of pathological hallmarks of C9orf72 disease such as neuronal loss, behavioral abnormalities, motor deficits and decreased survival (Example 18).

The corresponding nucleotide sequences encoding the above-identified variable regions are set forth in Table 2 below. Exemplary sets of CDRs of the amino acid sequences of the $V_H$ and $V_L$ chain are depicted in any one of FIGS. 1A-F. Hence, the present invention provides a genus of a novel anti-DPR antibody exemplified by an antibody or DPR-binding fragment thereof, which comprises in its variable region (i) the following six CDRs:
  (a) a VH-CDR1 comprising the amino acid sequence of SEQ ID NO: 3 (e.g., comprises SEQ ID NO:78),
  (b) a VH-CDR2 comprising the amino acid sequence of SEQ ID NO: 13,
  (c) a VH-CDR3 comprising the amino acid sequence of SEQ ID NO: 5,
  (d) a VL-CDR1 comprising the amino acid sequence of SEQ ID NO: 8,
  (e) a VL-CDR2 comprising the amino acid sequence of SEQ ID NO: 9,
  (f) a VL-CDR3 comprising the amino acid sequence of SEQ ID NO: 10;
(ii) the following six CDRs:
  (a) a VH-CDR1 comprising the amino acid sequence of SEQ ID NO: 3 (e.g., comprises SEQ ID NO:78),
  (b) a VH-CDR2 comprising the amino acid sequence of SEQ ID NO: 14,
  (c) a VH-CDR3 comprising the amino acid sequence of SEQ ID NO: 5,
  (d) a VL-CDR1 comprising the amino acid sequence of SEQ ID NO: 8,
  (e) a VL-CDR2 comprising the amino acid sequence of SEQ ID NO: 9,
  (f) a VL-CDR3 comprising the amino acid sequence of SEQ ID NO: 10;
(iii) the following six CDRs:
  (a) a VH-CDR1 comprising the amino acid sequence of SEQ ID NO: 3 (e.g., comprises SEQ ID NO:78),
  (b) a VH-CDR2 comprising the amino acid sequence of SEQ ID NO: 19,
  (c) a VH-CDR3 comprising the amino acid sequence of SEQ ID NO: 5,
  (d) a VL-CDR1 comprising the amino acid sequence of SEQ ID NO: 8,
  (e) a VL-CDR2 comprising the amino acid sequence of SEQ ID NO: 9,
  (f) a VL-CDR3 comprising the amino acid sequence of SEQ ID NO: 10; or
(iv) the following six CDRs:
  (a) a VH-CDR1 comprising the amino acid sequence of SEQ ID NO: 3 (e.g., comprises SEQ ID NO:78),
  (b) a VH-CDR2 comprising the amino acid sequence of SEQ ID NO: 22,
  (c) a VH-CDR3 comprising the amino acid sequence of SEQ ID NO: 5,
  (d) a VL-CDR1 comprising the amino acid sequence of SEQ ID NO: 8,
  (e) a VL-CDR2 comprising the amino acid sequence of SEQ ID NO: 9,
  (f) a VL-CDR3 comprising the amino acid sequence of SEQ ID NO: 10;
optionally wherein the antibody or DPR-binding fragment comprises in its variable region
  (i) the $V_H$ and $V_L$ chain amino acid sequence as depicted in SEQ ID NO: 2 and SEQ ID NO: 24;
  (ii) the $V_H$ and $V_L$ chain amino acid sequence as depicted in SEQ ID NO: 12 and SEQ ID NO: 24;
  (iii) the $V_H$ and $V_L$ chain amino acid sequence as depicted in SEQ ID NO: 15 and SEQ ID NO: 24;
  (iv) the $V_H$ and $V_L$ chain amino acid sequence as depicted in SEQ ID NO: 18 and SEQ ID NO: 24;
  (v) the $V_H$ and $V_L$ chain amino acid sequence as depicted in SEQ ID NO: 21 and SEQ ID NO: 24;
  (vi) the $V_H$ and $V_L$ chain amino acid sequence as depicted in SEQ ID NO: 12 and SEQ ID NO: 7;
  (vii) the $V_H$ and $V_L$ chain amino acid sequence as depicted in SEQ ID NO: 15 and SEQ ID NO: 7;
  (viii) the $V_H$ and $V_L$ chain amino acid sequence as depicted in SEQ ID NO: 18 and SEQ ID NO: 7;
  (ix) the $V_H$ and $V_L$ chain amino acid sequence as depicted in SEQ ID NO: 21 and SEQ ID NO: 7.

However, as already discussed supra the person skilled in the art is well aware of the fact that in addition or alternatively CDRs may be used, which differ in their amino acid sequence from those set forth in any one of FIGS. 1A-F by one, or two, even more amino acids in case of CDR2 and CDR3. Therefore, in one embodiment the antibody of the present invention, a biotechnological derivative and variant anti-DPR antibody and DPR fragment thereof is provided comprising in its variable region the CDRs as depicted in any one of FIGS. 1A-F, wherein one more, optionally no more than one or two CDRs thereof comprise one or more, optionally no more than two amino acid substitutions; see also supra.

As illustrated in the Examples, one or two amino acid substitutions in VH-CDR2 did not affect the binding affinity and characteristics of the original antibody. Regarding further or other amino acid substitutions within the CDRs and variable heavy and light chain amino acid sequences, respectively, optionally conservative amino acid substitutions are performed for example in accordance with the most frequently exchanged amino acids as analyzed and described by Mirsky et al., Mol. Biol. Evol. 35 (2014), 806-819; see FIG. 6 at page 813 of Mirsky et al. In this context, preliminary analyses of the CDRs of further human derived anti-poly-GA DPR antibodies with similar and different binding characteristics revealed certain positions within the CDRs of the subject antibody and amino acids substitutions which similar as for VH-CDR2 may be expected leave the antibody's unique binding characteristics unaffected in kind. The corresponding positions of preferred amino acid substitutions within the CDRs are indicated in FIG. 1 in bold and italics including those performed in VH-CDR2 in bold only.

In particular, within VH-CDR1 D may be substituted with S and/or S may be substituted with T; within VH-CDR3 V may be substituted with E, T may be substituted with S and/or M may be substituted with V; within VL-CDR1 R may be substituted with K, P may be substituted with S, R may be substituted with E, S may be substituted with G, and T may be substituted; within VL-CDR2 S may be substituted with A and/or A may be substituted with G; and in $V_L$-CDR3 G may be substituted with A, L may be substituted with I, and P may be substituted with S while S may be substituted with P. As mentioned, optionally amino acid substitutions are selected which belong to the same category in either or optionally both models LG and AB shown in FIG. 6 of Mirsky et al. (2014), supra, with the LG model being preferred for the tendency to keep amino acid properties, and wherein the amino acid substitutions are selected optionally such that the physiochemical properties of the original amino acid is substantially maintained, i.e. hydrophobic, polar or charged property or for example that in case two or more amino acid substitutions are performed, they compensate each other so as to provide the physiochemical property of the surface all together.

Provided herein is an anti-DPR antibody or fragment thereof, e.g., DPR Ab-1. The amino acid sequence information for DPR Ab-1 is shown in Table 12. In some embodiments, the anti-DPR antibody or antigen-binding fragment thereof binds to a DPR described herein, e.g., a chromosome 9 open reading frame 72 (C9orf72) dipeptide repeat (DPR) protein. In some embodiments, the DPR protein comprises a poly-glycine-alanine (GA) repeat, e.g., a poly-(GA)n repeat, wherein n is 1, 2, 3, 4, 5, 6, or greater (e.g., 1, 2, 3, 4, 5, 6, 7, 8, 9, 10, 11, 12, 13, 14, 15, or greater). In some embodiments, the DPR protein comprises a poly-(GA)n repeat, where n is between 6 and 15, inclusive of 6 and 15, e.g., where n is 15. In embodiments, the anti-DPR antibody or fragment thereof comprises DPR Ab-1 or a fragment (e.g., antigen-binding fragment) thereof. In some embodiments, the italicized asparagine residue in Table 12 is glycosylated; in other embodiments, the italicized asparagine residue in Table 12 is unglycosylated.

TABLE 12

| Amino acid sequence information for DPR Ab-1 | | |
|---|---|---|
| | Amino acid sequence | SEQ ID NO: |
| Heavy chain amino acid sequence with signal peptide (in some embodiments, the italicized asparagine is glycosylated; in other embodiments, the italicized asparagine is unglycosylated) (the CDRs are underlined) | MGWSLILLFLVAVAT RVLSQVQLVESGGGW QPGRSLRLSCAASGF TFSNHAMHWVRQAPG KGLEWVAVISYDGEN TYYADSIEGRFTISR DNFKNTLFLQMYSLT ADDTAMYFCARGGRR GHFTSYYLDYWGQGT LVTVSSASTKGPSVF PLAPSSKSTSGGTAA LGCLVKDYFPEPVTV SWNSGALTSGVHTFP AVLQSSGLYSLSSVV TVPSSSLGTQTYICN VNHKPSNTKVDKKVE PKSCDKTHTCPPCPA PELLGGPSVFLFPPK PKDTLMISRTPEVTC VVVDVSHEDPEVKFN WYVDGVEVHNAKTKP REEQYNSTYRVVSVL TVLHQDWLNGKEYKC KVSNKALPAPIEKTI SKAKGQPREPQVYTL PPSRDELTKNQVSLT CLVKGFYPSDIAVEW ESNGQPENNYKTTPP VLDSDGSFFLYSKLT VDKSRWQQGNVFSCS VMHEALHNHYTQKSL SLSPG | 37 |
| Heavy chain amino acid sequence (mature, without signal peptide) (the CDRs are underlined) | QVQLVESGGGWQPGR SLRLSCAASGFTFSN HAMHVWRQAPGKGLE WVAVISYDGENTYYA DSIEGRFTISRDNFK NTLFLQMYSLTADDT AMYFCARGGRRGHFT SYYLDYWGQGTLVTV SSASTKGPSVFPLAP SSKSTSGGTAALGCL VKDYFPEPVTVSWNS GALTSGVHTFPAVLQ SSGLYSLSSVVTVPS SSLGTQTYICNVNHK PSNTKVDKKVEPKSC DKTHTCPPCPAPELL GGPSVFLFPPKPKDT LMISRTPEVTCVVVD VSHEDPEVKFNWYVD | 38 |

TABLE 12-continued

| Amino acid sequence information for DPR Ab-1 | | |
|---|---|---|
| | Amino acid sequence | SEQ ID NO: |
| | GVEVHNAKTKPREEQ YNSTYRVVSVLTVLH QDWLNGKEYKCKVSN KALPAPIEKTISKAK GQPREPQVYTLPPSR DELTKNQVSLTCLVK GFYPSDIAVEWESNG QPENNYKTTPPVLDS DGSFFLYSKLTVDKS RWQQGNVFSCSVMHE ALHNHYTQKSLSLSP G | |
| Heavy chain constant domain amino acid sequence | ASTKGPSVFPLAPSS KSTSGGTAALGCLVK DYFPEPVTVSWNSGA LTSGVHTFPAVLQSS GLYSLSSVVTVPSSS LGTQTYICNVNHKPS NTKVDKKVEPKSCDK THTCPPCPAPELLGG PSVFLFPPKPKDTLM ISRTPEVTCVVVDVS HEDPEVKFNWYVDGV EVHNAKTKPREEQYN STYRVVSVLTVLHQD WLNGKEYKCKVSNKA LPAPIEKTISKAKGQ PREPQVYTLPPSRDE LTKNQVSLTCLVKGF YPSDIAVEWESNGQP ENNYKTTPPVLDSDG SFFLYSKLTVDKSRW QQGNVFSCSVMHEAL HNHYTQKSLSLSPG | 39 |
| Heavy chain variable region amino acid sequence (the CDRs are underlined) | QVQLVESGGGWQPGR SLRLSCAASGFTFSN HAMHVWRQAPGKGLE WVAVISYDGENTYYA DSIEGRFTISRDNFK NTLFLQMYSLTADDT AMYFCARGGRRGHFT SYYLDYWGQGTLVTV SS | 40 |
| Light chain amino acid sequence with signal peptide (the CDRs are underlined) | MDMRVPAQLLGLLLL WFPGSRCDIQMTQSP SSLSASVGDRVTITC RASQNIDKYLNWYQQ IPGKAPKLLIYAASS LHSGVPSRFSGSGSG TDFSLTISSLQPEDF AIYYCQQSYSSFRTF GQGTKLEIKRTVAAP SVFIFPPSDEQLKSG TASWCLLNNFYPREA KVQWKVDNALQSGNS QESVTEQDSKDSTYS LSSTLTLSKADYEKH KVYACEVTHQGLSSP VTKSFNRGEC | 41 |
| Light chain amino acid sequence (mature, without signal peptide) (the CDRs are underlined) | DIQMTQSPSSLSASV GDRVTITCRASQNID KYLNWYQQIPGKAPK LLIYAASSLHSGVPS RFSGSGSGTDFSLTI SSLQPEDFAIYYCQQ SYSSFRTFGQGTKLE IKRTVAAPSVFIFPP SDEQLKSGTASWCLL NNFYPREAKVQWKVD | 42 |

TABLE 12-continued

Amino acid sequence information for DPR Ab-1

| | Amino acid sequence | SEQ ID NO: |
|---|---|---|
| | NALQSGNSQESVTEQ DSKDSTYSLSSTLTL SKADYEKHKVYACEV THQGLSSPVTKSFNR GEC | |
| Light chain constant domain amino acid sequence | RTVAAPSVFIFPPSD EQLKSGTASVVCLLNN FYPREAKVQWKVDNA LQSGNSQESVTEQDS KDSTYSLSSTLTLSK ADYEKHKVYACEVTH QGLSSPVTKSFNRGE C | 43 |
| Light chain variable region amino acid sequence (the CDRs are underlined) | DIQMTQSPSSLSASV GDRVTITC<u>RASQNID KYLN</u>WYQQIPGKAPK LLIY<u>AASSLHS</u>GVPS RFSGSGSGTDFSLTI SSLQPEDFAIYYC<u>QQ SYSSFRT</u>FGQGTKLE IK | 44 |
| Heavy chain CDR 1 | GFTFSNHAMH | 45 |
| Heavy chain CDR 2 | VISYDGENTYYADSI EG | 46 |
| Heavy chain CDR 3 | GGRRGHFTSYYLDY | 47 |
| Light chain CDR 1 | RASQNIDKYLN | 48 |
| Light chain CDR 2 | AASSLHS | 49 |
| Light chain CDR 3 | QQSYSSFRT | 50 |

Framework (FR) and complementarity determining regions (CDRs) are indicated with the CDRs being underlined in Table 12. The Kabat numbering scheme was used (cf. www.bioinf.org.uk/abs/; Kabat et al., U.S. Dept. of Health and Human Services, "Sequence of Proteins of Immunological Interest" (1983) referred to in the mentioned web reference and given in Table 1 of WO 2016/050822 A2 at pages 39 and 40, incorporated herein by reference). Unless otherwise specified, references to the numbering of specific amino acid residue positions in an antibody or DPR-binding fragment, variant, or derivative thereof of the present invention are according to the Kabat numbering system, which however is theoretical and may not equally apply to every antibody of the present invention. For example, depending on the position of the first CDR the following CDRs might be shifted in either direction. Accordingly, in case of any inadvertent errors or inconsistencies regarding indication of CDRs in Table 12 and/or the sequence listing, the person skilled in the art on the basis of the disclosure of the present application, i.e. the variable heavy (VH) and variable light (VL) chain amino acid sequences of antibody DPR Ab-1, is well in the position to determine the correct CDR sequences in accordance with Kabat, which shall be used for defining the claimed antibody and DPR-binding fragment thereof.

Provided herein is a composition comprising an anti-DPR (e.g., anti-C9ORF72 DPR) antibody or fragment thereof (e.g., that binds, e.g., binds specifically and/or with high affinity, to, a poly-(GA)n repeat, e.g., a poly-(GA)n repeat described herein), wherein the anti-DPR antibody or fragment thereof comprises:

(i) a heavy chain comprising, consisting of, or consisting essentially of the amino acid sequence of SEQ ID NO: 37 or 38 (or an amino acid sequence at least 95%, e.g., 95%, 96%, 97%, 98%, 99%, or 100% identical to SEQ ID NO: 37 of 38),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain comprises a heavy chain variable region amino acid sequence that is no more than 123 amino acids in length;

(ii) a heavy chain comprising a heavy chain constant domain comprising, consisting of, or consisting essentially of the amino acid sequence of SEQ ID NO: 39 (or an amino acid sequence at least 95%, e.g., 95%, 96%, 97%, 98%, 99%, or 100% identical to SEQ ID NO: 39),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain comprises a heavy chain variable region amino acid sequence that is no more than 123 amino acids in length;

(iii) a heavy chain comprising a heavy chain variable region comprising, consisting of, or consisting essentially of SEQ ID NO: 40 (or an amino acid sequence at least 95%, e.g., 95%, 96%, 97%, 98%, 99%, or 100% identical to SEQ ID NO: 40),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain comprises a heavy chain variable region amino acid sequence that is no more than 123 amino acids in length;

(iv) a heavy chain variable region amino acid sequence comprising, consisting of, or consisting essentially of SEQ ID NO: 40 (or an amino acid sequence at least 95%, e.g., 95%, 96%, 97%, 98%, 99%, or 100% identical to SEQ ID NO: 40),
optionally wherein the heavy chain variable region amino acid sequence is no more than 123 amino acids in length;

(v) a light chain comprising, consisting of, or consisting essentially of SEQ ID NO: 41 or 42 (or an amino acid sequence at least 95%, e.g., 95%, 96%, 97%, 98%, 99%, or 100% identical to SEQ ID NO: 41 or 42),
optionally wherein the light chain amino acid sequence (e.g., light chain mature sequence) is no more than 214 amino acids in length, and/or wherein the light chain comprises a light chain variable region amino acid sequence that is no more than 107 amino acids in length;

(vi) a light chain comprising a light chain constant domain comprising, consisting of, or consisting essentially of SEQ ID NO: 43 (or an amino acid sequence at least 95%, e.g., 95%, 96%, 97%, 98%, 99%, or 100% identical to SEQ ID NO: 43), optionally wherein the light chain amino acid sequence (e.g., light chain mature sequence) is no more than 214 amino acids in length, and/or wherein the light chain comprises a light chain variable region amino acid sequence that is no more than 107 amino acids in length;

(vii) a light chain comprising a light chain variable region amino acid sequence comprising, consisting of, or consisting essentially of SEQ ID NO: 44 (or an amino acid sequence at least 95%, e.g., 95%, 96%, 97%, 98%, 99%, or 100% identical to SEQ ID NO: 44), optionally wherein the light chain amino acid sequence (e.g., light chain mature sequence) is no more than 214 amino acids in length, and/or wherein the light chain variable region amino acid sequence is no more than 107 amino acids in length;

(viii) a light chain variable region amino acid sequence comprising, consisting of, or consisting essentially of SEQ ID NO: 44 (or an amino acid sequence at least 95%, e.g., 95%, 96%, 97%, 98%, 99%, or 100% identical to SEQ ID NO: 44), optionally wherein the light chain variable region amino acid sequence is no more than 107 amino acids in length;

(ix) a heavy chain comprising a heavy chain variable region comprising a CDR1 amino acid sequence of SEQ ID NO: 45 (or an amino acid sequence at least 95%, e.g., 95%, 96%, 97%, 98%, 99%, or 100% identical to SEQ ID NO: 45); a CDR2 amino acid sequence of SEQ ID NO: 46 (or an amino acid sequence at least 95%, e.g., 95%, 96%, 97%, 98%, 99%, or 100% identical to SEQ ID NO: 46), and a CDR3 amino acid sequence of SEQ ID NO: 47 (or an amino acid sequence at least 95%, e.g., 95%, 96%, 97%, 98%, 99%, or 100% identical to SEQ ID NO: 47), optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;

(x) a heavy chain variable region comprising a CDR1 amino acid sequence of SEQ ID NO: 45 (or an amino acid sequence at least 95%, e.g., 95%, 96%, 97%, 98%, 99%, or 100% identical to SEQ ID NO: 45); a CDR2 amino acid sequence of SEQ ID NO: 46 (or an amino acid sequence at least 95%, e.g., 95%, 96%, 97%, 98%, 99%, or 100% identical to SEQ ID NO: 46), and a CDR3 amino acid sequence of SEQ ID NO: 47 (or an amino acid sequence at least 95%, e.g., 95%, 96%, 97%, 98%, 99%, or 100% identical to SEQ ID NO: 47), optionally wherein the heavy chain variable region amino acid sequence is no more than 123 amino acids in length;

(xi) a light chain comprising a light chain variable region comprising a CDR1 amino acid sequence of SEQ ID NO: 48 (or an amino acid sequence at least 95%, e.g., 95%, 96%, 97%, 98%, 99%, or 100% identical to SEQ ID NO: 48), a CDR2 amino acid sequence of SEQ ID NO: 49 (or an amino acid sequence at least 95%, e.g., 95%, 96%, 97%, 98%, 99%, or 100% identical to SEQ ID NO: 49), and a CDR3 amino acid sequence of SEQ ID NO: 50 (or an amino acid sequence at least 95%, e.g., 95%, 96%, 97%, 98%, 99%, or 100% identical to SEQ ID NO: 50), optionally wherein the light chain amino acid sequence (e.g., light chain mature sequence) is no more than 214 amino acids in length, and/or wherein the light chain variable region amino acid sequence is no more than 107 amino acids in length;

(xii) a light chain variable region comprising a CDR1 amino acid sequence of SEQ ID NO: 48 (or an amino acid sequence at least 95%, e.g., 95%, 96%, 97%, 98%, 99%, or 100% identical to SEQ ID NO: 48), a CDR2 amino acid sequence of SEQ ID NO: 49 (or an amino acid sequence at least 95%, e.g., 95%, 96%, 97%, 98%, 99%, or 100% identical to SEQ ID NO: 49), and a CDR3 amino acid sequence of SEQ ID NO: 50 (or an amino acid sequence at least 95%, e.g., 95%, 96%, 97%, 98%, 99%, or 100% identical to SEQ ID NO: 50), optionally wherein the light chain variable region amino acid sequence is no more than 107 amino acids in length; and/or (xiii) a heavy chain and a light chain, the light chain comprising a light chain variable region comprising a CDR1 amino acid sequence of SEQ ID NO: 48 (or an amino acid sequence at least 95%, e.g., 95%, 96%, 97%, 98%, 99%, or 100% identical to SEQ ID NO: 48), a CDR2 amino acid sequence of SEQ ID NO: 49 (or an amino acid sequence at least 95%, e.g., 95%, 96%, 97%, 98%, 99%, or 100% identical to SEQ ID NO: 49), and a CDR3 amino acid sequence of SEQ ID NO: 50 (or an amino acid sequence at least 95%, e.g., 95%, 96%, 97%, 98%, 99%, or 100% identical to SEQ ID NO: 50), optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain comprises a variable region amino acid sequence that is no more than 123 amino acids in length, and/or optionally wherein the light chain amino acid sequence is no more than 214 amino acids in length, and/or wherein the light chain variable region amino acid sequence is no more than 107 amino acids in length.

In one embodiment, the provided herein is a polynucleotide, optionally linked to heterologous nucleic acid, wherein (i) the polynucleotide encodes an immunoglobulin variable heavy chain with the VH-CDRs described herein, and wherein the immunoglobulin variable heavy chain when paired with an immunoglobulin variable light chain comprising the amino acid sequence set forth in Table 12 is capable of binding (e.g., specifically and/or with high affinity) to a DPR (e.g., a poly-(GA)n) described herein, and/or (ii) the polynucleotide encodes an immunoglobulin variable light chain with the VL-CDRs described herein, and wherein the immunoglobulin variable light chain when paired with an immunoglobulin variable heavy chain comprising the amino acid sequence set forth in Table 12 is capable of binding (e.g., specifically and/or with high affinity) to a DPR (e.g., poly-(GA)n) described herein.

In some aspects, provided herein is an antibody or fragment thereof comprising a signal peptide at the N-terminus. In some embodiments, the signal peptide comprises the amino acid sequence, MGWSLILLFLVAVATRVLS (SEQ ID NO: 59) or an amino acid sequence at least 95%, e.g., 95%, 96%, 97%, 98%, 99%, or 100% identical to SEQ ID NO: 59. In other embodiments, the signal peptide comprises the amino acid sequence, MDMRVPAQLLGLLLL-WFPGSRC (SEQ ID NO: 60) or an amino acid sequence at least 95%, e.g., 95%, 96%, 97%, 98%, 99%, or 100% identical to SEQ ID NO: 60.

In embodiments, the heavy chain thereof does not comprise a lysine residue at the C-terminal end of its amino acid sequence. In embodiments, the heavy chain thereof has a glycine at the C-terminal end of its amino acid sequence.

In embodiments, the heavy chain amino acid sequence (e.g., heavy chain mature sequence) is no more than 452 amino acids in length (e.g., is 452 amino acids in length). In embodiments, the heavy chain does not comprise a lysine residue at the C-terminal end of its amino acid sequence. In embodiments, the heavy chain has a glycine at the C-terminal end of its amino acid sequence. In embodiments, the heavy chain variable region amino acid sequence is no more than 123 amino acids in length (e.g., is 123 amino acids in length). In embodiments, the light chain amino acid sequence is no more than 214 amino acids in length (e.g., is 214 amino acids in length). In embodiments, the light chain variable region amino acid sequence is no more than 107 amino acids in length (e.g., is 107 amino acids in length).

In some embodiments, the antibody or fragment thereof described herein comprises a heavy chain having an IgG1 isotype, e.g., a human IgG1 (hIgG1) isotype. In embodiments, the heavy chain comprises the allotype G1m1,17.

In some embodiments, the antibody or fragment thereof described herein comprises a light chain having a Kappa isotype, e.g., human Kappa isotype. In embodiments, the light chain comprises the allotype Km3.

In some embodiments, the antibody or fragment thereof described herein is attached to a drug; or is detectably labeled with a label, e.g., an enzyme, a radioisotope, a fluorophore, a tag, a heavy metal, and/or a flag.

The antibody of the present invention may be human-derived, in particular for therapeutic applications. Alternatively, the antibody of the present invention is a rodent, rodentized or chimeric rodent-human antibody, optionally a murine, murinized or chimeric murine-human antibody or a rat, ratinized or chimeric rat-human antibody which is particularly useful for diagnostic methods and studies in animals. In one embodiment the antibody of the present invention is a chimeric rodent-human or a rodentized antibody.

As discussed above, the antibody of the invention may exist in a variety of forms besides complete antibodies; including, for example, Fv, Fab and F(ab)$_2$, as well as in single chains; see e.g. international application WO 88/09344. In one embodiment therefore, the antibody of the present invention is provided, which is selected from the group consisting of a single chain Fv fragment (scFv), a F(ab') fragment, a F(ab) fragment, and a F(ab')2 fragment.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

Antibodies, or DPR-binding fragments, synthetic or biotechnological variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or DPR-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of DPR protein aggregation and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO2005/018572, which is incorporated by reference in its entirety.

In certain antibodies, or DPR-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing DPR protein localization. In other cases, it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as DPR protein localization, biodistribution and serum half-life, may easily be measured and quantified using well know immunological techniques without undue experimentation.

In certain antibodies, or DPR-binding fragments, variants, or derivatives thereof described herein, the Fc portion may be mutated or exchanged for alternative protein sequences to increase the cellular uptake of antibodies by way of example by enhancing receptor-mediated endocytosis of antibodies via Fcγ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with a specific sequences binding to DPRs as well as a cell surface receptor may be engineered using techniques known in the art.

In certain antibodies, or DPR-binding fragments, variants, or derivatives thereof described herein, the Fc portion may be mutated or exchanged for alternative protein sequences or the antibody may be chemically modified to increase its blood brain barrier penetration.

Modified forms of antibodies, or DPR-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced", i.e., are produced using recombinant DNA technology. Exemplary techniques for making antibody molecules or fragments thereof are discussed in more detail elsewhere herein.

Antibodies, or DPR-binding fragments, biotechnological variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Antibody fragments that recognize specific epitopes may be generated by known techniques. For example, Fab and F(ab')$_2$ fragments may be produced recombinantly or by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

Antibodies of the present invention can be produced by any method known in the art for the synthesis of antibodies, in particular, by chemical synthesis or optionally by recombinant expression techniques as described herein.

In one embodiment, an antibody, or DPR-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an IgG$_1$ human constant domain, see, e.g., international applications WO 02/060955 and WO 02/096948A2. This vector is engineered to delete the CH2 domain and provide a synthetic vector expressing a domain deleted IgG$_1$ constant region.

In certain embodiments, antibodies, or DPR-binding fragments, variants, or derivatives thereof of the present invention are minibodies. Minibodies can be made using methods described in the art, see, e.g., U.S. Pat. No. 5,837,821 or international application WO 94/09817.

In one embodiment, an antibody, or DPR-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase DPR protein localization. Similarly, it may be desirable to simply delete that part of one or more constant region domains that control the effector function (e.g., complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Yet other embodiments comprise the addition of one or more amino acids to the constant region to enhance desirable characteristics such as an effector function or provide for more cytotoxin or carbohydrate attachment. In such embodiments it may be desirable to insert or replicate specific sequences derived from selected constant region domains.

III. Polynucleotides Encoding Antibodies of the Present Invention

The present invention also relates to one or more polynucleotide(s) encoding any one of the antibodies, or DPR-binding fragments, variants, or derivatives thereof described in section II, supra. A polynucleotide encoding an antibody, or DPR-binding fragment, variant, or derivative thereof can be composed of any polyribonucleotide or polydeoxribonucleotide, which may be unmodified RNA or DNA or modified RNA or DNA. For example, a polynucleotide encoding an antibody, or DPR-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single-stranded and double-stranded regions. In addition, a polynucleotide encoding an antibody, or DPR-binding fragment, variant, or derivative thereof can be composed of triple-stranded regions comprising RNA or DNA or both RNA and DNA. A polynucleotide encoding an antibody, or DPR-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Optionally, conservative amino acid substitutions are made at one or more non-essential amino acid residues.

As is well known, RNA may be isolated from the original B cells, hybridoma cells or from other transformed cells by standard techniques, such as a guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art. In one embodiment, cDNAs that encode the light and the heavy chains of the antibody may be made, either simultaneously or separately, using reverse transcriptase and DNA polymerase in accordance with well-known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as human constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis. In this context, the present invention also relates to a polynucleotide encoding at least the binding domain or variable region of an immunoglobulin chain of the antibody of the present invention.

In a preferred embodiment of the present invention, the polynucleotide comprises, consists essentially of, or consists of a nucleic acid having a polynucleotide sequence of the $V_H$ or $V_L$ region of an anti-DPR antibody as depicted in and Table 2. In this respect, the person skilled in the art will readily appreciate that the polynucleotides encoding at least the variable domain of the light and/or heavy chain may encode the variable domain of both immunoglobulin chains or only one. In one embodiment therefore, the polynucleotide comprises, consists essentially of, or consists of a nucleic acid having a polynucleotide sequence of the $V_H$ and the $V_L$ region of an anti-DPR antibody and/or fragments thereof as depicted in Table 2.

TABLE 2

Nucleotide sequences of the $V_H$ and $V_L$ region of antibodies and antibody variants recognizing poly-GA DPRs, optionally C9orf72-(poly-GA)-DPRs.

| Antibody | Nucleotide sequences of variable heavy ($V_H$) and variable light ($V_L$) chains |
|---|---|
| NI-308.5J10 $V_H$ | CAGGTGCAGCTGCAGGAGTC GGGCCCAGGACTGGTGAAGC CTTCGGAGACCCTGTCCCTC ACTTACACTGTCTTAGGTGG CTCCGTCAGTGATTACTACT GGAGCTGCATCCGGCAGCCC GCCGGGAAGGGACTGGAGTG GATTGGGCGAACATATACTA ACGGGAAGACCACTTACACT TACAACCCCTCCCTCGAGAG TCGACTCAGTTTGTCTATAG ACACGTCCATGAACCAATTC TCCCTGAAGTTGACCTCTGT GACGGCCGCGGACACGGCCG TCTATTACTGCGCGAGATGG GGGGCGGTGACTGGTGACTA CTACTACGGTATGGACGTCT GGGGCCCAGGCACCCTGGTC ACCGTCTCCTCG<br>SEQ ID NO: 1 |
| NI-308.5J10 $V_K$ | GAAATTGTGCTGACTCAGTC TCCACTCTCCCTGTCCGTCA CCCCTGGAGAGCCGGCCTCC ATCTCCTGCAGGTCTCCTCG GAGCCTTCTACATACTAATG GATATACATATTTGGACTGG TACCTACAAAGGCCAGGGCA GTCTCCACAACTCCTGATCT TTTTGGCTTCTAATCGGGCC TCCGGGGTCCCTGACAGGTT |

TABLE 2-continued

Nucleotide sequences of the $V_H$ and $V_L$ region of antibodies and antibody variants recognizing poly-GA DPRs, optionally C9orf72-(poly-GA)-DPRs.

| Antibody | Nucleotide sequences of variable heavy ($V_H$) and variable light ($V_L$) chains |
|---|---|
| | CAGTGGCAGCGGATCAGGCA<br>CAAATTTTACACTGAGAATC<br>AGCGGAGTGGAGGCTGACGA<br>TGTTGGAGTTTATTACTGCA<br>TGCAAGGTCTACAACCTTCG<br>TGGACGTTCGGCCAGGGGAC<br>CAAGGTGGAAATCAAA<br>SEQ ID NO: 6 |
| NI-308.5J10 $V_H$-N54S | CAGGTGCAGCTGCAGGAGTC<br>GGGCCCAGGACTGGTGAAGC<br>CTTCGGAGACCCTGTCCCTC<br>ACTTACACTGTCTTAGGTGG<br>CTCCGTCAGTGATTACTACT<br>GGAGCTGCATCCGGCAGCCC<br>GCCGGGAAGGGACTGGAGTG<br>GATTGGGCGAACATATACTA<br>GCGGGAAGACCACTTACACT<br>TACAACCCCTCCCTCGAGAG<br>TCGACTCAGTTTGTCTATAG<br>ACACGTCCATGAACCAATTC<br>TCCCTGAAGTTGACCTCTGT<br>GACGGCCGCGGACACGGCCG<br>TCTATTACTGCGCGAGATGG<br>GGGGCGGTGACTGGTGACTA<br>CTACTACGGTATGGACGTCT<br>GGGGCCCAGGCACCCTGGTC<br>ACCGTCTCCTCG<br>SEQ ID NO: 11 |
| NI-308.5J10 $V_H$-N54T | CAGGTGCAGCTGCAGGAGTC<br>GGGCCCAGGACTGGTGAAGC<br>CTTCGGAGACCCTGTCCCTC<br>ACTTACACTGTCTTAGGTGG<br>CTCCGTCAGTGATTACTACT<br>GGAGCTGCATCCGGCAGCCC<br>GCCGGGAAGGGACTGGAGTG<br>GATTGGGCGAACATATACTA<br>CCGGGAAGACCACTTACACT<br>TACAACCCCTCCCTCGAGAG<br>TCGACTCAGTTTGTCTATAG<br>ACACGTCCATGAACCAATTC<br>TCCCTGAAGTTGACCTCTGT<br>GACGGCCGCGGACACGGCCG<br>TCTATTACTGCGCGAGATGG<br>GGGGCGGTGACTGGTGACTA<br>CTACTACGGTATGGACGTCT<br>GGGGCCCAGGCACCCTGGTC<br>ACCGTCTCCTCG<br>SEQ ID NO: 14 |
| NI-308.5J10 $V_H$-G55S | CAGGTGCAGCTGCAGGAGTC<br>GGGCCCAGGACTGGTGAAGC<br>CTTCGGAGACCCTGTCCCTC<br>ACTTACACTGTCTTAGGTGG<br>CTCCGTCAGTGATTACTACT<br>GGAGCTGCATCCGGCAGCCC<br>GCCGGGAAGGGACTGGAGTG<br>GATTGGGCGAACATATACTA<br>ACAGCAAGACCACTTACACT<br>TACAACCCCTCCCTCGAGAG<br>TCGACTCAGTTTGTCTATAG<br>ACACGTCCATGAACCAATTC<br>TCCCTGAAGTTGACCTCTGT<br>GACGGCCGCGGACACGGCCG<br>TCTATTACTGCGCGAGATGG<br>GGGGCGGTGACTGGTGACTA<br>CTACTACGGTATGGACGTCT |

TABLE 2-continued

Nucleotide sequences of the $V_H$ and $V_L$ region of antibodies and antibody variants recognizing poly-GA DPRs, optionally C9orf72-(poly-GA)-DPRs.

| Antibody | Nucleotide sequences of variable heavy ($V_H$) and variable light ($V_L$) chains |
|---|---|
| | GGGGCCCAGGCACCCTGGTC<br>ACCGTCTCCTCG<br>SEQ ID NO: 17 |
| NI-308.5J10 $V_H$-G55T | CAGGTGCAGCTGCAGGAGTC<br>GGGCCCAGGACTGGTGAAGC<br>CTTCGGAGACCCTGTCCCTC<br>ACTTACACTGTCTTAGGTGG<br>CTCCGTCAGTGATTACTACT<br>GGAGCTGCATCCGGCAGCCC<br>GCCGGGAAGGGACTGGAGTG<br>GATTGGGCGAACATATACTA<br>ACACCAAGACCACTTACACT<br>TACAACCCCTCCCTCGAGAG<br>TCGACTCAGTTTGTCTATAG<br>ACACGTCCATGAACCAATTC<br>TCCCTGAAGTTGACCTCTGT<br>GACGGCCGCGGACACGGCCG<br>TCTATTACTGCGCGAGATGG<br>GGGGCGGTGACTGGTGACTA<br>CTACTACGGTATGGACGTCT<br>GGGGCCCAGGCACCCTGGTC<br>ACCGTCTCCTCG<br>SEQ ID NO: 20 |
| NI-308.5J10 $V_K$-N75D | GAAATTGTGCTGACTCAGTC<br>TCCACTCTCCCTGTCCGTCA<br>CCCCTGGAGAGCCGGCCTCC<br>ATCTCCTGCAGGTCTCCTCG<br>GAGCCTTCTACATACTAATG<br>GATATACATATTTGGACTGG<br>TACCTACAAAGGCCAGGGCA<br>GTCTCCACAACTCCTGATCT<br>TTTTGGCTTCTAATCGGGCC<br>TCCGGGGTCCCTGACAGGTT<br>CAGTGGCAGCGGATCAGGCA<br>CAGACTTTACACTGAGAATC<br>AGCGGAGTGGAGGCTGACGA<br>TGTTGGAGTTTATTACTGCA<br>TGCAAGGTCTACAACCTTCG<br>TGGACGTTCGGCCAGGGGAC<br>CAAGGTGGAAATCAAA<br>SEQ ID NO: 23 |

The amino acid sequence of the DPR Ab-1 antibody or fragment thereof can be encoded by various nucleotide sequences. For example, the codons can be optimized to maximize expression of the polypeptide(s). An exemplary set of nucleotide sequences encoding DPR Ab-1 is shown in Table 13 below.

TABLE 13

Nucleotide sequences encoding DPR Ab-1

| | Nucleotide sequence | SEQ ID NO: |
|---|---|---|
| Heavy chain nucleotide sequence with signal peptide | ATGGGTTGGAGCCTC<br>ATCTTGCTGTTTCTT<br>GTCGCTGTTGCTACG<br>CGTGTCCTGTCGCAG<br>GTGCAGCTGGTGGAG<br>TCTGGGGGAGGCGTA<br>GTCCAGCCTGGGAGG<br>TCCCTGAGACTGTCC | 51 |

TABLE 13-continued

Nucleotide sequences encoding DPR Ab-1

| Nucleotide sequence | SEQ ID NO: |
|---|---|
| TGTGCAGCCTCTGGA<br>TTCACCTTCAGTAAT<br>CATGCTATGCACTGG<br>GTCCGCCAGGCTCCA<br>GGCAAGGGGCTGGAG<br>TGGGTGGCAGTTATA<br>TCATATGATGGCGAG<br>AACACATATTATGCA<br>GACTCCATTGAGGGC<br>CGATTCACCATTTCC<br>AGAGACAATTTCAAG<br>AACACACTCTTTCTA<br>CAAATGTACAGCCTG<br>ACAGCTGATGACACG<br>GCTATGTACTTCTGT<br>GCGAGAGGGGCCGT<br>CGGGGGCACTTCACC<br>TCATACTACCTTGAC<br>TACTGGGGCCAGGGA<br>ACCCTGGTCACCGTC<br>TCCTCGGCTAGTACC<br>AAGGGCCCATCGGTC<br>TTCCCCCTGGCACCC<br>TCCTCCAAGAGCACC<br>TCTGGGGGCACAGCG<br>GCCCTGGGCTGCCTG<br>GTCAAGGACTACTTC<br>CCCGAACCCGTGACG<br>GTGTCGTGGAACTCA<br>GGCGCCCTGACCAGC<br>GGCGTGCACACCTTC<br>CCGGCTGTCCTACAG<br>TCCTCAGGACTCTAC<br>TCCCTCAGCAGCGTG<br>GTGACCGTGCCCTCC<br>AGCAGCTTGGGCACC<br>CAGACCTACATCTGC<br>AACGTGAATCACAAG<br>CCCAGCAACACCAAG<br>GTGGACAAGAAAGTT<br>GAGCCCAAATCTTGT<br>GACAAGACTCACACA<br>TGCCCACCGTGCCCA<br>GCACCTGAACTCCTG<br>GGGGGACCGTCAGTC<br>TTCCTCTTCCCCCCA<br>AAACCCAAGGACACC<br>CTCATGATCTCCCGG<br>ACCCCTGAGGTCACA<br>TGCGTGGTGGTGGAC<br>GTGAGCCACGAAGAC<br>CCTGAGGTCAAGTTC<br>AACTGGTACGTGGAC<br>GGCGTGGAGGTGCAT<br>AATGCCAAGACAAAG<br>CCGCGGGAGGAGCAG<br>TACAACAGCACGTAC<br>CGTGTGGTCAGCGTC<br>CTCACCGTCCTGCAC<br>CAGGACTGGCTGAAT<br>GGCAAGGAGTACAAG<br>TGCAAGGTTTCCAAC<br>AAAGCCCTCCCAGCC<br>CCCATCGAGAAAACC<br>ATCTCCAAAGCCAAA<br>GGGCAGCCCCGAGAA<br>CCACAGGTGTACACC<br>CTGCCCCCATCCCGG<br>GATGAGCTGACCAAG<br>AACCAGGTCAGCCTG<br>ACCTGCCTGGTCAAA<br>GGCTTCTATCCCAGC<br>GACATCGCCGTGGAG<br>TGGGAGAGCAATGGG | |
| CAGCCGGAGAACAAC<br>TACAAGACCACGCCT<br>CCCGTGTTGGACTCC<br>GACGGCTCCTTCTTC<br>CTCTACAGCAAGCTC<br>ACCGTGGACAAGAGC<br>AGGTGGCAGCAGGGG<br>AACGTCTTCTCATGC<br>TCCGTGATGCATGAG<br>GCTCTGCACAACCAC<br>TACACGCAAAAAAGC<br>CTCTCCCTGTCTCCC<br>GGTTGA | |
| Heavy chain nucleotide sequence (mature, without signal peptide) | CAGGTGCAGCTGGTG<br>GAGTCTGGGGGAGGC<br>GTAGTCCAGCCTGGG<br>AGGTCCCTGAGACTG<br>TCCTGTGCAGCCTCT<br>GGATTCACCTTCAGT<br>AATCATGCTATGCAC<br>TGGGTCCGCCAGGCT<br>CCAGGCAAGGGGCTG<br>GAGTGGGTGGCAGTT<br>ATATCATATGATGGC<br>GAGAACACATATTAT<br>GCAGACTCCATTGAG<br>GGCCGATTCACCATT<br>TCCAGAGACAATTTC<br>AAGAACACACTCTTT<br>CTACAAATGTACAGC<br>CTGACAGCTGATGAC<br>ACGGCTATGTACTTC<br>TGTGCGAGAGGGGGC<br>CGTCGGGGGCACTTC<br>ACCTCATACTACCTT<br>GACTACTGGGGCCAG<br>GGAACCCTGGTCACC<br>GTCTCCTCGGCTAGT<br>ACCAAGGGCCCATCG<br>GTCTTCCCCCTGGCA<br>CCCTCCTCCAAGAGC<br>ACCTCTGGGGGCACA<br>GCGGCCCTGGGCTGC<br>CTGGTCAAGGACTAC<br>TTCCCCGAACCCGTG<br>ACGGTGTCGTGGAAC<br>TCAGGCGCCCTGACC<br>AGCGGCGTGCACACC<br>TTCCCGGCTGTCCTA<br>CAGTCCTCAGGACTC<br>TACTCCCTCAGCAGC<br>GTGGTGACCGTGCCC<br>TCCAGCAGCTTGGGC<br>ACCCAGACCTACATC<br>TGCAACGTGAATCAC<br>AAGCCCAGCAACACC<br>AAGGTGGACAAGAAA<br>GTTGAGCCCAAATCT<br>TGTGACAAGACTCAC<br>ACATGCCCACCGTGC<br>CCAGCACCTGAACTC<br>CTGGGGGGACCGTCA<br>GTCTTCCTCTTCCCC<br>CCAAAACCCAAGGAC<br>ACCCTCATGATCTCC<br>CGGACCCCTGAGGTC<br>ACATGCGTGGTGGTG<br>GACGTGAGCCACGAA<br>GACCCTGAGGTCAAG<br>TTCAACTGGTACGTG<br>GACGGCGTGGAGGTG<br>CATAATGCCAAGACA<br>AAGCCGCGGGAGGAG | 52 |

TABLE 13-continued

Nucleotide sequences encoding DPR Ab-1

| | Nucleotide sequence | SEQ ID NO: |
|---|---|---|
| | CAGTACAACAGCACG | |
| | TACCGTGTGGTCAGC | |
| | GTCCTCACCGTCCTG | |
| | CACCAGGACTGGCTG | |
| | AATGGCAAGGAGTAC | |
| | AAGTGCAAGGTTTCC | |
| | AACAAAGCCCTCCCA | |
| | GCCCCCATCGAGAAA | |
| | ACCATCTCCAAAGCC | |
| | AAAGGGCAGCCCCGA | |
| | GAACCACAGGTGTAC | |
| | ACCCTGCCCCCATCC | |
| | CGGGATGAGCTGACC | |
| | AAGAACCAGGTCAGC | |
| | CTGACCTGCCTGGTC | |
| | AAAGGCTTCTATCCC | |
| | AGCGACATCGCCGTG | |
| | GAGTGGGAGAGCAAT | |
| | GGGCAGCCGGAGAAC | |
| | AACTACAAGACCACG | |
| | CCTCCCGTGTTGGAC | |
| | TCCGACGGCTCCTTC | |
| | TTCCTCTACAGCAAG | |
| | CTCACCGTGGACAAG | |
| | AGCAGGTGGCAGCAG | |
| | GGGAACGTCTTCTCA | |
| | TGCTCCGTGATGCAT | |
| | GAGGCTCTGCACAAC | |
| | CACTACACGCAAAAA | |
| | AGCCTCTCCCTGTCT | |
| | CCCGGTTGA | |
| Heavy chain constant domain nucleotide sequence | GCTAGTACCAAGGGC CCATCGGTCTTCCCC CTGGCACCCTCCTCC AAGAGCACCTCTGGG GGCACAGCGGCCCTG GGCTGCCTGGTCAAG GACTACTTCCCCGAA CCCGTGACGGTGTCG TGGAACTCAGGCGCC CTGACCAGCGGCGTG CACACCTTCCCGGCT GTCCTACAGTCCTCA GGACTCTACTCCCTC AGCAGCGTGGTGACC GTGCCCTCCAGCAGC TTGGGCACCCAGACC TACATCTGCAACGTG AATCACAAGCCCAGC AACACCAAGGTGGAC AAGAAAGTTGAGCCC AAATCTTGTGACAAG ACTCACACATGCCCA CCGTGCCCAGCACCT GAACTCCTGGGGGGA CCGTCAGTCTTCCTC TTCCCCCCAAAACCC AAGGACACCCTCATG ATCTCCCGGACCCCT GAGGTCACATGCGTG GTGGTGGACGTGAGC CACGAAGACCCTGAG GTCAAGTTCAACTGG TACGTGGACGGCGTG GAGGTGCATAATGCC AAGACAAAGCCGCGG GAGGAGCAGTACAAC AGCACGTACCGTGTG GTCAGCGTCCTCACC GTCCTGCACCAGGAC TGGCTGAATGGCAAG GAGTACAAGTGCAAG GTTTCCAACAAAGCC | 53 |
| | CTCCCAGCCCCCATC GAGAAAACCATCTCC AAAGCCAAAGGGCAG CCCCGAGAACCACAG GTGTACACCCTGCCC CCATCCCGGGATGAG CTGACCAAGAACCAG GTCAGCCTGACCTGC CTGGTCAAAGGCTTC TATCCCAGCGACATC GCCGTGGAGTGGGAG AGCAATGGGCAGCCG GAGAACAACTACAAG ACCACGCCTCCCGTG TTGGACTCCGACGGC TCCTTCTTCCTCTAC AGCAAGCTCACCGTG GACAAGAGCAGGTGG CAGCAGGGGAACGTC TTCTCATGCTCCGTG ATGCATGAGGCTCTG CACAACCACTACACG CAAAAAAGCCTCTCC CTGTCTCCCGGTTGA | |
| Heavy chain variable region nucleotide sequence | CAGGTGCAGCTGGTG GAGTCTGGGGGAGGC GTAGTCCAGCCTGGG AGGTCCCTGAGACTG TCCTGTGCAGCCTCT GGATTCACCTTCAGT AATCATGCTATGCAC TGGGTCCGCCAGGCT CCAGGCAAGGGGCTG GAGTGGGTGGCAGTT ATATCATATGATGGC GAGAACACATATTAT GCAGACTCCATTGAG GGCCGATTCACCATT TCCAGAGACAATTTC AAGAACACACTCTTT CTACAAATGTACAGC CTGACAGCTGATGAC ACGGCTATGTACTTC TGTGCGAGAGGGGGC CGTCGGGGCACTTC ACCTCATACTACCTT GACTACTGGGGCCAG GGAACCCTGGTCACC GTCTCCTCG | 54 |
| Light chain nucleotide sequence with signal peptide | ATGGACATGCGGGTG CCCGCCCAGCTGCTG GGCCTGCTGCTGCTG TGGTTCCCCGGCTCT AGATGCGACATCCAG ATGACCCAGTCTCCA TCCTCCCTGTCTGCA TCTGTAGGAGACAGA GTCACCATCACTTGC CGGGCAAGCCAGAAC ATAGACAAGTACTTA AATTGGTATCAGCAG ATACCGGGGAAAGCC CCTAAGCTCCTGATC TATGCTGCATCGAGT TTGCACAGTGGGGTC CCATCAAGGTTCAGT GGCAGTGGATCTGGG ACAGATTTCTCTCTC ACCATCAGCAGTCTG CAACCTGAAGATTTT GCAATTTACTACTGT CAACAGAGTTACAGT | 55 |

TABLE 13-continued

Nucleotide sequences encoding DPR Ab-1

| | Nucleotide sequence | SEQ ID NO: |
|---|---|---|
| | TCCTTCCGGACGTTC<br>GGCCAAGGGACCAAG<br>CTGGAGATCAAACGT<br>ACGGTGGCTGCACCA<br>TCTGTCTTCATCTTC<br>CCGCCATCTGATGAG<br>CAGTTGAAATCTGGA<br>ACTGCCTCTGTTGTG<br>TGCCTGCTGAATAAC<br>TTCTATCCCAGAGAG<br>GCCAAAGTACAGTGG<br>AAGGTGGATAACGCC<br>CTCCAATCGGGTAAC<br>TCCCAGGAGAGTGTC<br>ACAGAGCAGGACAGC<br>AAGGACAGCACCTAC<br>AGCCTCAGCAGCACC<br>CTGACGCTGAGCAAA<br>GCAGACTACGAGAAA<br>CACAAAGTCTACGCC<br>TGCGAAGTCACCCAT<br>CAGGGCCTGAGTTCG<br>CCCGTCACAAAGAGC<br>TTCAACAGGGGAGAG<br>TGTTGA | |
| Light chain nucleotide sequence (mature, without signal peptide) | GACATCCAGATGACC<br>CAGTCTCCATCCTCC<br>CTGTCTGCATCTGTA<br>GGAGACAGAGTCACC<br>ATCACTTGCCGGGCA<br>AGCCAGAACATAGAC<br>AAGTACTTAAATTGG<br>TATCAGCAGATACCG<br>GGGAAAGCCCCTAAG<br>CTCCTGATCTATGCT<br>GCATCGAGTTTGCAC<br>AGTGGGGTCCCATCA<br>AGGTTCAGTGGCAGT<br>GGATCTGGGACAGAT<br>TTCTCTCTCACCATC<br>AGCAGTCTGCAACCT<br>GAAGATTTTGCAATT<br>TACTACTGTCAACAG<br>AGTTACAGTTCCTTC<br>CGGACGTTCGGCCAA<br>GGGACCAAGCTGGAG<br>ATCAAACGTACGGTG<br>GCTGCACCATCTGTC<br>TTCATCTTCCCGCCA<br>TCTGATGAGCAGTTG<br>AAATCTGGAACTGCC<br>TCTGTTGTGTGCCTG<br>CTGAATAACTTCTAT<br>CCCAGAGAGGCCAAA<br>GTACAGTGGAAGGTG<br>GATAACGCCCTCCAA<br>TCGGGTAACTCCCAG<br>GAGAGTGTCACAGAG<br>CAGGACAGCAAGGAC<br>AGCACCTACAGCCTC<br>AGCAGCACCCTGACG<br>CTGAGCAAAGCAGAC<br>TACGAGAAACACAAA<br>GTCTACGCCTGCGAA<br>GTCACCCATCAGGGC<br>CTGAGTTCGCCCGTC<br>ACAAAGAGCTTCAAC<br>AGGGGAGAGTGTTGA | 56 |
| Light chain constant domain nucleotide sequence | CGTACGGTGGCTGCA<br>CCATCTGTCTTCATC<br>TTCCCGCCATCTGAT<br>GAGCAGTTGAAATCT<br>GGAACTGCCTCTGTT<br>GTGTGCCTGCTGAAT<br>AACTTCTATCCCAGA<br>GAGGCCAAAGTACAG<br>TGGAAGGTGGATAAC<br>GCCCTCCAATCGGGT<br>AACTCCCAGGAGAGT<br>GTCACAGAGCAGGAC<br>AGCAAGGACAGCACC<br>TACAGCCTCAGCAGC<br>ACCCTGACGCTGAGC<br>AAAGCAGACTACGAG<br>AAACACAAAGTCTAC<br>GCCTGCGAAGTCACC<br>CATCAGGGCCTGAGT<br>TCGCCCGTCACAAAG<br>AGCTTCAACAGGGGA<br>GAGTGTTGA | 57 |
| Light chain variable region nucleotide sequence | GACATCCAGATGACC<br>CAGTCTCCATCCTCC<br>CTGTCTGCATCTGTA<br>GGAGACAGAGTCACC<br>ATCACTTGCCGGGCA<br>AGCCAGAACATAGAC<br>AAGTACTTAAATTGG<br>TATCAGCAGATACCG<br>GGGAAAGCCCCTAAG<br>CTCCTGATCTATGCT<br>GCATCGAGTTTGCAC<br>AGTGGGGTCCCATCA<br>AGGTTCAGTGGCAGT<br>GGATCTGGGACAGAT<br>TTCTCTCTCACCATC<br>AGCAGTCTGCAACCT<br>GAAGATTTTGCAATT<br>TACTACTGTCAACAG<br>AGTTACAGTTCCTTC<br>CGGACGTTCGGCCAA<br>GGGACCAAGCTGGAG<br>ATCAAA | 58 |

The present invention also includes fragments of the polynucleotides of the invention, as described elsewhere. Additionally polynucleotides which encode fusion polynucleotides, Fab fragments, and other biotechnological derivatives, as described herein, are also contemplated by the invention.

In one embodiment, the present invention relates to a polynucleotide, optionally linked to heterologous nucleic acid, wherein (i) the polynucleotide encodes an immunoglobulin variable heavy chain with the VH-CDRs as defined in any one of the preceding items [1] to [10], and wherein the immunoglobulin variable heavy chain when paired with an immunoglobulin variable light chain comprising the amino acid sequence set forth in SEQ ID NO: 7 or 24 displays the binding characteristics of the subject antibody as illustrated in the Examples and recited in any one of the preceding items [1] to [36], and/or (ii) the polynucleotide encodes an immunoglobulin variable light chain with the VL-CDRs as defined in any one of the preceding items [1] to [10], and wherein the immunoglobulin variable light chain when paired with an immunoglobulin variable heavy chain comprising the amino acid sequence set forth in any one of SEQ ID NO: 2, 12, 15, 18 or 21 displays the binding characteristics of the subject antibody as illustrated in the Examples and recited in any one of the preceding items [1] to [36].

Furthermore, the present invention relates to a vector and vectors comprising one or more of those polynucleotides, optionally wherein the vector is an expression vector and the one or more polynucleotides are operably linked to expression control sequences. Furthermore, the present invention relates to host cells comprising one or more polynucleotides or a vector or vectors of the present invention as well as to a method of producing an anti-poly-(GA)-DPR antibody or DPR-binding fragment thereof, said method comprising culturing the host cell of the present invention under conditions allowing for expression of the anti-DPR antibody or DPR-binding fragment thereof; and isolating said anti-DPR antibody or DPR-binding fragment thereof from the culture.

The polynucleotides may be produced or manufactured by any method known in the art. For example, if the nucleotide sequence of the antibody is known, a polynucleotide encoding the antibody may be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or DPR-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, optionally poly $A^+$ RNA, isolated from, any tissue or cells expressing the DPR-specific antibody, such as B cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody, or DPR-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., Molecular Cloning, A Laboratory Manual, 2d Ed., Cold Spring Harbor Laboratory, Cold Spring Harbor, N.Y. (1990) and Ausubel et al., eds., Current Protocols in Molecular Biology, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides of the Present Invention

Following manipulation of the isolated genetic material to provide antibodies, or DPR-binding fragments, variants, or derivatives thereof of the invention, the polynucleotides encoding the antibodies are typically inserted in an expression vector for introduction into host cells that may be used to produce the desired quantity of antibody. Recombinant expression of an antibody, or fragment, derivative, or analog thereof, e.g., a heavy or light chain of an antibody which binds to a target molecule is described herein. Once a polynucleotide encoding an antibody molecule or a heavy or light chain of an antibody, or portion thereof (optionally containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operable linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses, and retroviruses. In general, vectors compatible with the instant invention will comprise a selection marker, appropriate restriction sites to facilitate cloning of the desired gene and the ability to enter and/or replicate in eukaryotic or prokaryotic cells. For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics), or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (optionally human) as discussed above. In one embodiment, this is accomplished using a proprietary expression vector of Biogens, Inc., referred to as NEOSPLA, and disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene, and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6N5-His, pVAX1, and pZeoSV2 (available from Invitrogen, San Diego, CA), and plasmid pCI (available from Promega, Madison, WI). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the antibodies, or DPR-binding fragments, variants, or derivatives thereof of the invention may be expressed using polycistronic constructs such as those disclosed in US patent application publication no. 2003-0157641 A1 and incorporated herein in its entirety. In these expression systems, multiple gene products of interest such as heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems may be used to effectively produce the full range of antibodies disclosed in the instant application. Therefore, in one embodiment the present invention provides a vector comprising the polynucleotide encoding at least the binding domain or variable region of an immunoglobulin chain of the antibody, optionally in combination with a polynucleotide that encodes the variable region of the other immunoglobulin chain of said binding molecule.

More generally, once the vector or DNA sequence encoding a monomeric subunit of the antibody has been prepared, the expression vector may be introduced into an appropriate host cell. Introduction of the plasmid into the host cell can be accomplished by various techniques well known to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells comprising a polynucleotide encoding an antibody of the invention, or a heavy or light chain thereof, or at least the binding domain or variable region of an immunoglobulin thereof, which optionally are operable linked to a heterologous promoter. In addition or alternatively the invention also includes host cells comprising a vector, as defined hereinabove, comprising a polynucleotide encoding at least the binding domain or variable region of an immunoglobulin chain of the antibody, optionally in combination with a polynucleotide that encodes the variable region of the other immunoglobulin chain of said binding molecule. In preferred embodiments for the expression of double-chained antibodies, a single vector or vectors encoding both the heavy and light chains may be co-expressed in the host cell for expression of the entire immunoglobulin molecule, as detailed below.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains may comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *Escherichia coli, Bacillus subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Optionally, bacterial cells such as *E. coli*, or optionally, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). CHO and 293 cells are particularly preferred. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11 (1977), 223), hypoxanthine-guanine phosphoribosyltransferase (Szybalska and Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan and Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann. Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., J. Mol. Biol. 150:1 (1981), which are incorporated by reference herein in their entireties. The expression levels of an antibody molecule can be increased by vector amplification, for a review; see Bebbington and Hentschel, The use of vectors based on gene amplification for the expression of cloned genes in mammalian cells in DNA cloning, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257.

In vitro production allows scale-up to give large amounts of the desired antibody. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-) affinity chromatography, e.g., after preferential biosynthesis of a synthetic hinge region polypeptide or prior to or subsequent to the HIC chromatography step described herein.

Genes encoding antibodies, or DPR-binding fragments, variants or derivatives thereof of the invention can also be expressed in non-mammalian cells such as bacteria or insect or yeast or plant cells. Bacteria which readily take up nucleic acids include members of the enterobacteriaceae, such as strains of *E. coli* or *Salmonella*; Bacillaceae, such as *B. subtilis*; Pneumococcus; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO 02/096948.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2 (1983), 1791), in which the antibody coding sequence may be ligated individually into the vector in frame with the lacZ coding region so that a fusion protein is produced; pIN vectors (Inouye and Inouye, Nucleic Acids Res. 13 (1985), 3101-3109; Van Heeke and Schuster, J. Biol. Chem. 24 (1989), 5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Alternatively, a preferred method for increasing the affinity of antibodies of the invention is disclosed in US patent publication 2002-0123057 A1. In one embodiment therefore, the present invention also provides a method for preparing an anti-DPR antibody or an antibody recognizing mutated and/or aggregated C9orf72-DPR species and/or fragments thereof or immunoglobulin chain(s) thereof, said method comprising:

(a) culturing the host cell as defined hereinabove, which cell comprised a polynucleotide or a vector as defined hereinbefore; and (b) isolating said antibody or immunoglobulin chain(s) thereof from the culture.

Furthermore, the present invention also relates to an antibody or immunoglobulin chain(s) thereof encoded by a polynucleotide as defined hereinabove or obtainable by said method for preparing an anti-DPR antibody or an antibody recognizing mutated and/or aggregated C9orf72-DPR species and/or fragments thereof or immunoglobulin chain(s) thereof.

V. Fusion Proteins and Conjugates of the Present Invention

In certain embodiments, the antibody polypeptide comprises an amino acid sequence or one or more moieties not normally associated with an antibody. Exemplary modifications are described in more detail below. For example, a single-chain Fv antibody fragment of the invention may comprise a flexible linker sequence, or may be modified to add a functional moiety (e.g., PEG, a drug, a toxin, or a label such as a fluorescent, radioactive, enzyme, nuclear magnetic, heavy metal and the like).

An antibody polypeptide of the invention may comprise, consist essentially of, or consist of a fusion protein. Fusion proteins are chimeric molecules which comprise, for example, an immunoglobulin DPR-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or DPR-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO 92/08495; WO 91/14438; WO 89/12624; U.S. Pat. No. 5,314,995; and European patent application EP 0 396 387.

Antibodies, or DPR-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., Proteins—Structure And Molecular Properties, T. E. Creighton, W. H. Freeman and Company, New York 2nd Ed., (1993); Posttranslational Covalent Modification Of Proteins, B. C. Johnson, Ed., Academic Press, New York, (1983) 1-12; Seifter et al., Meth. Enzymol. 182 (1990), 626-646; Rattan et al., Ann. NY Acad. Sci. 663 (1992), 48-62).

As discussed elsewhere herein, antibodies, or DPR-binding fragments, variants, or derivatives thereof of the invention may be fused to heterologous polypeptides to increase the in vivo half-life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or DPR-binding fragments, synthetic variants, or biotechnological derivatives thereof of the invention can be fused to marker sequences, such as a peptide to facilitate their purification or detection. In preferred embodiments, the marker amino acid sequence is a hexa-histidine peptide (HIS) (SEQ ID NO: 84), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767), GST, c-myc and the "flag" tag; see, e.g., Bill Brizzard, BioTechniques 44 (2008) 693-695 for a review of epitope tagging techniques, and Table 1 on page 694 therein listing the most common epitope tags usable in the present invention, the subject matter of which is hereby expressly incorporated by reference.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression, which is performed as described herein before.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or DPR-binding fragments, variants, or derivatives thereof of the invention can be labeled or conjugated either before or after purification, when purification is performed. In particular, antibodies, or DPR-binding fragments, variants, or derivatives thereof of the invention may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared, e.g., by reacting a DPR-binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, optionally fluorescein-isothiocyanate. Conjugates of the antibodies, or DPR-binding fragments, variants or derivatives thereof of the invention are prepared in an analogous manner.

The present invention further encompasses antibodies, or DPR-binding fragments, variants, or derivatives thereof of the invention conjugated to a diagnostic or therapeutic agent. The antibodies can be used diagnostically to, for example, demonstrate presence of a DPRs to indicate the risk of getting a disease or disorder associated with DPRs, optionally associated with mutated C9orf72 forming DPRs, i.e. C9orf72-DPRs, to monitor the development or progression of such a disease, i.e. a disease showing the occurrence of, or related to DPRs or aggregated forms thereof, or as part of a clinical testing procedure to, e.g., determine the efficacy of a given treatment and/or prevention regimen. In one embodiment thus, the present invention relates to an antibody, which is detectably labeled. Furthermore, in one embodiment, the present invention relates to an antibody, which is attached to a drug. Detection can be facilitated by coupling the antibody, or DPR-binding fragment, variant, or derivative thereof to a detectable substance. The detectable substances or label may be in general an enzyme; a heavy metal, optionally gold; a dye, optionally a fluorescent or luminescent dye; or a radioactive label.

Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc. Therefore, in one embodiment the present invention provides a detectably labeled antibody, wherein the detectable label is selected from the group consisting of an enzyme, a radioisotope, a fluorophore and a heavy metal.

An antibody, or DPR-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or DPR-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, (ed.), Enzyme Immunoassay, CRC Press, Boca Raton, Fla., (1980); Ishikawa, et al., (eds.), Enzyme Immunoassay, Kgaku Shoin, Tokyo (1981). The enzyme, which is bound to the antibody, will react with an appropriate substrate, optionally a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or DPR-binding fragment, variant, or derivative thereof, it is possible to detect the antibody through the use of a radioimmunoassay (RIA) (see, for example, Weintraub, B., Principles of Radioimmunoassays, Seventh Training Course on Radioligand Assay Techniques, The Endocrine Society, (March, 1986)), which is incorporated by reference herein). The radioactive isotope can be detected by means including, but not limited to, a gamma counter, a scintillation counter, or autoradiography.

An antibody, or DPR-binding fragment, variant, or derivative thereof can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or DPR-binding fragment, variant, or derivative thereof are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al. (eds.), Marcel Dekker, Inc., (1987) 623-53; Thorpe, "Antibody Carriers Of Cytotoxic Agents In Cancer Therapy: A Review", in Monoclonal Antibodies '84: Biological And Clinical Applications, Pinchera et al. (eds.), (1985) 475-506; "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press (1985) 303-16, and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

VI. Compositions and Methods of Use of the Present Invention

The present invention relates to compositions comprising the aforementioned DPR-binding molecule of the present invention, e.g., antibody or DPR-binding fragment, variant or biotechnological derivative thereof, or the polynucleotide(s), vector(s) or cell of the invention as defined hereinbefore. In one embodiment, the composition of the present invention is a pharmaceutical composition and further comprises a pharmaceutically acceptable carrier. Furthermore, the pharmaceutical composition of the present invention may comprise further agents such as interleukins or interferons depending on the intended use of the pharmaceutical composition. For use in the treatment of a disease or disorder showing the occurrence of, or related to DPRs or aggregated forms thereof, in particular C9orf72-DPRs, such as FTLD, the additional agent may be selected from the group consisting of small organic molecules, anti-DPR antibodies, and combinations thereof. Hence, in a particular preferred embodiment the present invention relates to the use of the DPR-binding molecule, e.g., antibody or DPR-binding fragment thereof of the present invention or of a binding molecule having substantially the same binding specificities of any one thereof, the polynucleotide, the vector or the cell of the present invention for the preparation of a pharmaceutical or diagnostic composition for prophylactic and therapeutic treatment of a disease or disorder associated with DPR proteins, monitoring the progression of a disease or disorder associated with DPR protein and/or aggregated C9orf72 or a response to a DPR treatment in a subject or for determining a subject's risk for developing a disease or disorder associated with DPR protein and/or aggregated C9orf72-DPRs.

Hence, in one embodiment the present invention relates to a method of treating a disease or disorder characterized by abnormal accumulation and/or deposition of DPRs and DPR proteins such as aggregated C9orf72 due to C9orf72-DPRs, which method comprises administering to a subject in need thereof a therapeutically effective amount of any one of the afore-described DPR-binding molecules, antibodies, polynucleotides, vectors or cells of the instant invention.

A particular advantage of the therapeutic approach of the present invention lies in the fact that the recombinant antibodies of the present invention are derived from B cells or memory B cells from healthy human subjects with no signs or symptoms of a disease, e.g. carrying an asymptomatic mutation and/or mutations, showing the occurrence of, or related to DPRs or aggregated forms thereof and thus are, with a certain probability, capable of preventing a clinically manifest disease related to DPRs, e.g. mutated C9orf72 with expanded hexanucleotide repeats resulting in the formation of dipeptide repeat (DPR) in the C9orf72 protein and aggregated C9orf72 due to C9orf72-DPRs, or of diminishing the risk of the occurrence of the clinically manifest disease or disorder, or of delaying the onset or progression of the clinically manifest disease or disorder. Typically, the antibodies of the present invention also have already successfully gone through somatic maturation, i.e. the optimization with respect to selectivity and effectiveness in the high affinity binding to the target DPR molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human-derived anti-DPR antibodies of the present invention, both its high target structure-specific affinity as therapeutic agent and its decreased probability of side effects significantly increase its clinical probability of success.

The present invention also provides a pharmaceutical and diagnostic, respectively, pack or kit comprising one or more containers filled with one or more of the above described ingredients, e.g. anti-DPR antibody, binding fragment, biotechnological derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of a disease or disorder which is accompanied with the presence of DPRs, and in particular applicable for the treatment of disorders generally characterized by presence of DPRs. In particular, the composition is useful in the treatment of disorders which are related to DPR aggregation, for example mutated C9orf72 with expanded hexanucleotide repeats resulting in the formation of aggregated C9orf72 due to C9orf72-DPRs. Diseases and/or disorders associated with DPRs comprise but are not limited to Frontotemporal lobar degeneration (FTLD), amyotrophic lateral sclerosis (ALS), FTLD-ALS, and/or spinocerebellar ataxia type 36.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, intranasal, topical or intradermal administration or spinal or brain delivery. Aerosol formulations such as nasal spray formulations include purified aqueous or other solutions of the active agent with preservative agents and isotonic agents. Such formulations are optionally adjusted to a pH and isotonic state compatible with the nasal mucous membranes. Formulations for rectal or vaginal administration may be presented as a suppository with a suitable carrier.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, optionally at least 3, 10 or 30 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive or alternate days or 30 mg/kg weekly; see also Example 18. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline, and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like. Furthermore, the pharmaceutical composition of the invention may comprise further agents such as dopamine or psychopharmacologic drugs, depending on the intended use of the pharmaceutical composition.

Furthermore, in a preferred embodiment of the present invention the pharmaceutical composition may be formulated as a vaccine, for example, if the pharmaceutical composition of the invention comprises an anti-DPR antibody or DPR-binding fragment, or synthetic or biotechnological variant or derivative thereof for passive immunization. As mentioned in the background section aggregated DPR species are a major trigger for diseases and/or disorders such as FTLD and ALS. Accordingly, it is prudent to expect that passive immunization with human-derived anti-DPR antibodies and equivalent DPR-binding molecules of the present invention will help to circumvent several adverse effects of active immunization therapy concepts and lead to a reduced aggregation of DPRs. Therefore, the present anti-DPR antibodies and their equivalents of the present invention will be particularly useful as a vaccine for the prevention or amelioration of diseases or disorders showing the presence of, or caused by DPRs or aggregated forms thereof, in particular C9orf72-DPRs, such as FTLD.

In one embodiment, it may be beneficial to use recombinant Fab (rFab) and single chain fragments (scFvs) of the antibody of the present invention, which might more readily penetrate a cell membrane. For example, Robert et al., Protein Eng. Des. Sel. (2008); S1741-0134, published online ahead, describe the use of chimeric recombinant Fab (rFab) and single chain fragments (scFvs) of monoclonal antibody WO-2 which recognizes an epitope in the N-terminal region of Abeta. The engineered fragments were able to (i) prevent amyloid fibrillization, (ii) disaggregate preformed Abeta1-42 fibrils and (iii) inhibit Abeta1-42 oligomer-mediated neurotoxicity in vitro as efficiently as the whole IgG molecule. The perceived advantages of using small Fab and scFv engineered antibody formats which lack the effector function include more efficient passage across the blood-brain barrier and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

In a further embodiment, co-administration or sequential administration of other antibodies useful for treating a disease, disorder, or symptoms related to the occurrence of DPRs, in particular aggregated DPRs such as C9orf72-DPRs may be desirable. In one embodiment, the additional antibody is comprised in the pharmaceutical composition of the present invention. Examples of antibodies which can be used to treat a subject include, but are not limited to, antibodies targeting CD33, SGLT2, IL-6, and IL-1.

In a further embodiment, co-administration or sequential administration of other agents useful for treating a disease, disorder, or symptoms related to DPRs, in particular aggregated DPRs such as mutated C9orf72, i.e. C9orf72-DPRs may be desirable. In one embodiment, the additional agent is comprised in the pharmaceutical composition of the present invention. Examples of agents which can be used to treat a subject include, but are not limited to: VMAT2 inhibitors targeting involuntary muscle movements such as anti-inflammatory agents such as diflusinal, corticosteroids, 2-(2,6-dichloranilino) phenylacetic acid (diclofenac), iso-butyl-propanoic-phenolic acid (ibuprofen); diuretics, Epi-gallocatechin gallate, Melphalan hydrochloride, dexamethasone, Bortezomib, Bortezomib-Melphalan, Bortezomib-dexamethasone, Melphalan-dexamethasone, Bortezomib-Melphalan-dexamethasone; antidepressants, antipsychotic drugs, neuroleptics, antidementiva (e.g. the NMDA-rezeptor antagonist memantine), acetylcholinesterase inhibitors (e.g. Donepezil, HCl, Rivastigmine, Galantamine), glutamat-antagonists and other nootropics blood pressure medication (e.g. Dihydralazin, Methyldopa), cytostatics, glucocorticoides, angiotensin-converting-enzyme (ACE) inhibitors; anti-inflammatory agents or any combination thereof.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$.

From the foregoing, it is evident that the present invention encompasses any use of an DPR-binding molecule comprising at least the CDRs of the above described antibody and variants thereof, in particular for diagnosing and/or treatment of a disease or disorder related to DPRs, in particular aggregated DPR species such as C9orf72-DPRs such as FTLD. Optionally, said binding molecule is an antibody of the present invention or a biotechnological derivative thereof.

In another embodiment the present invention relates to a diagnostic composition comprising any one of the above described DPR-binding molecules, antibodies, DPR-binding fragments, polynucleotides, vectors or cells of the invention and optionally suitable means for detection such as reagents conventionally used in immuno- or nucleic acid-based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry, and the Western blot assay. The antibodies of the invention can be bound to many different carriers and used to isolate cells specifically bound thereto. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the DPR-binding molecules, in particular antibodies of the present invention may also be used in a method for the diagnosis of a disease or disorder in an individual by obtaining a body fluid sample from the tested individual which may be a blood sample, a plasma sample, a serum sample, a lymph sample or any other body fluid sample, such as a saliva or a urine sample and contacting the body fluid sample with an antibody of the instant invention under conditions enabling the formation of antibody-antigen complexes. The level of such complexes is then determined by methods known in the art, a level significantly higher than that formed in a control sample indicating the disease or disorder in the tested individual. In the same manner, the specific antigen bound by the antibodies of the invention may also be used. Thus, the present invention relates to an in vitro immunoassay comprising the binding molecule, e.g., antibody or DPR-binding fragment thereof of the invention.

In a further embodiment of the present invention the DPR-binding molecules, in particular antibodies of the present invention may also be used in a method for the diagnosis of a disease or disorder in an individual by obtaining a biopsy from the tested individual. In this context, the present invention also relates to means specifically designed for this purpose. For example, an antibody-based array may be used, which is for example loaded with antibodies or equivalent DPR-binding molecules of the present invention which specifically recognize DPRs. Design of microarray immunoassays is summarized in Kusnezow et al., Mol. Cell Proteomics 5 (2006), 1681-1696. Accordingly, the present invention also relates to microarrays loaded with DPR-binding molecules of the present invention.

In one embodiment, the present invention relates to a method of diagnosing a disease or disorder related to DPRs, in particular aggregated DPR species such as C9orf72-DPRs in a subject, the method comprising determining the presence of DPRs and aggregated DPRs, respectively, in a sample from the subject to be diagnosed with at least one antibody of the present invention, a DPR-binding fragment thereof or an DPR-binding molecule having substantially the same binding specificities of any one thereof, wherein the presence of DPRs or pathologically aggregated forms thereof, optionally of C9orf72-DPRs is indicative for FTLD and/or ALS, and an increase of the level of the DPRs or pathologically aggregated forms thereof, in particular of C9orf72-DPRs in comparison to the level of the physiological C9orf72, i.e. which does not show a translation of the repeat region into DPR proteins, is indicative for progression of FTLD and/or ALS in said subject.

The subject to be diagnosed may be asymptomatic or preclinical for the disease. Optionally, the control subject has a disease associated with DPRs, aggregated DPRs, and/or optionally C9orf72-DPRs, e.g. FTLD, ALS and FTLD-ALS and others, as described above, wherein a similarity between the level of DPRs, e.g. aggregated C9orf72-DPRs and the reference standard indicates that the subject to be diagnosed has a FTLD, ALS and/or FTLD-ALS or is at risk to develop a disease and/or disorder associated with DPR aggregation. Alternatively, or in addition as a second control the control subject does not have a DPR aggregation, wherein a difference between the level of physiological C9orf72 or another protein which is prone to have DPRs inserted due to mutation in its gene like the mutated C9orf72 gene and/or aggregated C9orf72-DPRs and the reference standard indicates that the subject to be diagnosed has a disease and/or disorder associated with DPRs, such as FTLD, ALS and/or FTLD-ALS or is at risk to develop a disease and/or disorder associated with DPRs. Optionally, the subject to be diagnosed and the control subject(s) are age-matched. The sample to be analyzed may be any body fluid suspected to contain pathologically DPR proteins such as aggregated C9orf72-DPRs, for example a blood, blood plasma, blood serum, urine, peritoneal fluid, saliva or cerebral spinal fluid (CSF).

The level of physiological C9orf72 or like protein and/or aggregated DPRs such as C9orf72-DPRs may be assessed by any suitable method known in the art comprising, e.g., analyzing DPRs and/or the protein incorporating DPRs such as C9orf72 by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. Optionally, said in vivo imaging of DPRs comprises scintigraphy, positron emission tomography (PET), single photon emission tomography (SPECT), near infrared (NIR) optical imaging or magnetic resonance imaging (MRI).

In one embodiment thus, an antibody of the present invention, the polynucleotide(s), the vector(s) or the cell as defined hereinabove or a pharmaceutical or diagnostic composition comprising any one thereof is provided for use in prophylactic treatment, therapeutic treatment, and/or monitoring the progression or a response to treatment of a disease or disorder related to DPR protein or aggregated forms thereof. Thus, the present invention also relates to a method of diagnosing or monitoring the progression of a disease or disorder related to DPR proteins (such as FTLD and ALS) in a subject, the method comprising determining the presence of DPR proteins in a sample from the subject to be diagnosed with at least one antibody of the present invention or a DPR-binding molecule having substantially the same binding specificities of any one thereof, wherein the presence of DPRs such as in mutated C9orf72 and aggregated C9orf72-DPR species is indicative for the disease or disorder. In one embodiment said method of diagnosing or monitoring the progression of DPR associated diseases and/or disorders in a subject is provided, the method comprising determining the presence DPRs such as in mutated C9orf72 and aggregated forms thereof in a sample from the subject to be diagnosed with at least one antibody of the present invention, wherein the presence of DPRs such as mutated C9orf72 and/or aggregated C9orf72-DPRs is indicative for presymptomatic, prodromal or clinical diseases and/or disorders associated with DPRs, an increase of the level of DPR aggregates, in particular C9orf72-DPRs in comparison to the level of the physiological C9orf72 without DPRs or in comparison to a reference sample derived from a healthy control subject or a control sample from the same subject is indicative for progression of presymptomatic, prodromal or established diseases and/or disorders associated with DPRs such as FTLD and ALS. It would be appreciated by any person skilled in the art that in one embodiment said method is used as well for the diagnosing or monitoring the progression of any other disease or disorder from the group of disorders related to DPRs and proteins which contain DPRs, respectively, as defined hereinabove.

As indicated above, the antibodies of the present invention may be used not only in vitro but in vivo as well, wherein besides diagnostic, therapeutic applications as well may be pursued. In one embodiment thus, the present invention also relates to a DPR-binding molecule comprising the CDRs an antibody of the present invention for the preparation of a composition for in vivo detection of or targeting a therapeutic and/or diagnostic agent to DPR, optionally C9orf72-DPRs in the human or animal body. Potential therapeutic and/or diagnostic agents may be chosen from the nonexhaustive enumerations of the therapeutic agents useful in treatment of diseases and/or disorders associated with DPRs and potential labels as indicated hereinbefore. In respect of the in vivo imaging, in one preferred embodiment the present invention provides said DPR-binding molecule comprising the CDRs of an antibody of the present invention, wherein said in vivo imaging comprises scintigraphy, positron emission tomography (PET), single photon emission tomography (SPECT), near infrared (NIR) optical imaging or magnetic resonance imaging (MRI). In a further embodiment the present invention also provides said DPR-binding molecule comprising the CDRs of an antibody of the present invention, or said molecule for the preparation of a composition for the above specified in vivo imaging methods, for the use in the method of diagnosing or monitoring the progression of a disease or disorder related to DPR protein in a subject, as defined hereinabove.

In this context, the present invention also relates to a kit useful in the diagnosis or monitoring the progression of diseases and/or disorders associated with DPRs and DPR containing proteins, said kit comprising at least one antibody of the present invention or a DPR-binding molecule having substantially the same binding specificities of any one thereof, the polynucleotide, the vector or the cell and/or the peptide as respectively defined hereinbefore, optionally with reagents and/or instructions for use.

Provided herein are compositions, methods, and/or uses described by the following numbered paragraphs:

1. An anti-DPR antibody or fragment thereof comprising
   (i) a heavy chain having the amino acid sequence of SEQ ID NO: 38 (or an amino acid sequence at least 95%, e.g., 95%, 96%, 97%, 98%, 99%, or 100% identical to SEQ ID NO: 38); and
   (ii) a light chain having the amino acid sequence of SEQ ID NO: 42 (or an amino acid sequence at least 95%, e.g., 95%, 96%, 97%, 98%, 99%, or 100% identical to SEQ ID NO: 42).

1a. An anti-DPR antibody or fragment thereof (e.g., that binds, e.g., binds specifically and/or with high affinity, to, a poly-(GA)n repeat, e.g., a poly-(GA)n repeat described herein, e.g., poly-(GA)$_6$-15) (SEQ ID NO: 83), wherein the anti-DPR antibody or fragment thereof comprises:
   (i) a heavy chain comprising, consisting of, or consisting essentially of the amino acid sequence of SEQ ID NO: 37 or 38 (or an amino acid sequence at least 95%, e.g., 95%, 96%, 97%, 98%, 99%, or 100% identical to SEQ ID NO: 37 of 38),
      optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
   (ii) a heavy chain constant domain comprising, consisting of, or consisting essentially of the amino acid sequence of SEQ ID NO: 39 (or an amino acid sequence at least 95%, e.g., 95%, 96%, 97%, 98%, 99%, or 100% identical to SEQ ID NO: 39),
      optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
   (iii) a heavy chain variable region amino acid sequence comprising, consisting of, or consisting essentially of SEQ ID NO: 40 (or an amino acid sequence at least 95%, e.g., 95%, 96%, 97%, 98%, 99%, or 100% identical to SEQ ID NO: 40),
      optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
   (iv) a light chain amino acid sequence comprising, consisting of, or consisting essentially of SEQ ID NO: 41 or 42 (or an amino acid sequence at least 95%, e.g., 95%, 96%, 97%, 98%, 99%, or 100% identical to SEQ ID NO: 41 or 42),
      optionally wherein the light chain amino acid sequence is no more than 214 amino acids in length, and/or wherein the light chain variable region amino acid sequence is no more than 107 amino acids in length;
   (v) a light chain constant domain amino acid sequence comprising, consisting of, or consisting essentially of SEQ ID NO: 43 (or an amino acid sequence at least 95%, e.g., 95%, 96%, 97%, 98%, 99%, or 100% identical to SEQ ID NO: 43),
      optionally wherein the light chain amino acid sequence is no more than 214 amino acids in length, and/or wherein the light chain variable region amino acid sequence is no more than 107 amino acids in length;
   (vi) a light chain variable region amino acid sequence comprising, consisting of, or consisting essentially of SEQ ID NO: 44 (or an amino acid sequence at least 95%, e.g., 95%, 96%, 97%, 98%, 99%, or 100% identical to SEQ ID NO: 44),
      optionally wherein the light chain amino acid sequence is no more than 214 amino acids in length, and/or wherein the light chain variable region amino acid sequence is no more than 107 amino acids in length;
   (vii) a heavy chain variable region comprising a CDR1 amino acid sequence of SEQ ID NO: 45 (or an amino acid sequence at least 95%, e.g., 95%, 96%, 97%, 98%, 99%, or 100% identical to SEQ ID NO: 45); a CDR2 amino acid sequence of SEQ ID NO: 46 (or an amino acid sequence at least 95%, e.g., 95%, 96%, 97%, 98%, 99%, or 100% identical to SEQ ID NO: 46), and a CDR3 amino acid sequence of SEQ ID NO: 47 (or an amino acid sequence at least 95%, e.g., 95%, 96%, 97%, 98%, 99%, or 100% identical to SEQ ID NO: 47),
      optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length; and/or
(viii) a light chain variable region comprising a CDR1 amino acid sequence of SEQ ID NO: 48 (or an amino acid sequence at least 95%, e.g., 95%, 96%, 97%, 98%, 99%, or 100% identical to SEQ ID NO: 48), a CDR2 amino acid sequence of SEQ ID NO: 49 (or an amino acid sequence at least 95%, e.g., 95%, 96%, 97%, 98%, 99%, or 100% identical to SEQ ID NO: 49), and a CDR3 amino acid sequence of SEQ ID NO: 50 (or an amino acid sequence at least 95%, e.g., 95%, 96%, 97%, 98%, 99%, or 100% identical to SEQ ID NO: 50), optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length, and/or optionally wherein the light chain amino acid sequence is no more than 214 amino acids in length, and/or wherein the light chain variable region amino acid sequence is no more than 107 amino acids in length.

1b. The anti-DPR antibody or fragment thereof of any of paragraphs 1-1e, comprising a heterologous sequence, e.g., that is heterologous to the heavy chain, light chain, heavy chain variable region, heavy chain constant domain, light chain variable region, light chain constant domain, variable heavy CDRs, and/or variable light CDRs.

1c. The anti-DPR antibody or fragment thereof of paragraph 1b, wherein the heterologous sequence comprises an immunoglobulin heavy chain constant region, an immunoglobulin light chain constant region, or a heterologous mammalian secretory signal peptide.

1d. The anti-DPR antibody or fragment thereof of any of paragraphs 1-1c, comprising a polyethylene glycol or a detectable label, e.g., an enzyme, a radioisotope, a fluorescent compound, a chemiluminescent compound, a bioluminescent compound, or a heavy metal.

1e. The anti-DPR antibody or fragment thereof of any of paragraphs 1-1d, wherein the antibody or fragment thereof is selected from the group consisting of a Fab, a Fab', a F(ab')$_2$, a Fc, a Fv, a single-chain Fv (scFv), a single-chain antibody, and a disulfide-linked Fv (sdFv).

2. A nucleic acid molecule comprising:
(i) a nucleic acid sequence encoding a heavy chain of an anti-DPR antibody having the amino acid sequence of SEQ ID NO: 38 (or an amino acid sequence at least 95%, e.g., 95%, 96%, 97%, 98%, 99%, or 100% identical to SEQ ID NO: 38); and/or
(ii) a nucleic acid sequence encoding a light chain of an anti-DPR antibody having the amino acid sequence of SEQ ID NO: 42 (or an amino acid sequence at least 95%, e.g., 95%, 96%, 97%, 98%, 99%, or 100% identical to SEQ ID NO: 42), optionally wherein the nucleic acid sequences (i) and (ii) are disposed on the same nucleic acid molecule or separate nucleic acid molecules.

2a. The nucleic acid molecule of paragraph 2, wherein the nucleic acid molecule comprises a cDNA and/or is operably linked to a heterologous nucleic acid, e.g., a heterologous signal peptide (e.g., a secretory signal peptide, e.g., a mammalian secretory signal peptide, e.g., a secretory signal peptide described herein) or a heterologous regulatory element (e.g., a heterologous enhancer, a ribosome binding site, a transcription terminator, or a heterologous promoter (e.g., a cytomegalovirus, simian virus 40, or retroviral promoter)).

2b. A nucleic acid molecule encoding one or more of the following (i)-(viii):
(i) a heavy chain comprising, consisting of, or consisting essentially of the amino acid sequence of SEQ ID NO: 37 or 38 (or an amino acid sequence at least 95%, e.g., 95%, 96%, 97%, 98%, 99%, or 100% identical to SEQ ID NO: 37 of 38),
  optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
(ii) a heavy chain constant domain comprising, consisting of, or consisting essentially of the amino acid sequence of SEQ ID NO: 39 (or an amino acid sequence at least 95%, e.g., 95%, 96%, 97%, 98%, 99%, or 100% identical to SEQ ID NO: 39),
  optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
(iii) a heavy chain variable region amino acid sequence comprising, consisting of, or consisting essentially of SEQ ID NO: 40 (or an amino acid sequence at least 95%, e.g., 95%, 96%, 97%, 98%, 99%, or 100% identical to SEQ ID NO: 40),
  optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
(iv) a light chain amino acid sequence comprising, consisting of, or consisting essentially of SEQ ID NO: 41 or 42 (or an amino acid sequence at least 95%, e.g., 95%, 96%, 97%, 98%, 99%, or 100% identical to SEQ ID NO: 41 or 42),
  optionally wherein the light chain amino acid sequence is no more than 214 amino acids in length, and/or wherein the light chain variable region amino acid sequence is no more than 107 amino acids in length;
(v) a light chain constant domain amino acid sequence comprising, consisting of, or consisting essentially of SEQ ID NO: 43 (or an amino acid sequence at least 95%, e.g., 95%, 96%, 97%, 98%, 99%, or 100% identical to SEQ ID NO: 43),
  optionally wherein the light chain amino acid sequence is no more than 214 amino acids in length, and/or wherein the light chain variable region amino acid sequence is no more than 107 amino acids in length;
(vi) a light chain variable region amino acid sequence comprising, consisting of, or consisting essentially of SEQ ID NO: 44 (or an amino acid sequence at least 95%, e.g., 95%, 96%, 97%, 98%, 99%, or 100% identical to SEQ ID NO: 44),
optionally wherein the light chain amino acid sequence is no more than 214 amino acids in length, and/or wherein the light chain variable region amino acid sequence is no more than 107 amino acids in length;
(vii) a heavy chain variable region comprising a CDR1 amino acid sequence of SEQ ID NO: 45 (or an amino acid sequence at least 95%, e.g., 95%, 96%, 97%, 98%, 99%, or 100% identical to SEQ ID NO: 45); a CDR2 amino acid sequence of SEQ ID NO: 46 (or an amino acid sequence at least 95%, e.g., 95%, 96%, 97%, 98%, 99%, or 100% identical to SEQ ID NO: 46), and a CDR3 amino acid sequence of SEQ ID NO: 47 (or an amino acid sequence at least 95%, e.g., 95%, 96%, 97%, 98%, 99%, or 100% identical to SEQ ID NO: 47),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
and/or
(viii) a light chain variable region comprising a CDR1 amino acid sequence of SEQ ID NO: 48 (or an amino acid sequence at least 95%, e.g., 95%, 96%, 97%, 98%, 99%, or 100% identical to SEQ ID NO: 48), a CDR2 amino acid sequence of SEQ ID NO: 49 (or an amino acid sequence at least 95%, e.g., 95%, 96%, 97%, 98%, 99%, or 100% identical to SEQ ID NO: 49), and a CDR3 amino acid sequence of SEQ ID NO: 50 (or an amino acid sequence at least 95%, e.g., 95%, 96%, 97%, 98%, 99%, or 100% identical to SEQ ID NO: 50),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length, and/or optionally wherein the light chain amino acid sequence is no more than 214 amino acids in length, and/or wherein the light chain variable region amino acid sequence is no more than 107 amino acids in length.

3. A nucleic acid molecule comprising one or more of the nucleotide sequences of SEQ ID NOs: 51-58 (or an amino acid sequence at least 95%, e.g., 95%, 96%, 97%, 98%, 99%, or 100% identical to SEQ ID NOs: 51-58).

3a. One or more nucleic acid molecules encoding the antibody or fragment thereof any of paragraphs 1-1e.

3b. A cDNA comprising the nucleic acid molecule(s) of any of paragraphs 2-3a.

3c. A cDNA comprising a polynucleotide encoding:
(i) a heavy chain comprising, consisting of, or consisting essentially of the amino acid sequence of SEQ ID NO: 37 or 38 (or an amino acid sequence at least 95%, e.g., 95%, 96%, 97%, 98%, 99%, or 100% identical to SEQ ID NO: 37 of 38),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
(ii) a heavy chain constant domain comprising, consisting of, or consisting essentially of the amino acid sequence of SEQ ID NO: 39 (or an amino acid sequence at least 95%, e.g., 95%, 96%, 97%, 98%, 99%, or 100% identical to SEQ ID NO: 39),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
(iii) a heavy chain variable region amino acid sequence comprising, consisting of, or consisting essentially of SEQ ID NO: 40 (or an amino acid sequence at least 95%, e.g., 95%, 96%, 97%, 98%, 99%, or 100% identical to SEQ ID NO: 40),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
(iv) a light chain amino acid sequence comprising, consisting of, or consisting essentially of SEQ ID NO: 41 or 42 (or an amino acid sequence at least 95%, e.g., 95%, 96%, 97%, 98%, 99%, or 100% identical to SEQ ID NO: 41 or 42),
optionally wherein the light chain amino acid sequence is no more than 214 amino acids in length, and/or wherein the light chain variable region amino acid sequence is no more than 107 amino acids in length;
(v) a light chain constant domain amino acid sequence comprising, consisting of, or consisting essentially of SEQ ID NO: 43 (or an amino acid sequence at least 95%, e.g., 95%, 96%, 97%, 98%, 99%, or 100% identical to SEQ ID NO: 43),
optionally wherein the light chain amino acid sequence is no more than 214 amino acids in length, and/or wherein the light chain variable region amino acid sequence is no more than 107 amino acids in length;
(vi) a light chain variable region amino acid sequence comprising, consisting of, or consisting essentially of SEQ ID NO: 44 (or an amino acid sequence at least 95%, e.g., 95%, 96%, 97%, 98%, 99%, or 100% identical to SEQ ID NO: 44),
optionally wherein the light chain amino acid sequence is no more than 214 amino acids in length, and/or wherein the light chain variable region amino acid sequence is no more than 107 amino acids in length;

(vii) a heavy chain variable region comprising a CDR1 amino acid sequence of SEQ ID NO: 45 (or an amino acid sequence at least 95%, e.g., 95%, 96%, 97%, 98%, 99%, or 100% identical to SEQ ID NO: 45); a CDR2 amino acid sequence of SEQ ID NO: 46 (or an amino acid sequence at least 95%, e.g., 95%, 96%, 97%, 98%, 99%, or 100% identical to SEQ ID NO: 46), and a CDR3 amino acid sequence of SEQ ID NO: 47 (or an amino acid sequence at least 95%, e.g., 95%, 96%, 97%, 98%, 99%, or 100% identical to SEQ ID NO: 47), optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length; and/or (viii) a light chain variable region comprising a CDR1 amino acid sequence of SEQ ID NO: 48 (or an amino acid sequence at least 95%, e.g., 95%, 96%, 97%, 98%, 99%, or 100% identical to SEQ ID NO: 48), a CDR2 amino acid sequence of SEQ ID NO: 49 (or an amino acid sequence at least 95%, e.g., 95%, 96%, 97%, 98%, 99%, or 100% identical to SEQ ID NO: 49), and a CDR3 amino acid sequence of SEQ ID NO: 50 (or an amino acid sequence at least 95%, e.g., 95%, 96%, 97%, 98%, 99%, or 100% identical to SEQ ID NO: 50), optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length, and/or optionally wherein the light chain amino acid sequence is no more than 214 amino acids in length, and/or wherein the light chain variable region amino acid sequence is no more than 107 amino acids in length; and/or (ix) a heavy chain having the amino acid sequence of SEQ ID NO: 38 (or an amino acid sequence at least 95%, e.g., 95%, 96%, 97%, 98%, 99%, or 100% identical to SEQ ID NO: 38); and/or (x) a light chain having the amino acid sequence of SEQ ID NO: 42 (or an amino acid sequence at least 95%, e.g., 95%, 96%, 97%, 98%, 99%, or 100% identical to SEQ ID NO: 42).

4. A vector comprising the nucleic acid molecule(s) of any of paragraphs 2-3a or the cDNA of any of paragraphs 3b-3c.

4a. The vector of paragraphs 4, wherein the vector is an expression vector operably linked to a polynucleotide, wherein the polynucleotide encodes one or more of:

(i) a heavy chain comprising, consisting of, or consisting essentially of the amino acid sequence of SEQ ID NO: 37 or 38 (or an amino acid sequence at least 95%, e.g., 95%, 96%, 97%, 98%, 99%, or 100% identical to SEQ ID NO: 37 of 38),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;

(ii) a heavy chain constant domain comprising, consisting of, or consisting essentially of the amino acid sequence of SEQ ID NO: 39 (or an amino acid sequence at least 95%, e.g., 95%, 96%, 97%, 98%, 99%, or 100% identical to SEQ ID NO: 39),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;

(iii) a heavy chain variable region amino acid sequence comprising, consisting of, or consisting essentially of SEQ ID NO: 40 (or an amino acid sequence at least 95%, e.g., 95%, 96%, 97%, 98%, 99%, or 100% identical to SEQ ID NO: 40),
optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;

(iv) a light chain amino acid sequence comprising, consisting of, or consisting essentially of SEQ ID NO: 41 or 42 (or an amino acid sequence at least 95%, e.g., 95%, 96%, 97%, 98%, 99%, or 100% identical to SEQ ID NO: 41 or 42),
optionally wherein the light chain amino acid sequence is no more than 214 amino acids in length, and/or wherein the light chain variable region amino acid sequence is no more than 107 amino acids in length;

(v) a light chain constant domain amino acid sequence comprising, consisting of, or consisting essentially of SEQ ID NO: 43 (or an amino acid sequence at least 95%, e.g., 95%, 96%, 97%, 98%, 99%, or 100% identical to SEQ ID NO: 43),
optionally wherein the light chain amino acid sequence is no more than 214 amino acids in length, and/or wherein the light chain variable region amino acid sequence is no more than 107 amino acids in length;

(vi) a light chain variable region amino acid sequence comprising, consisting of, or consisting essentially of SEQ ID NO: 44 (or an amino acid sequence at least 95%, e.g., 95%, 96%, 97%, 98%, 99%, or 100% identical to SEQ ID NO: 44),
optionally wherein the light chain amino acid sequence is no more than 214 amino acids in length, and/or wherein the light chain variable region amino acid sequence is no more than 107 amino acids in length;

(vii) a heavy chain variable region comprising a CDR1 amino acid sequence of SEQ ID NO: 45 (or an amino acid sequence at least 95%, e.g., 95%, 96%, 97%, 98%, 99%, or 100% identical to SEQ ID NO: 45); a CDR2 amino acid sequence of SEQ ID NO: 46 (or an amino acid sequence at least 95%, e.g., 95%, 96%, 97%, 98%, 99%, or 100% identical to SEQ ID NO: 46), and a CDR3 amino acid sequence of SEQ ID NO: 47 (or an amino acid sequence at least 95%, e.g., 95%, 96%, 97%, 98%, 99%, or 100% identical to SEQ ID NO: 47), optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length;
and/or
  (viii) a light chain variable region comprising a CDR1 amino acid sequence of SEQ ID NO: 48 (or an amino acid sequence at least 95%, e.g., 95%, 96%, 97%, 98%, 99%, or 100% identical to SEQ ID NO: 48), a CDR2 amino acid sequence of SEQ ID NO: 49 (or an amino acid sequence at least 95%, e.g., 95%, 96%, 97%, 98%, 99%, or 100% identical to SEQ ID NO: 49), and a CDR3 amino acid sequence of SEQ ID NO: 50 (or an amino acid sequence at least 95%, e.g., 95%, 96%, 97%, 98%, 99%, or 100% identical to SEQ ID NO: 50), optionally wherein the heavy chain amino acid sequence (e.g., heavy chain mature sequence) is no more than 452 amino acids in length, and/or wherein heavy chain does not comprise a lysine residue at the C-terminal end of its amino acid sequence, and/or wherein the heavy chain has a glycine at the C-terminal end of its amino acid sequence, and/or wherein the heavy chain variable region amino acid sequence is no more than 123 amino acids in length, and/or optionally wherein the light chain amino acid sequence is no more than 214 amino acids in length, and/or wherein the light chain variable region amino acid sequence is no more than 107 amino acids in length; and/or
  (ix) a heavy chain having the amino acid sequence of SEQ ID NO: 38 (or an amino acid sequence at least 95%, e.g., 95%, 96%, 97%, 98%, 99%, or 100% identical to SEQ ID NO: 38); and/or
  (x) a light chain having the amino acid sequence of SEQ ID NO: 42 (or an amino acid sequence at least 95%, e.g., 95%, 96%, 97%, 98%, 99%, or 100% identical to SEQ ID NO: 42).

4b. The vector of any of paragraphs 4-4a, wherein the vector comprises the cDNA of any of paragraphs 3b-3c.

4c. The vector of any of paragraphs 4-4b, wherein the vector comprises a promoter (e.g., a heterologous promoter, e.g., a cytomegalovirus (e.g., cytomegalovirus immediate early promoter), simian virus 40, or retroviral promoter).

5. A host cell comprising (i) the nucleic acid molecule(s) of any of paragraphs 2-3a; (ii) the cDNA of any of paragraphs 3b-3c; or (iii) the vector of any of paragraphs 4-4c, optionally wherein the host cell is a mammalian host cell (e.g., a Chinese hamster ovary (CHO) cell, a HEK 293 cell, or a NSO cell).

6. Use of the nucleic acid molecule of any of paragraphs 2-3a, the cDNA of any of paragraphs 3b-3c, the vector of any of paragraphs 4-4c, or the host cell of paragraph 5, for the production of an anti-DPR antibody or fragment thereof.

7. A method of producing an anti-DPR antibody or fragment thereof comprising: (i) culturing the host cell of paragraph 5; and (ii) isolating the antibody or fragment thereof from the culture.

8. A composition, e.g., pharmaceutical composition, comprising the anti-DPR antibody or fragment thereof of any of paragraphs 1-1e, the nucleic acid molecule(s) of any of paragraphs 2-3a, the cDNA of any of paragraphs 3b-3c, the vector of any of paragraphs 4-4c, or the host cell of paragraph 5,
  optionally wherein the pharmaceutical composition comprises a pharmaceutically acceptable carrier,
  optionally wherein the pharmaceutical composition is suitable for intrathecal administration.

9. A method of treating a disorder associated with or caused by DPR-containing protein or aggregated forms thereof (e.g., amyotrophic lateral sclerosis (ALS), frontotemporal lobar degeneration (FTLD), or FTLD-ALS) in a subject in need thereof, comprising administering an anti-DPR antibody or fragment thereof described herein (e.g., the anti-DPR antibody or fragment thereof of any of paragraphs 1-1e) to the subject, thereby treating disorder (e.g., the ALS, FTLD, or FTLD-ALS) in the subject.

10. A method of preparing a pharmaceutical composition for use in the treatment of a disorder associated with or caused by DPR-containing protein or aggregated forms thereof (e.g., ALS, FTLD, or FTLD-ALS), comprising: (i) culturing the host cell of paragraph 5; (ii) isolating and/or purifying the antibody or fragment thereof from the culture to pharmaceutical grade; and (iii) mixing the antibody or fragment thereof with a pharmaceutically acceptable carrier.

11. The anti-DPR antibody or fragment thereof of any of paragraphs 1-1e, the nucleic acid molecule(s) of any of paragraphs 2-3a, the cDNA of any of paragraphs 3b-3c, the vector of any of paragraphs 4-4c, or the host cell of paragraph 5 for use in treating (e.g., prophylactically and/or therapeutically treating) a disorder associated with or caused by DPR-containing protein or aggregated forms thereof (e.g., ALS, FTLD, or FTLD-ALS).

12. A method for in vivo detection of a DPR (e.g., poly-GA DPR) deposit in the brain, the method comprising:
  administering to a subject (e.g., human subject) the anti-DPR antibody or fragment thereof of any of paragraphs 1-1e, wherein the antibody or fragment thereof is attached to a detectable label (e.g., enzyme, radioisotope, fluorophore, and/or heavy metal); and
  detecting the detectable label in the brain of the subject, thereby detecting the DPR deposit in the brain of the subject, optionally wherein the DPR deposit is detected by positron emission tomography (PET), single photon emission tomography (SPECT), near infrared (NIR), optical imaging, or magnetic resonance imaging (MRI).

Sequences

TABLE 14

Selection of sequences

| SEQ ID NO | Description | Sequence |
|---|---|---|
| 3 | NI-308.5J10 VH-CDR1 | DYYWS |
| 4 | NI-308.5J10 VH-CDR2 | RTYTNGKTTYTYNPSLES |
| 5 | NI-308.5J10 VH-CDR3 | WGAVTGDYYYGMDV |
| 8 | NI-308.5J10 VL-CDR1 | RSPRSLLHTNGYTYLD |

TABLE 14-continued

Selection of sequences

| SEQ ID NO | Description | Sequence |
|---|---|---|
| 9 | NI-308.5J10 VL-CDR2 | LASNRAS |
| 10 | NI-308.5J10 VL-CDR3 | MQGLQPSWT |
| 13 | NI-308.5J10 VH-CDR2 sequence-N54S mutation | RTYTSGKTTYTYNPSLES |
| 14 (nucleic acid) | NI-308.5J10 variable heavy chain (VH) sequence-N54T mutation | caggtgcagctgcaggag tcggggcccaggactggtg aggccttcggagccctgt ccctcacttacactgtct taggtggctccgtcagtg attactactggagctgca tccggcagccgccgggaa gggactggagtggattgg gcgaacatatactaccgg gaagaccacttacactta caacccctccctcgagag tcgactcagtttgtctat agacacgtccatgaacca attctccctgaagttgac ctctgtgacggccgcgga cacggccgtctattactg cgcgagatgggggcggt gactggtgactactacta cggtatggacgtctgggg cccaggcaccctggtcac cgtctcctcg |
| 14 (amino acid) | NI-308.5J10 variable heavy chain (VH) sequence-N54T mutation | QVQLQESGPGLVKPS ETLSLTYTVLGGSVS DYYWSCIRQPAGKGL EWIGRTYTTGKTTYT YNPSLESRLSLSIDT SMNQFSLKLTSVTAA DTAVYYCARWGAVTG DYYYGMDVWGPGTLV TVSS |
| 16 | NI-308.5J10 VH-CDR2 sequence-N54T mutation | RTYTTGKTTYTYNPS LES |
| 19 | NI-308.5J10 VH-CDR2 sequence-G55S mutation | RTYTNSKTTYTYNPS LES |
| 22 | NI-308.5J10 VH-CDR2 sequence-G55T mutation | RTYTNTKTTYTYNPS LES |
| 25 | NI-308.5J10 variable light chain (VK) plasmid (SDD 152) | EIVLTQSPLSLSVTP GEPASISCRSPRSLL HTNGYTYLDWYLQRP GQSPQLLIFLASNRA SGVPDRFSGSGSGTN FTLRISGVEADDVGV YYCMQGLQPSWTFGQ GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC |
| 26 | NI-308.5J10-hIgG1 variable heavy chain (VH) plasmid (SDD 151) | QVQLQESGPGLVKPS ETLSLTYTVLGGSVS DYYWSCIRQPAGKGL EWIGRTYTNGKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCDKTHTCPPCPAPE LLGGPSVFLFPPKPK DTLMISRTPEVTCVV VDVSHEDPEVKFNWY VDGVEVHNAKTKPRE EQYNSTYRVVSVLTV LHQDWLNGKEYKCKV SNKALPAPIEKTISK AKGQPREPQVYTLPP SRDELTKNQVSLTCL VKGFYPSDIAVEWES NGQPENNYKTTPPVL DSDGSFFLYSKLTVD KSRWQQGNVFSCSVM HEALHNHYTQKSLSL SPG |
| 27 | NI-308.5J10 variable light chain (VK) plasmid (SDD 177)-N75D mutation | EIVLTQSPLSLSVTP GEPASISCRSPRSLL HTNGYTYLDWYLQRP GQSPQLLIFLASNRA SGVPDRFSGSGSGTD FTLRISGVEADDVGV YYCMQGLQPSWTFGQ GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC |
| 28 | NI-308.5J10-hIgG1 variable heavy chain (VH) plasmid (SDD 173)-N54S mutation | QVQLQESGPGLVKPS ETLSLTYTVLGGSVS DYYWSCIRQPAGKGL EWIGRTYTSGKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCDKTHTCPPCPAPE LLGGPSVFLFPPKPK DTLMISRTPEVTCVV VDVSHEDPEVKFNWY VDGVEVHNAKTKPRE EQYNSTYRVVSVLTV |

TABLE 14-continued

Selection of sequences

| SEQ ID NO | Description | Sequence |
|---|---|---|
| | | LHQDWLNGKEYKCKV SNKALPAPIEKTISK AKGQPREPQVYTLPP SRDELTKNQVSLTCL VKGFYPSDIAVEWES NGQPENNYKTTPPVL DSDGSFFLYSKLTVD KSRWQQGNVFSCSVM HEALHNHYTQKSLSL SPG |
| 29 | NI-308.5J10-hIgG1 variable heavy chain (VH) plasmid (SDD 174)-N54T mutation | QVQLQESGPGLVKPS ETLSLTYTVLGGSVS DYYWSCIRQPAGKGL EWIGRTYTTGKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCDKTHTCPPCPAPE LLGGPSVFLFPPKPK DTLMISRTPEVTCVV VDVSHEDPEVKFNWY VDGVEVHNAKTKPRE EQYNSTYRVVSVLTV LHQDWLNGKEYKCKV SNKALPAPIEKTISK AKGQPREPQVYTLPP SRDELTKNQVSLTCL VKGFYPSDIAVEWES NGQPENNYKTTPPVL DSDGSFFLYSKLTVD KSRWQQGNVFSCSVM HEALHNHYTQKSLSL SPG |
| 30 | NI-308.5J10-hIgG1 variable heavy chain (VH) plasmid (SDD 175)-G55S mutation | QVQLQESGPGLVKPS ETLSLTYTVLGGSVS DYYWSCIRQPAGKGL EWIGRTYTNSKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCDKTHTCPPCPAPE LLGGPSVFLFPPKPK DTLMISRTPEVTCVV VDVSHEDPEVKFNWY VDGVEVHNAKTKPRE EQYNSTYRVVSVLTV LHQDWLNGKEYKCKV SNKALPAPIEKTISK AKGQPREPQVYTLPP SRDELTKNQVSLTCL VKGFYPSDIAVEWES NGQPENNYKTTPPVL DSDGSFFLYSKLTVD KSRWQQGNVFSCSVM HEALHNHYTQKSLSL SPG |
| 31 | NI-308.5J10-hIgG1 variable heavy chain (VH) plasmid (SDD 176)-G55T mutation | QVQLQESGPGLVKPS ETLSLTYTVLGGSVS DYYWSCIRQPAGKGL EWIGRTYTNTKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCDKTHTCPPCPAPE LLGGPSVFLFPPKPK DTLMISRTPEVTCVV VDVSHEDPEVKFNWY VDGVEVHNAKTKPRE EQYNSTYRVVSVLTV LHQDWLNGKEYKCKV SNKALPAPIEKTISK AKGQPREPQVYTLPP SRDELTKNQVSLTCL VKGFYPSDIAVEWES NGQPENNYKTTPPVL DSDGSFFLYSKLTVD KSRWQQGNVFSCSVM HEALHNHYTQKSLSL SPG |
| 32 | NI-308.5J10-Fab-6His variable heavy chain (VH) plasmid (SDD 178) | QVQLQESGPGLVKPS ETLSLTYTVLGGSVS DYYWSCIRQPAGKGL EWIGRTYTNGKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCHHHHHH |
| 33 | NI-308.5J10-Fab-6His variable heavy chain (VH) plasmid (SDD 179)-N54S mutation | QVQLQESGPGLVKPS ETLSLTYTVLGGSVS DYYWSCIRQPAGKGL EWIGRTYTSGKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCHHHHHH |
| 34 | NI-308.5J10-Fab-6His variable heavy chain (VH) plasmid (SDD 180)-N54T mutation | QVQLQESGPGLVKPS ETLSLTYTVLGGSVS DYYWSCIRQPAGKGL EWIGRTYTTGKTTYT YNPSLESRLSLSIDT SMNQFSLKLTSVTAA DTAVYYCARWGAVTG |

TABLE 14-continued

Selection of sequences

| SEQ ID NO | Description | Sequence |
|---|---|---|
| | mutation | DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCHHHHHH |
| 35 | NI-308.5J10-Fab-6His variable heavy chain (VH) plasmid (SDD 181)-G55S mutation | QVQLQESGPGLVKPS ETLSLTYTVLGGSVS DYYWSCIRQPAGKGL EWIGRTYTNSKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCHHHHHH |
| 36 | NI-308.5J10-Fab-6His variable heavy chain (VH) plasmid (SDD 182)-G55T mutation | QVQLQESGPGLVKPS ETLSLTYTVLGGSVS DYYWSCIRQPAGKGL EWIGRTYTNTKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCHHHHHH |
| 61 | synthesized dipeptide repeat protein (GA)15 | CHHHHHGAGAGAGA GAGAGAGAGAGAGAG AGAGAGA |
| 62 | synthesized dipeptide repeat protein (GP)15 | CGPGPGPGPGPGPGP GPGPGPGPGPGPGPG P |
| 63 | synthesized dipeptide repeat protein (GR)15 | CGRGRGRGRGRGRGR GRGRGRGRGRGRGRG R |
| 64 | synthesized dipeptide repeat protein (PA)15 | CPAPAPAPAPAPAPA PAPAPAPAPAPAPAP A |
| 65 | synthesized dipeptide repeat protein (PR)15 | CPRPRPRPRPRPRPR PRPRPRPRPRPRPRP R |
| 66 | dipeptide repeat protein peptide GA | GAGAGAGAGAGAGAG AGAGAGAGAGAGAGA |
| 67 | dipeptide repeat protein peptide GP | GPGPGPGPGPGPGPG PGPGPGPGPGPGPGP |
| 68 | dipeptide repeat protein peptide GR | GRGRGRGRGRGRGRG RGRGRGRGRGRGRGR |
| 69 | dipeptide repeat protein peptide PA | PAPAPAPAPAPAPAP APAPAPAPAPAPAPA |
| 70 | dipeptide repeat protein peptide PR | PRPRPRPRPRPRPRP RPRPRPRPRPRPRPR |
| 71 | synthesized dipeptide repeat protein (GA)20 | GAGAGAGAGAGAGAG AGAGAGAGAGAGAGA GAGAGAGAGAHHHHH H |
| 72 | synthesized dipeptide repeat protein (GA)10 | GAGAGAGAGAGAGAG AGAGAHHHHHH |
| 73 | synthesized dipeptide repeat protein (GA)6 | GAGAGAGAGAGAHHH HHH |
| 74 | synthesized dipeptide repeat protein (GA)5 | GAGAGAGAGAHHHHH H |
| 75 | synthesized dipeptide repeat protein (GA)4 | GAGAGAGAHHHHHH |
| 76 | synthesized dipeptide repeat protein (GA)3 | GAGAGAHHHHHH |
| 77 | synthesized dipeptide repeat protein (GA)2 | GAGAHHHHHH |

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application including the background section and manufacturer's specifications, instructions, etc.) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

Example 1: Isolation and Identification of Anti-(Poly-GA) Dipeptide Repeat (DPR) Protein Antibodies Human-derived antibodies targeting poly-GA dipeptide repeat (DPR) proteins, fragments thereof, C9orf72-DPRs and/or fragments thereof were identified based on the method described in the international application WO 2016/050822 A2, the disclosure content of which is incorporated herein by reference. In particular, poly-GA dipeptide repeat proteins ($GA_{15}$: H-CHHHHHH$(GA)_{15}$-OH) (SEQ ID NO: 61) were synthesized and purified by Schafer-N (Copenhagen, Denmark). poly-GA dipeptide repeat proteins were then conjugated via a bifunctional linker (SMCC) to bovine serum albumin (BSA). Subsequently, direct ELISA was performed using 96-well microplates (Corning) coated with either non-conjugated or BSA-conjugated poly-GA dipeptide repeat proteins or with BSA (Sigma-Aldrich, Buchs, Switzerland) at a concentration of 5 µg/ml in coating buffer (15 mM $Na_2CO_3$, 35 mM $NaHCO_3$, pH 9.42). Non-specific binding sites were blocked for 1 h at room temperature with PBS/0.1% Tween®-20 containing 2% BSA (Sigma-Aldrich, Buchs, Switzerland). B cell conditioned medium was transferred from memory B cell culture plates to ELISA plates and incubated for one hour at RT, followed by incubation with a donkey anti-human IgG Fcγ-specific antibody conjugated with HRP (Jackson ImmunoResearch Laboratories, Inc., West Grove, USA) and a goat anti-human IgA specific antibody conjugated with HRP (Jackson ImmunoResearch Laboratories, Inc., West Grove, USA). Binding was determined by measurement of HRP activity in a standard colorimetric assay. Only B cell cultures which have shown binding of the antibodies contained in the medium to poly-GA DPRs but not to BSA were subjected to antibody cloning.

Example 2: Determination of Antibody Sequence

The amino acid sequences of the variable regions of the above identified anti-(poly-GA) DPR antibodies were determined on the basis of their mRNA sequences, see FIG. 1A-F. In brief, living B cells of selected non-immortalized memory B cell cultures were harvested. Subsequently, the mRNAs from cells producing selected anti-(poly-GA) DPR antibodies were extracted and converted in cDNA, and the sequences encoding the antibody's variable regions were amplified by PCR, cloned into plasmid vectors and sequenced. In brief, a combination of primers representing all sequence families of the human immunoglobulin germline repertoire was used for the amplifications of leader peptides, V-segments and J-segments. The first round of amplification was performed using leader peptide-specific primers in 5'-end and constant region-specific primers in 3'-end (Smith et al., Nat Protoc. 4 (2009), 372-384). For heavy chains and kappa light chains, the second round of amplification was performed using V-segment-specific primers at the 5'-end and J-segment-specific primers at the 3'-end. For lambda light chains, the second round amplification was performed using V-segment-specific primers at the 5'-end and a C-region-specific primer at the 3'-end (Marks et al., Mol. Biol. 222 (1991), 581-597; de Haard et al., J. Biol. Chem. 26 (1999), 18218-18230).

Identification of the antibody clone with the desired specificity was performed by re-screening on ELISA upon recombinant expression of complete antibodies. Recombinant expression of complete human IgG1 antibodies was achieved upon insertion of the variable heavy and light chain sequences "in the correct reading frame" into expression vectors that complement the variable region sequence with a sequence encoding a leader peptide at the 5'-end and at the 3'-end with a sequence encoding the appropriate constant domain(s). To that end the primers contained restriction sites designed to facilitate cloning of the variable heavy and light chain sequences into antibody expression vectors. Heavy chain immunoglobulins were expressed by inserting the immunoglobulin heavy chain RT-PCR product in frame into a heavy chain expression vector bearing a signal peptide and the constant domains of human or mouse immunoglobulin gamma 1. Kappa light chain immunoglobulins were expressed by inserting the kappa light chain RT-PCR-product in frame into a light chain expression vector providing a signal peptide and the constant domain of human kappa light chain immunoglobulin. Lambda light chain immunoglobulins were expressed by inserting the lambda light chain RT-PCR-product in frame into a lambda light chain expression vector providing a signal peptide and the constant domain of human or mouse lambda light chain immunoglobulin.

Functional recombinant monoclonal antibodies were obtained upon co-transfection into HEK 293 or CHO cells (or any other appropriate recipient cell line of human or mouse origin) of an Ig-heavy-chain expression vector and a kappa or lambda Ig-light-chain expression vector. Recombinant human monoclonal antibody was subsequently purified from the conditioned medium using a standard Protein A column purification. Recombinant human monoclonal antibody can be produced in unlimited quantities using either transiently or stably transfected cells. Cell lines producing recombinant human monoclonal antibody can be established either by using the Ig-expression vectors directly or by re-cloning of Ig-variable regions into different expression vectors. Derivatives such as F(ab), F(ab)2 and scFv can also be generated from these Ig-variable regions.

The framework and complementarity determining regions were determined by comparison with reference antibody sequences available in databases such as Abysis (www.bioinf.org.uk/abysis/), and annotated using the Kabat numbering scheme (www.bioinf.org.uk/abs/).

Example 3: ELISA $EC_{50}$ Analysis to C9orf72 Dipeptide Repeat Proteins

To determine the binding specificity and the half maximal effective concentration ($EC_{50}$) of the recombinant human-derived C9orf72 antibody NI-308.5J10 for C9orf72 poly-GA DPRs an ELISA $EC_{50}$ analysis was performed. In brief, dipeptide repeat proteins were synthesized and purified by Schafer-N(Copenhagen, Denmark): $(GA)_{15}$: H-CHHHHHH$(GA)_{15}$-OH (SEQ ID NO: 61); $(GP)_{15}$: H-C$(GP)_{15}$-OH (SEQ ID NO: 62); $(GR)_{15}$: H-C$(GR)_{15}$-OH (SEQ ID NO: 63); $(PA)_{15}$: H-C$(PA)_{15}$-OH (SEQ ID NO: 64); $(PR)_{15}$: H—C$(PR)_{15}$-OH (SEQ ID NO: 65). 96-well microplates (Corning Incorporated, Corning, USA) were coated with dipeptide repeat protein peptides at a concentration of either 5 µg/ml or 20 µg/ml in coating buffer (15 mM $Na_2CO_3$, 35 mM $NaHCO_3$, pH 9.42). Non-specific binding sites were blocked for 1 h at RT with PBS/0.1% Tween®-20 containing 2% BSA (Sigma-Aldrich, Buchs, Switzerland). NI-308.5J10 was diluted to the indicated concentrations and incubated for 1 h at RT, followed by incubation with a donkey anti-human IgG Fcγ-specific antibody conjugated with HRP (Jackson ImmunoResearch Laboratories, Inc., West Grove, USA).

Binding was determined by measurement of HRP activity in a standard colorimetric assay.

$EC_{50}$ values were estimated by non-linear regression using GraphPad Prism software (San Diego, USA). The binding specificity and $EC_{50}$ of the human-derived antibody NI-308.5J10 for C9orf72 dipeptide repeat protein peptides $(GA)_{15}$ (SEQ ID NO: 66), $(GP)_{15}$ (SEQ ID NO: 67), $(GR)_{15}$ (SEQ ID NO: 68), $(PA)_{15}$ (SEQ ID NO: 69) and $(PR)_{15}$ (SEQ ID NO: 70) were determined by indirect ELISA. Antibody NI-308.5J10 specifically recognized the poly-GA DPR protein with binding affinities in the subnanomolar range (Table 3, FIG. 2). In conclusion, high-throughput immune repertoire analyses of healthy elderly human donor populations by RTM™ screening lead to the successful cloning and recombinant production of a human monoclonal antibody specifically targeting the C9orf72 hexanucleotide expansion-associated poly-GA DPR with high affinity.

TABLE 3

$EC_{50}$ analysis of the human-derived antibody NI-308.5J10 to five C9orf72 DPR proteins.

| | $EC_{50}$ [nM] | | | | |
|---|---|---|---|---|---|
| Antibody | $(GA)_{15}$ (SEQ ID NO: 66) | $(GP)_{15}$ (SEQ ID NO: 67) | $(GR)_{15}$ (SEQ ID NO: 68) | $(PR)_{15}$ (SEQ ID NO: 70) | $(PA)_{15}$ (SEQ ID NO: 69) |
| NI-308.5J10 | 0.26 | — | — | — | — |

Example 4: Binding Affinity to BSA-Coupled DPR Peptides

To determine the half maximal effective concentration ($EC_{50}$) of the recombinant human-derived NI-308.5J10 antibody for poly-GA C9orf72 dipeptide repeat protein peptides coupled to bovine serum albumin (BSA) an ELISA $EC_{50}$ analysis was performed. In brief, poly-GA dipeptide repeat proteins were synthesized and purified by Schafer-N(Copenhagen, Denmark): $(GA)_{15}$: H-CHHHHHH$(GA)_{15}$-OH (SEQ ID NO: 61). Poly-GA DPR protein peptides were then conjugated via a bifunctional linker (SMCC) to bovine serum albumin (BSA). 96-well microplates (Corning Incorporated, Corning, USA) were coated with poly-GA BSA-coupled or uncoupled dipeptide repeat protein peptides at a concentration of 5 μg/ml in coating buffer (15 mM $Na_2CO_3$, 35 mM $NaHCO_3$, pH 9.42). Non-specific binding sites were blocked for 1 h at RT with PBS/0.1% Tween®-20 containing 2% BSA (Sigma-Aldrich, Buchs, Switzerland). NI-308.5J10 was diluted to the indicated concentrations and incubated 1 h at RT, followed by incubation with a donkey anti-human IgG Fcγ-specific antibody conjugated with HRP (Jackson ImmunoResearch Laboratories, Inc., West Grove, USA). Binding was determined by measurement of HRP activity in a standard colorimetric assay.

$EC_{50}$ values were estimated by non-linear regression using GraphPad Prism software (San Diego, USA). Comparable binding affinities were determined for BSA-coupled and uncoupled poly-GA DPRs for antibody NI-308.5J10 (Table, 4, FIG. 3). In conclusion, antibody NI-308.5J10 recognizes poly-GA DPR peptides coupled to BSA carrier protein with comparable affinities to hydrophobically coated peptides under these experimental conditions.

TABLE 4

Binding affinities to BSA-coupled and uncoupled C9orf72 DPR peptides.

| | | $EC_{50}$ [nM] | |
|---|---|---|---|
| Antibody | Peptide | BSA-coupled peptide | Uncoupled peptide |
| NI-308.5J10 | $(GA)_{15}$ (SEQ ID NO: 66) | 0.16 | 0.23 |

Example 5: Binding Specificity Analysis to Unrelated Amyloidogenic Proteins

Figure 4:
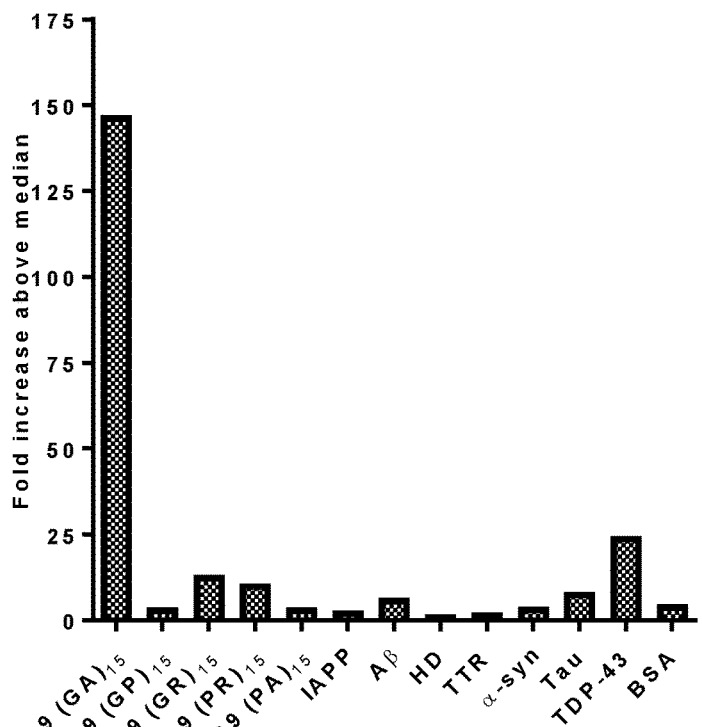
FIG. 4: Binding specificity analysis of human-derived anti-(poly-GA) DPR antibody NI-308.5J10 to unrelated aggregating proteins. Antibody binding to C9orf72 $(GA)_{15}$ (SEQ ID NO: 66), $(GP)_{15}$ (SEQ ID NO: 67), $(GR)_{15}$ (SEQ ID NO: 68), $(PR)_{15}$ (SEQ ID NO: 70) and $(PA)_{15}$ (SEQ ID NO: 69) peptides and 5 unrelated amyloidogenic proteins was determined by indirect ELISA. Antibody NI-308.5J10—showed binding to C9orf72 $(GA)_{15}$ (SEQ ID NO: 66) peptides with absence of significant off-target binding to the unrelated analytes. The NI-308.5J10 antibody was tested at 20 nM concentration.

To determine the target specificity of the NI-308.5J10 recombinant antibody indirect ELISA was performed as follows. 96-well microplates (Corning Incorporated, Corning, USA) were coated with $(GA)_{15}$ (SEQ ID NO: 66), $(GP)_{15}$ (SEQ ID NO: 67), $(GR)_{15}$ (SEQ ID NO: 68), $(PA)_{15}$ (SEQ ID NO: 69) or $(PR)_{15}$ (SEQ ID NO: 70) peptides at 5 μg/ml per peptide or unrelated target proteins at a concentration of 5-10 μg/ml in coating buffer (15 mM $Na_2CO_3$, 35 mM $NaHCO_3$, pH 9.42). Non-specific binding sites were blocked for 1 h at RT with PBS/0.1% Tween®-20 containing 2% BSA (Sigma-Aldrich, Buchs, Switzerland). NI-308.5J10 antibody was diluted at 4 nM concentration and incubated 1 h at RT. Binding was determined using donkey anti-human IgG Fcg-specific antibody conjugated with HRP (Jackson ImmunoResearch Laboratories, Inc., West Grove, USA) followed by measurement of HRP activity in a standard colorimetric assay. Signals for target protein were calculated in fold increase above median. The determination of target specificity of the NI-308.5J10 human-derived antibody by indirect ELISA assessed antibody binding to C9orf72 dipeptide repeat proteins and seven unrelated amyloid-forming proteins (IAPP, Ab, HD, TTR, a-syn, Tau, TDP-43). As shown in FIG. 4 the human-derived antibody NI-308.5J10 revealed high binding specificity to poly-GA DPR peptides with absent or minimal cross-reactivity to unrelated amyloidogenic proteins.

Example 6: Western Blot Analysis of C9orf72 Dipeptide Repeat Proteins

To determine the binding specificity of the recombinant human-derived C9orf72 antibody NI-308.5J10 for C9orf72 poly-GA dipeptide repeat proteins immunoblot analysis was performed. Dipeptide repeat protein peptides were synthesized and purified by Schafer-N (Copenhagen, Denmark): $(GA)_{15}$: H-CHHHHHH$(GA)_{15}$-OH (SEQ ID NO: 61); $(GP)_{15}$: H-C$(GP)_{15}$-OH (SEQ ID NO: 62); $(GR)_{15}$: H-C$(GR)_{15}$-OH (SEQ ID NO: 63); $(PA)_{15}$: H-C$(PA)_{15}$-OH (SEQ ID NO: 64); $(PR)_{15}$: H-C$(PR)_{15}$-OH (SEQ ID NO: 65). DPR protein peptides were then conjugated via a bifunctional linker (SMCC) to bovine serum albumin (BSA). In brief, BSA-conjugated dipeptide repeat protein peptides (0.5 μg) were resolved by gradient SDS-PAGE (Novex® Bis-Tris NuPAGE® 4-12%; Life Technologies Europe B.V., Zug, Switzerland) using Novex® NuPAGE® MES SDS Running Buffer complemented with antioxidant (Life Technologies Europe B.V., Zug, Switzerland). Resolved proteins were then electroblotted (Novex® Semi-Dry Blotter, 1 h, 25V) on methanol-activated PVDF membrane (Immobilon®-P Transfer Membrane, Merck & Cie, Schaffhausen, Switzerland) by the use of Novex® NuPAGE® transfer buffer 2× (Life Technologies Europe B.V., Zug, Switzerland). Nonspecific binding sites were blocked overnight at 4° C. (or alternatively for 1 h at RT) with PBS/0.1% Tween®-20 containing 2% BSA (Sigma-Aldrich, Buchs, Switzerland) (PBST). NI-308.5J10 antibody was diluted at 10 nM concentration and incubated for 1 h at RT (or alternatively overnight at 4° C.). Membrane was washed three times in PBST for 15 min at RT and then incubated with a donkey anti-human IgG Fcγ-specific antibody conjugated with HRP (1:20000 or 1:10000 dilution, Jackson ImmunoResearch Laboratories, Inc., West Grove, USA) for 1 h at RT. Antibody binding was determined by membrane development using ECL and ImageQuant 350 detection (GE Healthcare, Otelfingen, Switzerland).

Figure 5:
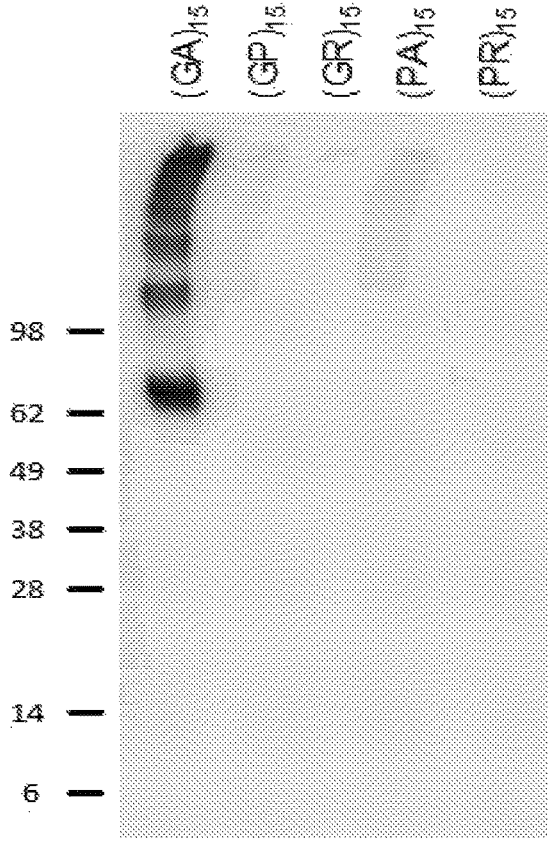
FIG. 5: Binding selectivity of NI-308.5J10 antibody for C9orf72 dipeptide repeat proteins. Determination of human-derived antibody NI-308.5J10 C9orf72 binding selectivity for BSA-coupled C9orf72 dipeptide repeat protein peptides $(GA)_{15}$ (SEQ ID NO: 66), $(GP)_{15}$ (SEQ ID NO: 67), $(GR)_{15}$ (SEQ ID NO: 68), $(PA)_{15}$ (SEQ ID NO: 69) and $(PR)_{15}$ (SEQ ID NO: 70) by Western blot analysis. The C9orf72 poly-GA DPR protein was recognized by antibody NI-308.5J10.

The binding specificity of the human-derived antibody NI-308.5J10 to BSA-coupled C9orf72 dipeptide repeat proteins $(GA)_{15}$ (SEQ ID NO: 66), $(GP)_{15}$ (SEQ ID NO: 67), $(GR)_{15}$ (SEQ ID NO: 68), $(PA)_{15}$ (SEQ ID NO: 69) and $(PR)_{15}$ (SEQ ID NO: 70) was determined by Western blot analysis. Antibody NI-308.5J10 specifically recognized the DPR protein poly-GA (FIG. 5). In conclusion, the human-derived antibody NI-308.5J10 can recognize BSA-coupled poly-GA DPR peptides following SDS PAGE and Western blotting. The observed biding patterns are consistent with the results obtained by ELISA analyses.

Example 7: Characterization of Repeat-Length Dependent Binding by Indirect ELISA To determine the binding affinity of the recombinant human-derived antibody 308.5J10 to C9orf72 DRPs of different repeat sizes an ELISA $EC_{50}$ analysis was performed. In brief, Dipeptide repeat protein peptides were synthesized and purified by Schafer-N(Copenhagen, Denmark): $GA_{20}$: H-$(GA)_{20}$HHHHHH-$NH_2$ (SEQ ID NO: 71); $GA_{10}$: H-$(GA)_{10}$HHHHHH-$NH_2$ (SEQ ID NO: 72); $GA_{6}$: H-$(GA)_{6}$HHHHHH-$NH_2$ (SEQ ID NO: 73); $GA_{5}$: H-$(GA)_{5}$HHHHHH-$NH_2$ (SEQ ID NO: 74); $GA_{4}$: H-$(GA)_{4}$HHHHHH-$NH_2$ (SEQ ID NO: 75); $GA_{3}$: H-$(GA)_{3}$HHHHHH-$NH_2$ (SEQ ID NO: 76); $GA_{2}$: H-$(GA)_{2}$HHHHHH-$NH_2$ (SEQ ID NO: 77). 96-well microplates (Corning Incorporated, Corning, USA) were coated with dipeptide repeat protein peptides at a concentration of 50 µg/ml in coating buffer (15 mM $Na_2CO_3$, 35 mM $NaHCO_3$, pH 9.42). Non-specific binding sites were blocked for 1 h at RT with PBS/0.1% Tween®-20 containing 2% BSA (Sigma-Aldrich, Buchs, Switzerland). NI-308.5J10 was diluted to the indicated concentrations and incubated 1 h at RT, followed by incubation with a donkey anti-human IgG Fcγ-specific antibody conjugated with HRP (Jackson ImmunoResearch Laboratories, Inc., West Grove, USA). Binding was determined by measurement of HRP activity in a standard colorimetric assay. $EC_{50}$ values were estimated by non-linear regression using GraphPad Prism software (San Diego, USA).

The binding affinity of antibody NI-308.5J10 for C9orf72 poly-GA DPR proteins with different repeat lengths was determined following hydrophobic peptide coating by indirect ELISA. Antibody NI-308.5J10 required at least 6 GA repeats for a first detectable binding. High affinity binding was detected for poly-GA DPRs harboring 10 (SEQ ID NO: 79) or 20 (GA)-repeats (SEQ ID NO: 82), reflected in an $EC_{50}$ in the subnanomolar range (Table 5, FIG. 6). In conclusion, human-derived NI-308.5J10 antibody display a repeat-length dependent binding to poly-GA DPRs with absent binding to short repeat sizes and preferential high affinity binding to extended dipeptide repeats.

TABLE 5

C9orf72 poly-GA repeat-length dependent binding of antibody NI-308.5J10.

| Antibody | $EC_{50}$ [nM] | | | | | | |
|---|---|---|---|---|---|---|---|
| | $(GA)_2$ (SEQ ID NO: 71) | $(GA)_3$ (SEQ ID NO: 72) | $(GA)_4$ (SEQ ID NO: 73) | $(GA)_5$ (SEQ ID NO: 74) | $(GA)_6$ (SEQ ID NO: 75) | $(GA)_{10}$ (SEQ ID NO: 76) | $(GA)_{20}$ (SEQ ID NO: 77) |
| NI-308.5J10 | — | — | — | — | 13.8 | 0.30 | 0.29 |

Example 8: Characterization of Binding Properties by Bio-Layer Interferometry To determine the binding constants ($K_D$, $K_a$, $K_d$) of the NI-308.5J10 antibody to $(GA)_{15}$ (SEQ ID NO: 66) dipeptide repeat (DPR) peptides bio-layer interferometry (BLI) has been performed. Poly-GA dipeptide repeat protein peptides were synthesized and purified by Schafer-N (Copenhagen, Denmark): $(GA)_{15}$: H-CHHHHHH$(GA)_{15}$-OH (SEQ ID NO: 61). Pure, lyophilized $(GA)_{15}$ (SEQ ID NO: 66) was dissolved in DMSO (Sigma-Aldrich, Buchs, Switzerland) at a concentration of 10 mg/ml and stored at −20° C. In brief, bio-layer interferometry experiments were performed on Octet RED96 instrument (Pall ForteBio LLC, Fremont, USA). Octet amine-reactive (AR2G) biosensors were used for covalent immobilization of $(GA)_{15}$ (SEQ ID NO: 66) dipeptide repeat protein peptides. AR2G biosensors were activated with EDC (1-Ethyl-3-[3-dimethylaminopropyl] carbodiimide hydrochloride; 20 mM in water; Pall ForteBio LLC, Fremont, USA) and s-NHS (N-hydroxysulfosuccinimide; 10 mM in water; Pall ForteBio LLC, Fremont, USA) for 300 s, followed by loading of the biosensor surface with 5 µg/ml of $(GA)_{15}$ (SEQ ID NO: 66) peptides in 10 mM acetate buffer pH 6 (Pall ForteBio LLC, Fremont, USA) for 600 s. Upon peptide loading, AR2G biosensors were quenched with 1 M ethanolamine pH 8.5 (Pall ForteBio LLC, Fremont, USA) for 300 s, rinsed in kinetics buffer (Pall ForteBio LLC, Fremont, USA) for 120 s (baseline) and human NI-308.5J10 antibody association was assessed at different concentrations (30, 15, 7.5, 3.75 and 1.875 nM) in diluted kinetics buffer (1:10 in PBS) for 600 s. Antibody dissociation was evaluated in kinetics buffer for 800 s. All binding data were referenced by collecting data with a PBS only reference. Data analysis was performed by using the Octet system software (Pall ForteBio LLC, Fremont, USA) with simultaneous $K_a/K_d$ global fitting with 1:1 interaction model. BLI sensorgrams were drawn with the Prism software from GraphPad (San Diego, USA) upon fitting.

Figure 7:
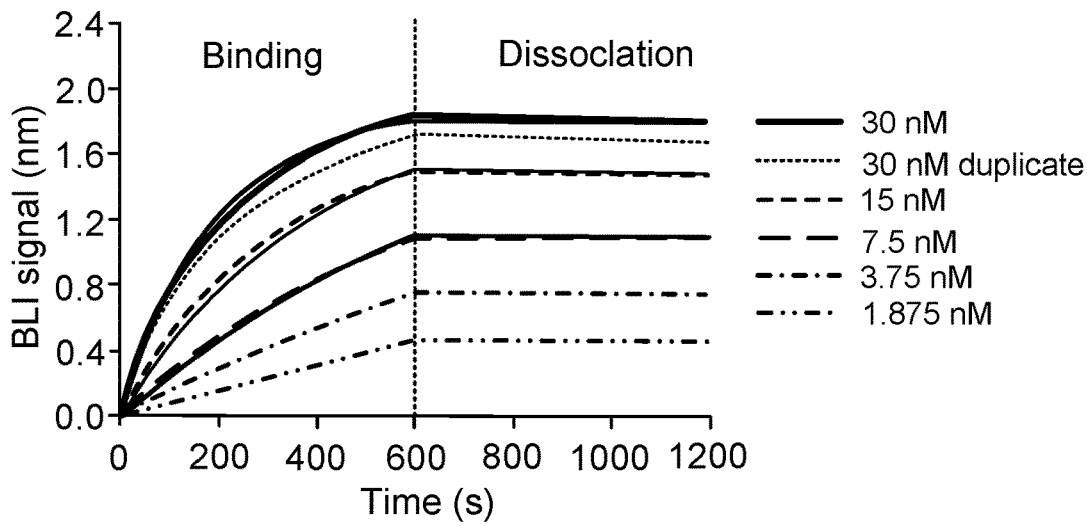
FIG. 7: Characterization of NI-308.5J10 binding to poly-GA C9orf72 dipeptide repeat protein peptides by bio-layer interferometry. Determination of the binding constants KD, $K_a$ and $K_d$ of antibody NI-308.5J10 for the C9orf72 dipeptide repeat protein peptides $(GA)_{15}$ (SEQ ID NO: 66) using bio-layer interferometry. Bio-layer interferometry (BLI) sensorgrams showing the binding of NI-308.5J10 toward immobilized synthetic $(GA)_{15}$ peptides (SEQ ID NO: 66). The antibody was run with various concentrations: 30, 15, 7.5, 3.75 and 1.875 nM. Measurements were performed in triplicates. Sensorgrams show single measurements for each tested antibody concentration but for the highest concentration for which a second dataset is additionally shown. Antibody NI-308.5J10 showed as KD of $(1.5\pm0.2)\times10^{-10}$ M, a $K_a$ of $(1.63\pm0.05)\times10^5$ $M^{-1}s^{-1}$ and a $K_d$ of $(2.4\pm0.4)\times10^{-5}$ $s^{-1}$.

Antibody NI-308.5J10 binds with high affinity KD (0.15±0.02 nM) to poly-GA DPR peptides with a high association rate constant ($K_a$=(1.63±0.05)×$10^5$ $M^{-1}s^{-1}$) and dissociation constant in about the same range ($K_d$=2.4±0.4)× $10^{-5}$ $s^{-1}$) (FIG. 7 and Table 6). In conclusion, antibody NI-308.5J10 recognizes with high affinity poly-GA DPR peptides.

TABLE 6

Binding constants ($K_D$, $K_a$, $K_d$) of antibody NI-308.5J10 for poly-GA DPR peptides

| Antibody | KD (M) | $K_a$ ($Ms^{-1}$) | $K_d$ ($s^{-1}$) |
| --- | --- | --- | --- |
| NI-308.5J10 | (1.5 ± 0.2) × $10^{-10}$ | (1.63 ± 0.05) × $10^5$ | (2.4 ± 0.4) × $10^{-5}$ |

Example 9: Competitive Binding Determination by Bio-Layer Interferometry

To determine epitope competition groups for antibodies NI-308.5J10 and NI-mAb reference bio-layer interferometry (BLI) has been performed. Poly-GA dipeptide repeat protein peptides were synthesized and purified by Schafer-N(Copenhagen, Denmark): $(GA)_{15}$: H-CHHHHHH$(GA)_{15}$-OH (SEQ ID NO: 61). Pure, lyophilized $(GA)_{15}$ (SEQ ID NO: 66) was dissolved in DMSO (Sigma-Aldrich, Buchs, Switzerland) at a concentration of 10 mg/ml and stored at −20° C. In brief, bio-layer interferometry experiments were performed on Octet RED96 instrument (Pall ForteBio LLC, Fremont, USA). Octet amine-reactive (AR2G) biosensors were used for covalent immobilization of $(GA)_{15}$ (SEQ ID NO: 66) dipeptide repeat protein peptides. AR2G biosensors were activated with EDC (1-Ethyl-3-[3-dimethylaminopropyl] carbodiimide hydrochloride; 20 mM in water; Pall ForteBio LLC, Fremont, USA) and s-NHS (N-hydroxysulfosuccinimide; 10 mM in water; Pall ForteBio LLC, Fremont, USA) for 300 s, followed by loading of the biosensor surface with 5 µg/ml of $(GA)_{15}$ (SEQ ID NO: 66) peptides in 10 mM acetate buffer pH 6 (Pall ForteBio LLC, Fremont, USA) for 600 s. Upon peptide loading, AR2G biosensors were quenched with 1 M ethanolamine pH 8.5 (Pall ForteBio LLC, Fremont, USA) for 300 s, rinsed in kinetics buffer (Pall ForteBio LLC, Fremont, USA) for 120 s (baseline). NI-308 antibodies were then assessed for target binding in a pairwise fashion: Binding (for 800 s) of reference NI-308 antibody (15 nM, in kinetics buffer (Pall ForteBio LLC, Fremont, USA)) to $(GA)_{15}$ (SEQ ID NO: 66) peptides was directly followed by binding (for 800 s) of the competing NI-308 antibody (15 nM, in kinetics buffer (Pall ForteBio LLC, Fremont, USA)). All binding data was referenced by collecting data with a PBS only reference. Data analysis was performed by using the Octet system software (Pall ForteBio LLC, Fremont, USA). BLI sensorgrams were drawn with the Prism software from GraphPad (San Diego, USA).

Antibody NI-mAb reference binding to C9orf72 dipeptide repeat protein peptides $(GA)_{15}$ (SEQ ID NO: 66) is abrogated by prior binding to the target by the NI-308.5J10 antibody (FIG. 8A), indicating that the NI-mAb reference antibody is recognizing a binding epitope which is also targeted by the NI-308.5J10 antibody. Antibody NI-308.5J10 binding to C9orf72 DPR peptides $(GA)_{15}$ (SEQ ID NO: 66) is not blocked by prior binding to the target by the NI-mAb reference antibody (FIG. 8B), indicating that this antibody potentially recognizes additional conformational epitopes on the poly-GA peptides. In conclusion, antibodies NI-308.5J10 and NI-mAb reference recognize a common binding epitope and antibody NI-308.5J10 as compared to antibody NI-mAb reference potentially recognizes additional conformational epitopes on the poly-GA peptides.

Example 10: Antibody Integrity Analyses by SDS PAGE

Figure 9:
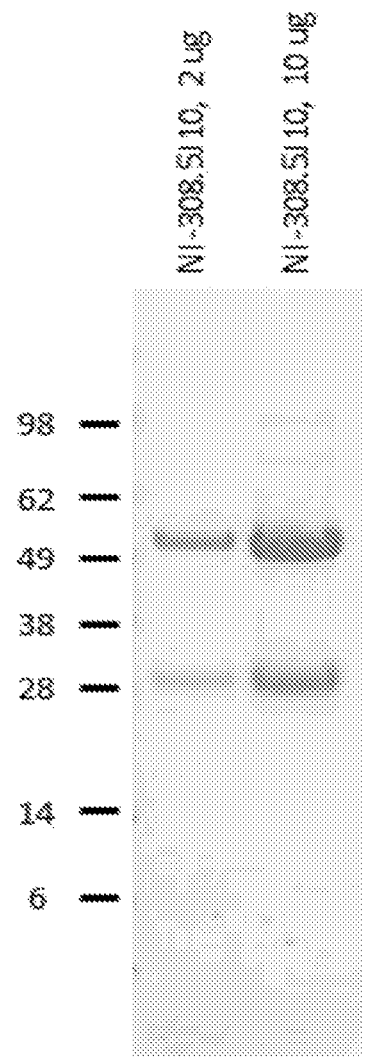
FIG. 9: Integrity analysis of antibody NI-308.5J10. SDS-PAGE analysis followed by Coomassie blue staining of 2 or 10 μg recombinant human-derived NI-308.5J10 anti-C9orf72 poly-GA DPR antibody. Two major bands corresponding to the antibody heavy and light chains at the expected size were detected.

To assess the purity and integrity of recombinant human NI-308.5J10 antibody, SDS PAGE analysis has been performed. In brief, human NI-308.5J10 antibody was expressed by transient transfections of CHO-S cells and purified by protein A affinity purification on an FPLC system (ÄKTApurifier; GE Healthcare Life Sciences). After PD-10 column (GE Healthcare Life Sciences) desalting, the antibody was formulated in PBS. 2 and 10 µg of purified recombinant human NI-308.5J10 antibody were resolved under reducing conditions by gradient SDS-PAGE (Novex® Bis-Tris NuPAGE® 4-12%; Life Technologies Europe B.V., Zug, Switzerland) using Novex® NuPAGE® MES SDS Running Buffer complemented with antioxidant (Life Technologies Europe B.V., Zug, Switzerland) followed by Coomassie blue staining (Novex® SimplyBlue™ SafeStain, Life Technologies Europe B.V., Zug, Switzerland). As a result, SDS-PAGE analysis under reducing conditions of the recombinant human NI-308.5J10 antibody revealed two major bands corresponding to the antibody heavy and light chains at the expected size. No significant contaminations or proteolytic degradation products were detectable (FIG. 9).

Example 11: Binding Analysis to DPR Aggregate Pathology in Post Mortem Human C9orf72-FTLD and Non-Neurological Control Brain Tissues To assess the binding of antibody NI-308.5J10 to C9orf72 dipeptide repeat proteins in post-mortem cerebellar tissues derived from human C9orf72-FTLD patients and non-neurological controls, binding analyses have been performed. In brief, Formalin fixed, paraffin-embedded 5 µm sections of cerebellum from 3 FTLD patients with C9orf72 hexanucleotide repeat expansions and 1 non-neurological control subjects (BiOBANC HCB-IDIBAPS, Barcelona, Spain) were pretreated for antigen retrieval by cooking in 1 mM EDTA buffer, pH 8.3, and microwave irradiation for 12 min (600 W). Quenching of endogenous peroxidase activity was achieved by treatment with 3% $H_2O_2$ in methanol for 10 min at RT. Non-specific binding sites were blocked for 1 h at RT with PBS/5% serum (horse/goat)/4% BSA. After the blocking step, sections were incubated with human-derived NI-308.5J10 antibody at 20 nM concentration overnight at 4° C. Detection was performed with biotinylated donkey anti-human IgG (H+L) (1:350 dil, Jackson ImmunoResearch Laboratories, Inc., West Grove, USA) or anti-rabbit secondary antibody (1:250 dilution, Vector Laboratories; Burlingame, USA) and antibody signal was amplified with the Vectastain Elite ABC kit (Vector Laboratories, Burlingame, USA) and detected with diaminobenzidine (DAB, Thermo Scientific, Rockford, USA). Slides were mounted using Eukitt® mounting medium (O. Kindler GmbH; Freiburg, Germany). Bright-field imaging was performed using a Dotslide VS120 slide scanner (Olympus Schweiz AG, Switzerland). Binding of NI-308.5J10 to pathological C9orf72 dipeptide repeat proteins was assessed by immunohistochemical analysis of cerebellar sections from a selected patient with FTLD and a non-neurological control subject. As shown in FIG. 10, human-derived NI-308.5J10 antibody revealed prominent neuronal cytoplasmic inclusions, neuronal intranuclear inclusions and dystrophic neurites in the granule cell layer of the cerebellum of the C9orf72-FTLD case tested. In contrast, non-neurological control cerebellum was negative for the antibody tested (FIG. 10). In conclusion, human-derived antibody NI-308.5J10 specifically detects C9orf72 dipeptide repeat protein in the granule cell layer of the cerebellum of C9orf72-FTLD cases while no staining is observed in control cerebellum demonstrating the high target specificity of the antibodies.

Example 12: Identification of Light Chain Glycosylation and Heavy Chain Asn54 Deamidation in NI-308.5J10

To identify post translational modifications, mass spectrometry has been performed. NI-308.5J10 hIgG1 was denatured by heating and treated with RapiGest (Waters, Inc) prior to degycosylation with PNGase F (Prozyme). Following treatment, protein was denatured with 40 mM DTT in 4 M urea and 10 mM EDTA at 37° C. for 1 hour. The RapiGest was quenched with 0.5% TFA at 37° C. for 1 hour and analyzed on a LCT Premier Mass Spectrometer (Waters, Inc). The separation of the light chain and heavy chain was achieved on a TSKgel Phenyl-5PW column (2.0×75 mm, 10 µm, TOSOH Bioscience). The molecular masses generated by deconvolution using the MaxEnt 1 software (Waters, Inc). The intact mass analysis of the reduced NI-308.5J10 showed that the N-glycosylation site of the light chain was almost fully occupied with hybrid/complex glycan and that the detected heavy chain corresponds to the predicted pyro-GLu23-475.

Afterwards, tryptic digest/mass spectrometry has been performed. In brief, antibody NI-308.5J10 was reduced, alkylated, precipitated and digested with trypsin. Tryptic digest was performed using 7% (w/w) trypsin (Promega) in 2 M urea, 0.15 M tris-HCl, 2 mM CaCl$_2$) pH 7.6 and 5 mM methylamine at room temperature for 8 hours. For removal of N-glycans, 1.25 mU PNGasF (Prozyme) was added to mixture after 6 hours of incubation. Prior to LC-MS analysis, urea was added to digest to final concentration of 4 M. Digest mixture was analyzed on a LC-MS system composed of a UPLC and Xevo G2-S QTof mas spectrometer (Waters, Inc). Separation of the digest was achieved with an Acquity HSS T3 C18 column (2.1×150 mM, Waters, Inc) with gradient elution (TFA/acetonitrile). The LC-MS peptide mapping data were processed using BiopharmaLynx software. Identifications were validated manually. The amounts of modifications were estimated from ion counts. Analysis revealed that Asn54 of the heavy chain was extremely susceptible to deamidation. More than 85% of HC Asn54 was deamidated, with ~85% being in the isoAsp form in this sample. Results are summarized in Table 7. The isoAsp at position 54 was also observed in the crystal structure of NI308.5J10 Fab.

TABLE 7

Results for deamidation of Asn residues in NI308.5J10

| Oxidation site | % deamidation |
|---|---|
| LC N33 | 2 |
| HC N54 | 96 |
| HC N391 | 1.7 |
| HC N396 | 0.3 |

Example 13: Design of NI-308.5J10 Variants and Verification of the Mutations

One NI-308.5J10 light chain mutation was selected to remove the light chain glycosylation site (N75D). Four NI-308.5J10 heavy chain mutation were selected to remove the deamidation-prone asparagine (N54S, N54T) or the glycine at position 55(G55S, G55T). Constructs were designed for expression of variants as full human IgG1s. To allow expression of Fabs, constructs containing V$_H$ and CH1 regions of variants with a C-terminal hexahistidine tag (SEQ ID NO: 84) were designed. The sequences are listed in Table 8.

TABLE 8

Amino acid sequences of modified NI-308.5J10 antibody

| SEQ ID NO | Plasmid# | Position modified | Amino acid sequence |
|---|---|---|---|
| 27 | SDD177 | VL-N75D | EIVLTQSPLSLSVTP GEPASISCRSPRSLL HTNGYTYLDWYLQRP GQSPQLLIFLASNRA SGVPDRFSGSGSGTD FTLRISGVEADDVGV YYCMQGLQPSWTFGQ GTKVEIKRTVAAPSV FIFPPSDEQLKSGTA SVVCLLNNFYPREAK VQWKVDNALQSGNSQ ESVTEQDSKDSTYSL SSTLTLSKADYEKHK VYACEVTHQGLSSPV TKSFNRGEC |
| 28 | SDD173 | VH-N54S Full hIgG1 | QVQLQESGPGLVKPS ETLSLTYTVLGGSVS DYYWSCIRQPAGKGL EWIGRTYTSGKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCDKTHTCPPCPAPE LLGGPSVFLFPPKPK DTLMISRTPEVTCVV VDVSHEDPEVKFNWY VDGVEVHNAKTKPRE EQYNSTYRVVSVLTV LHQDWLNGKEYKCKV SNKALPAPIEKTISK AKGQPREPQVYTLPP SRDELTKNQVSLTCL VKGFYPSDIAVEWES NGQPENNYKTTPPVL DSDGSFFLYSKLTVD KSRWQQGNVFSCSVM HEALHNHYTQKSLSL SPG |
| 29 | SDD174 | VH-N54T Full hIgG1 | QVQLQESGPGLVKPS ETLSLTYTVLGGSVS DYYWSCIRQPAGKGL EWIGRTYTTGKTTYT YNPSLESRLSLSIDT SMNQFSLKLTSVTAA DTAVYYCARWGAVTG |

TABLE 8-continued

Amino acid sequences of modified NI-308.5J10 antibody

| SEQ ID NO | Plasmid# | Position modified | Amino acid sequence |
|---|---|---|---|
| | | | DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCDKTHTCPPCPAPE LLGGPSVFLFPPKPK DTLMISRTPEVTCVV VDVSHEDPEVKFNWY VDGVEVHNAKTKPRE EQYNSTYRVVSVLTV LHQDWLNGKEYKCKV SNKALPAPIEKTISK AKGQPREPQVYTLPP SRDELTKNQVSLTCL VKGFYPSDIAVEWES NGQPENNYKTTPPVL DSDGSFFLYSKLTVD KSRWQQGNVFSCSVM HEALHNHYTQKSLSL SPG |
| 30 | SDD175 | VH-G55S Full hIgG1 | QVQLQESGPGLVKPS ETLSLTYTVLGGSVS DYYWSCIRQPAGKGL EWIGRTYTNSKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCDKTHTCPPCPAPE LLGGPSVFLFPPKPK DTLMISRTPEVTCVV VDVSHEDPEVKFNWY VDGVEVHNAKTKPRE EQYNSTYRVVSVLTV LHQDWLNGKEYKCKV SNKALPAPIEKTISK AKGQPREPQVYTLPP SRDELTKNQVSLTCL VKGFYPSDIAVEWES NGQPENNYKTTPPVL DSDGSFFLYSKLTVD KSRWQQGNVFSCSVM HEALHNHYTQKSLSL SPG |
| 31 | SDD176 | VH-G55T Full hIgG1 | QVQLQESGPGLVKPS ETLSLTYTVLGGSVS DYYWSCIRQPAGKGL EWIGRTYTNTKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCDKTHTCPPCPAPE LLGGPSVFLFPPKPK DTLMISRTPEVTCVV VDVSHEDPEVKFNWY VDGVEVHNAKTKPRE EQYNSTYRVVSVLTV LHQDWLNGKEYKCKV SNKALPAPIEKTISK AKGQPREPQVYTLPP SRDELTKNQVSLTCL VKGFYPSDIAVEWES NGQPENNYKTTPPVL DSDGSFFLYSKLTVD KSRWQQGNVFSCSVM HEALHNHYTQKSLSL SPG |
| 32 | SDD178 | WT Fab-his | QVQLQESGPGLVKPS ETLSLTYTVLGGSVS DYYWSCIRQPAGKGL EWIGRTYTNGKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCHHHHHH |
| 33 | SDD179 | VH-N54S Fab-6H | QVQLQESGPGLVKPS ETLSLTYTVLGGSVS DYYWSCIRQPAGKGL EWIGRTYTSGKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCHHHHHH |
| 34 | SDD180 | VH-N54T Fab-6H | QVQLQESGPGLVKPS ETLSLTYTVLGGSVS DYYWSCIRQPAGKGL EWIGRTYTTGKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCHHHHHH |
| 35 | SDD181 | VH-G55S Fab-6H | QVQLQESGPGLVKPS ETLSLTYTVLGGSVS DYYWSCIRQPAGKGL EWIGRTYTNSKTTYT YNPSLESRLSLSIDT SMNQFSLKLTSVTAA |

TABLE 8-continued

Amino acid sequences of modified NI-308.5J10 antibody

| SEQ ID NO | Plasmid# | Position modified | Amino acid sequence |
|---|---|---|---|
| | | | DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCHHHHHH |
| 36 | SDD182 | VH-G55T Fab-6H | QVQLQESGPGLVKPS ETLSLTYTVLGGSVS DYYWSCIRQPAGKGL EWIGRTYTNTKTTYT YNPSLESRLSLSIDT SMNQFSLKLTSVTAA DTAVYYCARWGAVTG DYYYGMDVWGPGTLV TVSSASTKGPSVFPL APSSKSTSGGTAALG CLVKDYFPEPVTVSW NSGALTSGVHTFPAV LQSSGLYSLSSVVTV PSSSLGTQTYICNVN HKPSNTKVDKKVEPK SCHHHHHH |

For verification of the mutations, mass spectrometry analysis of NI-308.5J10 antibody variant N54S/N75D has been performed. Intact mass analysis of 5J10 N54S/N75D hIgG1 showed that the detected major components in the reduced, glycosylated antibody were the predicted light chain and the heavy chain with an N-linked G0F glycan, indicating that the N75D mutation was successful. Deconvoluted mass spectra of reduced, non-deglycosylated NI-308.5J10 N54S/N75D hIgG1. Intact mass analysis of NI-308.5J10 N54S/N75D hIgG1 showed that the detected major components in the reduced, glycosylated antibody were the predicted light chain and the heavy chain with an N-linked G0F glycan, indicating that the N75D mutation was successful.

FIG. 11 shows the crystal structure of the NI-308.5J10 antibody into which the mutations have been mapped. As can be derived from the crystal structure, the post translational modifications are far away from the binding site of the antibody.

Example 14: Production of variant IgG1 and Fabs

Engineered antibody NI-308.5J10 variants consisting of N75D light chain in combination with each of the heavy chain mutants were transiently transfected into CHO-S cells using FectoPro transfection reagent and shifted to reduced temperature 24 h later. Proteins were produced as full human IgG1 and also as a Fabs using the constructs described above. The supernatants were harvested by centrifugation and clarified by passing through 0.45 um filter. The Fabs were then purified by affinity chromatography followed by size exclusion chromatography (Table 9). For purification of full IgG1 proteins, clarified culture medium was loaded onto rProtein A sepharose (GE healthcare). The column was washed with 20 mM $Na_2HPO_4$ pH 7.4, 150 mM NaCl and protein was eluted with 25 mM $NaH_2PO_4$ pH 2.8, 100 mM NaCl, neutralized with 12.5 mM $Na_2HPO_4$ pH 8.6 diluted from a 0.5 M stock solution. For purification of Fabs, clarified culture medium was loaded onto NiExcel sepharose (GE Healthcare), washed with buffer A (25 mM tris pH 8, 500 mM NaCl, 10 mM imidazole) and eluted with buffer A containing 300 mM imidazole. Affinity purified proteins were purified on a Superdex 200 10/300 column in PBS. Purified proteins were analyzed for size and homogeneity by SDS-PAGE. For SDS-PAGE, samples were subjected on 4-20% Tris-glycine gradient gels from Invitrogen. Non-reduced samples were heated at 95° C. for 3 min prior to electrophoresis. Reduced samples were treated with sample buffer containing 100 mM DTT and heated at 95° C. for 3 min prior to electrophoresis. The results of the SDS-PAGE (FIG. 12) revealed that all proteins showed the expected size with no apparent aggregates or proteolysis products.

TABLE 9

Expression of NI-308.5J10 variant IgGs and Fabs

| | | HC | | LC | | | |
|---|---|---|---|---|---|---|---|
| | | Mutation | Plasmid # | Mutation | Plasmid # | 4D # | Titer (mg/l) |
| hIgG1 | | WT | SDD151 | WT | SDD152 | #6003 | 134.5 |
| | | WT | SDD151 | N75D | SDD177 | #6207 | 132.3 |
| | | N54S | SDD173 | N75D | SDD177 | #6208 | 130.1 |
| | | N54T | SDD174 | N75D | SDD177 | #6209 | 122.4 |
| | | G55S | SDD175 | N75D | SDD177 | #6210 | 126.5 |
| | | G55T | SDD176 | N75D | SDD177 | #6211 | 129.3 |
| hIgG1-Fab-6His | | WT-Fab-6His | SDD178 | WT | SDD152 | #6212 | 118.1 |
| | | WT-Fab-6His | SDD178 | N75D | SDD177 | #6213 | 97.8 |
| | | N54S-Fab-6His | SDD179 | N75D | SDD177 | #6214 | 104.1 |
| | | N54T-Fab-6His | SDD180 | N75D | SDD177 | #6215 | 106.1 |
| | | G55S-Fab-6His | SDD181 | N75D | SDD177 | #6216 | 102 |
| | | G55T-Fab-6His | SDD182 | N75D | SDD177 | #6217 | 103 |

Example 15: Binding of proteins to poly-GA by SPR

Variant Fabs were assessed for binding to synthetic poly-GA by SPR, using a Biacore T200 instrument (GE Healthcare). Synthetic biotin-8xGA was captured on a Biotin CAPture chip (GE Healthcare) at 2-4 μg/mm$^2$ from solutions at 5 ng/mL in SPR buffer (10 mM HEPES, pH 7.2, 150 mM NaCl, 3.4 mM EDTA, 0.05% BSA, 0.005% surfactant P20) using reagents and protocols provided by the manufacturer. A series of solutions of variant antibody Fab fragments at increasing concentrations of 1.23, 3.7, 11, 33, and 100 nM in SPR buffer were injected over the biotin-8xGA coated sensor chip for 4 min each at 30 μL/min followed by buffer wash, and the binding response relative to a reference sensor with no biotin-8xGA was recorded during injections and for 15 min after the final injection. Data were analyzed with Biacore T200 Evaluation Software v3.0 using a 1:1 binding model. All NI-308.5J10 variants display similar binding kinetics to synthetic 8×GA with KDs of 20-30 nM. The results of the measurements are listed in Table 10. As the SPR binding profiles of NI-308.5J10 variant Fabs to synthetic 8×GA show all NI-308.5J10 variants display similar binding kinetics to synthetic 8×GA with KDs of 20-30 nM.

TABLE 10

Binding rates and affinity of NI-308.5J10 variants Fabs for 8 × GA measured by SPR.

| | Association rate, $k_a$ (M$^{-1}$s$^{-1}$) | Dissociation rate, $k_d$ (s$^{-1}$) | Affinity, $K_D$ (nM) |
|---|---|---|---|
| 5J10 WT Fab | 2.7 × 10$^5$ | 7.8 × 10$^{-3}$ | 28 |
| LC N75D Fab | 2.3 × 10$^5$ | 5.9 × 10$^{-3}$ | 26 |
| HC N54S/LC N75D Fab | 2.9 × 10$^5$ | 6.0 × 10$^{-3}$ | 21 |
| HC N54T/LC N75D Fab | 2.6 × 10$^5$ | 7.6 × 10$^{-3}$ | 30 |
| HC G55S/LC N75D Fab | 1.8 × 10$^5$ | 4.4 × 10$^{-3}$ | 24 |
| HC G55T/LC N75D Fab | 2.0 × 10$^5$ | 4.4 × 10$^{-3}$ | 22 |

Example 16: Stability of 5J10 Variants

Additional tests of molecular stability were performed on NI-308.5J10 variants. Thermal stability profiles generated by differential scanning calorimetry (VP-DSC, MicroCal) for all variants were similar, with melting temperatures for the CH2 domains (full IgG1s) around 72° C., melting temperatures of Fab in the range of 79–81° C. and the melting temperature of the CH3 domain >86° C. (Table 11).

TABLE 11

Thermal stability of NI-308.5J10 variants. For full IgGs, three main melting transitions observed by DSC at temperatures $T_{m1}$, characterizing unfolding of the hFc CH2 domain, $T_{m2}$, characterizing the unfolding of the Fab (CH1, VH, CL, VL) and $T_{m3}$, characterizing unfolding of the hFc CH3 domain. For 5J10 hIgG1, $T_{m1}$ and $T_{m3}$ could not be determined due to overlap with $T_{m2}$ (*). For Fabs, one melting transition is observed, characterizing the unfolding of the Fab (CH1, VH, CL, VL).

| Molecule | Tm$_1$ CH2 | Tm$_2$ Fab | Tm$_3$ CH3 |
|---|---|---|---|
| 5J10 hIgG1 | * | 80.2 | * |
| 5J10-LC N75D hIgG1 | 72.9 | 80.0 | 87.0 |
| 5J10-LC N75D, HC N54S hIgG1 | 72.6 | 80.6 | 87.2 |
| 5J10-LC N75D, HC N54T hIgG1 | 72.9 | 79.0 | 86.7 |
| 5J10-LC N75D, HC G55S hIgG1 | 72.7 | 79.7 | 86.9 |
| 5J10-LC N75D, HC G55T hIgG1 | 72.5 | 79.8 | 86.9 |
| 5J10 Fab | NA | 80.2 | NA |
| 5J10-LC N75D Fab | NA | 80.2 | NA |
| 5J10-LC N75D, HC N54S Fab | NA | 80.7 | NA |
| 5J10-LC N75D, HC N54T Fab | NA | 79.3 | NA |
| 5J10-LC N75D, HC G55S Fab | NA | 80.2 | NA |
| 5J10-LC N75D, HC G55T Fab | NA | 80.2 | NA |

Example 17: Cell-Based Models for Studying the Pathogenic Mechanisms of C9orf72 DPR Proteins Recent reports in emerging cell culture and animal models provided evidence for the toxicity of aberrant C9orf72 DPR proteins. For example, toxicity for cytoplasmic poly-GA in cell culture systems was reported by May et al. (Acta Neuropathol. 128 (2014), 485-503) and Zhang et al. (Acta Neuropathol. 128 (2014), 505-524).

To determine if, as shown for tau (Yanamandra et al., Ann. Clin. Transl. Neurol. 2 (2013), 278-288) and α-synuclein (Tran et al., Cell Rep. 7 (2014), 2054-2065), spread of DPR pathology can be prevented by treatment with antibodies of the present invention, in vitro C9orf72 DPR toxicity assays are used similar in kind. In particular, synthetic DNA sequences were generated to drive the expression of individual DPR proteins harboring 150 dipeptide repeats in an ATG-dependent translation. A randomized codon strategy was employed to ensure the expression of only the selected individual DPR protein sequence. To drive expression of the DPR proteins in neuronal cells such as SH-SYSY, NSC-34, Neuro-2a, iPSC-derived neurons and primary neurons, the synthetic DNA sequences were cloned into an expression vector regulated by the neuron specific Thy 1.2 promoter. For high-level expression in a wide range of eukaryotic cells such as HEK293T, U-2 OS, HeLa and Cos cells the synthetic DNA sequences were cloned into expression vectors regulated by the CMV promoter. Human iPSC-derived neurons and trans-differentiated neurons (iNeurons) derived from C9orf72 patient fibroblasts represents additional C9orf72 DPR proteins cell culture models.

These cellular models can be used for testing the therapeutic utility of the antibodies of the present invention. Evaluation and confirmation of the therapeutic effects of the antibodies of the present invention can be performed by monitoring cell viability by mitochondrial and/or caspase activity assays, cell toxicity by cytolysis and/or membrane leakage assays, and inhibition of cellular DPR proteins spreading by immunohistochemical assays.

Example 18: Validation of the Therapeutic Utility of Anti-DPR Antibody in Transgenic Mouse Models of C9orf72 Pathology Immunotherapy approaches developed against aggregation-prone and/or misfolded proteins have yielded promising results in preclinical and clinical studies of several neurodegenerative diseases. Validation of the therapeutic utility of the subject anti-DPR antibody in transgenic mouse models of C9orf72 pathology is performed as described in Example 15 of WO 2016/050822 A2. Furthermore, C9orf72 BAC transgenic mouse lines showing pathological hallmarks of C9orf72 disease including RNA foci and dipeptide repeat proteins from RAN translation as well as associated cognitive deficits and a survival phenotype (Liu et al., Neuron 90 (2016), 521-34 and Jiang et al., Neuron 90 (2016), 535-50) have been developed, which are suitable for confirming the therapeutic utility of anti-DPR antibodies. Furthermore, an appropriate transgenic mouse line, the so-called C9-500 BAC transgenic mouse line expressing a human C9orf72 gene with ~500 hexanucleotide repeats is commercially available under FVB/NJ-Tg(C9orf72) 500Lpwr/J from the Jackson Laboratory, 600 Main Street, Bar Harbor, ME USA 04609. Hemizygous mice of this line develop age-dependent paralysis, anxiety-like behavior, decreased survival and widespread neurodegeneration of the brain and spinal cord, accompanied by accumulation of sense/antisense RNA foci and aggregation of RAN protein and TDP43. C9-500 mice allow study of both an acute, rapidly progressive disease as well as a slow progressive disease. Thus, this is a model for studying C9orf72 repeat length-dependent gain-of-toxicity in familial amyotrophic lateral sclerosis (ALS or Lou Gehrig's disease) and frontotemporal dementia (FTD), and therefore a preferred mouse model for confirming the therapeutic utility of the subject antibody.

In addition, further animal models have been developed in the meantime; see, e.g., the *Drosophila* model described in Simone et al. (2018), supra, and the non-human animal model described in international application WO 2018/064600. strategies which translate in vivo data generated from such animal models to the therapy of the corresponding human disease are also known to the person skilled in the art; see, e.g., Picher-Martel et al., Acta Neuropathologica Communications 4 (2016), 1-29. In particular, guidance can be taken from the development of Aducanumab, a recombinant human-derived antibody capable of targeting beta-amyloid (Abeta) in the brain of Alzheimer's disease patients and which so far showed promising results in phase I and II clinical trials. The generation of the lead antibody for Aducanumab and investigation of its biochemical and immunohistochemical properties as well as biological activity in vivo in a mouse model of Alzheimer's disease is described in international application WO 2008/081008, the disclosure content of which is incorporated herein by reference. As illustrated in Example 4 of WO 2008/081008, the anti-Abeta antibody when administered intraperitoneally and weakly with a dose of 3 mg/kg was capable of improving abnormal cognitive behavior and conferred reduction of beta-amyloid plaque load in the transgenic mouse model of Alzheimer's disease. As could be confirmed in clinical trials, the dose and treatment regimen used in that mouse model also proved effective in the clinical trials, where the doses of between 1 and 10 mg/kg including 3 mg/kg had been investigated. Accordingly, transgenic mouse models of diseases caused pathological protein can be well used for the prediction of to the therapeutic utility of a given antibody in human patients.

Regarding the administration mode and dose of the subject antibody and variants thereof, based on investigations of the therapeutic potential of peripheral antibody treatment of transgenic mice overexpressing disease-causing human superoxide dismutase 1 (SOD1) mutants leading to the development of symptoms of amyotrophic lateral sclerosis (ALS), treatment could be shown to be effective following direct brain infusion and also peripheral administration of the anti-SOD1 antibody, in particular when administered weekly per intraperitoneal (i.p.) injections at a dose of 3 to 30 mg/kg; see Maier et al., 2018, Science Translational Medicine. Since poly-GA-DPR containing proteins are translated from the C9orf72 gene similar as misfolded and aggregated SOD1 is present in the brain of patients suffering from ALS, and may even co-aggregate, it is prudent to expect that the subject antibody and variants thereof are effective within the same dosage regimen, i.e. at 3 to 30 mg/kg by weekly i.p. injection. Accordingly, in a preferred embodiment the anti-DPR antibody and DPR-binding fragment thereof are formulated in the pharmaceutical composition is designed to be administered weekly via i.p. injection at a dose of 3 to 30 mg/kg. Accordingly, also in accordance with the present invention weekly i.p. injection of the subject antibody at a dose of 3 to 30 mg/kg is a preferred administration regimen.

Furthermore, because of the evolutionarily optimization and affinity maturation within the human immune system antibodies of the present invention provide a valuable therapeutic tool due to being isolated from healthy human subjects with high probability for excellent safety profile and lack of immunogenicity. Confirmation of these expected therapeutic effects may be provided by test methods as described in the above mentioned publications with human instead of mouse antibodies.

The invention claimed is:

1. An antibody capable of binding a dipeptide repeat (DPR) of poly-glycine-alanine (GA) having at least 6 repeats (GA) 6 (SEQ ID NO: 80) as translated from the chromosome 9 open reading frame 72 (C9orf72) gene, or a DPR-binding fragment thereof, wherein the antibody or DPR-binding fragment thereof comprises in its variable region a variable heavy (VH)-complementarity determining region (CDR) 1, a VH-CDR2, a VH-CDR3, a variable light (VL)-CDR1, a VL-CDR2, and a VL-CDR3, wherein:

(a) the VH-CDR1 comprises the amino acid sequence of SEQ ID NO: 3 or the amino acid sequence of SEQ ID NO:78, the VH-CDR2 comprises the amino acid sequence of SEQ ID NO: 13, the VH-CDR3 comprises the amino acid sequence of SEQ ID NO: 5, the VL-CDR 1 comprises the amino acid sequence of SEQ ID NO: 8, the VL-CDR2 comprises the amino acid sequence of SEQ ID NO: 9, and the VL-CDR3 comprises the amino acid sequence of SEQ ID NO: 10;

(b) the VH-CDR1 comprises the amino acid sequence of SEQ ID NO: 3 or the amino acid sequence of SEQ ID NO:78, the VH-CDR2 comprises the amino acid sequence of SEQ ID NO: 16, the VH-CDR3 comprises the amino acid sequence of SEQ ID NO: 5, the VL-CDR 1 comprises the amino acid sequence of SEQ ID NO: 8, the VL-CDR2 comprises the amino acid sequence of SEQ ID NO: 9, and the VL-CDR3 comprises the amino acid sequence of SEQ ID NO: 10;

(c) the VH-CDR1 comprises the amino acid sequence of SEQ ID NO: 3 or the amino acid sequence of SEQ ID NO:78, the VH-CDR2 comprises the amino acid sequence of SEQ ID NO: 19, the VH-CDR3 comprises the amino acid sequence of SEQ ID NO: 5, the VL-CDR 1 comprises the amino acid sequence of SEQ ID NO: 8, the VL-CDR2 comprises the amino acid sequence of SEQ ID NO: 9, and the VL-CDR3 comprises the amino acid sequence of SEQ ID NO: 10;

(d) the VH-CDR1 comprises the amino acid sequence of SEQ ID NO: 3 or the amino acid sequence of SEQ ID NO:78, the VH-CDR2 comprises the amino acid sequence of SEQ ID NO: 22, the VH-CDR3 comprises the amino acid sequence of SEQ ID NO: 5, the VL-CDR 1 comprises the amino acid sequence of SEQ ID NO: 8, the VL-CDR2 comprises the amino acid sequence of SEQ ID NO: 9, and the VL-CDR3 comprises the amino acid sequence of SEQ ID NO: 10; or (e) the antibody or DPR-binding fragment thereof comprises an amino acid sequence heterologous to the amino acid sequence of SEQ ID NO:2 or heterologous to the amino acid sequence of SEQ ID NO:7, and wherein the VH-CDR1 comprises the amino acid sequence of SEQ ID NO: 3 or the amino acid sequence of SEQ ID NO:78, the VH-CDR2 comprises the amino acid sequence of SEQ ID NO: 4, the VH-CDR3 comprises the amino acid sequence of SEQ ID NO: 5, the VL-CDR1 comprises the amino acid sequence of SEQ ID NO: 8, the VL-CDR2 comprises the amino acid sequence of SEQ ID NO: 9, and the VL-CDR3 comprises the amino acid sequence of SEQ ID NO: 10.

2. The antibody or DPR-binding fragment thereof of claim 1, which is selected from the group consisting of a single chain Fv fragment (scFv), an F(ab') fragment, an F(ab) fragment, and an F(ab')₂ fragment and/or which is a chimeric murine-human or a murinized antibody.

3. The antibody or DPR-binding fragment thereof of claim 1, which is
   (i) detectably labeled with a label selected from the group consisting of an enzyme, a radioisotope, a fluorophore, tag, flag and a heavy metal; or
   (ii) attached to a drug.

4. A pharmaceutical composition comprising the antibody or DPR-binding fragment thereof of claim 1 and a pharmaceutically acceptable carrier.

5. A diagnostic composition or kit comprising the antibody or DPR-binding fragment thereof of claim 1.

6. The antibody or DPR-binding fragment thereof of claim 1, comprising in its variable region a $V_H$ chain and a $V_L$ chain, wherein:
   (i) the $V_H$ chain comprises the amino acid sequence of SEQ ID NO: 2 and the $V_L$ chain comprises the amino acid sequence of SEQ ID NO: 24;
   (iii) the $V_H$ chain comprises the amino acid sequence of SEQ ID NO: 15 and the $V_L$ chain comprises the amino acid sequence of SEQ ID NO: 24;
   (iv) the $V_H$ chain comprises the amino acid sequence of SEQ ID NO: 18 and the $V_L$ chain comprises the amino acid sequence of SEQ ID NO: 24; or
   (v) the $V_H$ chain comprises the amino acid sequence of SEQ ID NO: 21 and the $V_L$ chain comprises the amino acid sequence of SEQ ID NO: 24.

7. A method for in vivo detection of or targeting a therapeutic and/or diagnostic agent to poly-GA DPR proteins in a human subject, the method comprising administering to the human subject the antibody or DPR-binding fragment thereof of claim 3.

8. One or more polynucleotide(s) encoding the antibody or DPR-binding fragment thereof of claim 1 or an immunoglobulin $V_H$ or $V_L$ chain thereof.

9. One or more vector(s) comprising the polynucleotide(s) of claim 8.

10. A host cell comprising the polynucleotide(s) of claim 8.

11. A host cell comprising the vector(s) of claim 9.

12. A method for preparing an anti-DPR antibody or immunoglobulin chain(s) thereof, said method comprising
   (a) culturing the cell of claim 10; and
   (b) isolating the antibody or immunoglobulin chain(s) thereof from the culture.

13. An antibody capable of binding a dipeptide repeat (DPR) of poly-glycine alanine (GA) having at least 6 repeats (GA) 6 (SEQ ID NO: 80) as translated from the chromosome 9 open reading frame 72 (C9orf72) gene, or a DPR-binding fragment thereof, wherein the antibody or DPR-binding fragment thereof comprises in its variable region the following six complementarity determining regions (CDRs):
   (a) a variable heavy (VH)-CDR1 comprising the amino acid sequence of SEQ ID NO: 3,
   (b) a VH-CDR2 comprising the amino acid sequence of SEQ ID NO: 13,
   (c) a VH-CDR3 comprising the amino acid sequence of SEQ ID NO: 5,
   (d) a variable light (VL)-CDR1 comprising the amino acid sequence of SEQ ID NO: 8,
   (e) a VL-CDR2 comprising the amino acid sequence of SEQ ID NO: 9, and
   (f) a VL-CDR3 comprising the amino acid sequence of SEQ ID NO: 10.

14. The antibody or DPR-binding fragment thereof of claim 13, comprising in its variable region a $V_H$ chain comprising the amino acid sequence of SEQ ID NO: 12.

15. The antibody or DPR-binding fragment thereof of claim 13, comprising in its variable region a $V_L$ chain comprising the amino acid sequence of SEQ ID NO: 24.

16. The antibody or DPR-binding fragment thereof of claim 13, comprising in its variable region a $V_H$ chain comprising the amino acid sequence of SEQ ID NO: 12 and a $V_L$ chain comprising the amino acid sequence of SEQ ID NO: 24.

17. A pharmaceutical composition comprising the antibody or DPR-binding fragment thereof of claim 13 and a pharmaceutically acceptable carrier.

18. An antibody capable of binding a dipeptide repeat (DPR) of poly-glycine-alanine (GA) having at least 6 repeats (GA) 6 (SEQ ID NO: 80) as translated from the chromosome 9 open reading frame 72 (C9orf72) gene, or a DPR-binding fragment thereof, wherein the antibody or DPR-binding fragment thereof comprises in its variable region the following six complementarity determining regions (CDRs):
   (a) a variable heavy (VH)-CDR1 comprising the amino acid sequence of SEQ ID NO: 78,
   (b) a VH-CDR2 comprising the amino acid sequence of SEQ ID NO: 13,
   (c) a VH-CDR3 comprising the amino acid sequence of SEQ ID NO: 5,
   (d) a variable light (VL)-CDR1 comprising the amino acid sequence of SEQ ID NO: 8,
   (e) a VL-CDR2 comprising the amino acid sequence of SEQ ID NO: 9, and
   (f) a VL-CDR3 comprising the amino acid sequence of SEQ ID NO: 10.

* * * * *

SEQUENCE LISTING

```
<160> NUMBER OF SEQ ID NOS: 84

<210> SEQ ID NO 1
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION: /note="NI-308.5J10 variable heavy chain (VH)
      sequence"

<400> SEQUENCE: 1 cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15
```

| | | | | | | | | | | | | | | | | |
|---|---|---|---|---|---|---|---|---|---|---|---|---|---|---|---|---|
| acc | ctg | tcc | ctc | act | tac | act | gtc | tta | ggt | ggc | tcc | gtc | agt | gat | tac | 96 |
| Thr | Leu | Ser | Leu | Thr | Tyr | Thr | Val | Leu | Gly | Gly | Ser | Val | Ser | Asp | Tyr | |
| | | | 20 | | | | 25 | | | | | 30 | | | | |
| tac | tgg | agc | tgc | atc | cgg | cag | ccc | gcc | ggg | aag | gga | ctg | gag | tgg | att | 144 |
| Tyr | Trp | Ser | Cys | Ile | Arg | Gln | Pro | Ala | Gly | Lys | Gly | Leu | Glu | Trp | Ile | |
| | | 35 | | | | 40 | | | | | 45 | | | | | |
| ggg | cga | aca | tat | act | aac | ggg | aag | acc | act | tac | act | tac | aac | ccc | tcc | 192 |
| Gly | Arg | Thr | Tyr | Thr | Asn | Gly | Lys | Thr | Thr | Tyr | Thr | Tyr | Asn | Pro | Ser | |
| 50 | | | | | 55 | | | | | 60 | | | | | | |
| ctc | gag | agt | cga | ctc | agt | ttg | tct | ata | gac | acg | tcc | atg | aac | caa | ttc | 240 |
| Leu | Glu | Ser | Arg | Leu | Ser | Leu | Ser | Ile | Asp | Thr | Ser | Met | Asn | Gln | Phe | |
| 65 | | | | | 70 | | | | | 75 | | | | | 80 | |
| tcc | ctg | aag | ttg | acc | tct | gtg | acg | gcc | gcg | gac | acg | gcc | gtc | tat | tac | 288 |
| Ser | Leu | Lys | Leu | Thr | Ser | Val | Thr | Ala | Ala | Asp | Thr | Ala | Val | Tyr | Tyr | |
| | | | | 85 | | | | | 90 | | | | | 95 | | |
| tgc | gcg | aga | tgg | ggg | gcg | gtg | act | ggt | gac | tac | tac | tac | ggt | atg | gac | 336 |
| Cys | Ala | Arg | Trp | Gly | Ala | Val | Thr | Gly | Asp | Tyr | Tyr | Tyr | Gly | Met | Asp | |
| | | | 100 | | | | | 105 | | | | | 110 | | | |
| gtc | tgg | ggc | cca | ggc | acc | ctg | gtc | acc | gtc | tcc | tcg | | | | | 372 |
| Val | Trp | Gly | Pro | Gly | Thr | Leu | Val | Thr | Val | Ser | Ser | | | | | |
| | | | 115 | | | | | 120 | | | | | | | | |

<210> SEQ ID NO 2
<211> LENGTH: 124
<212> TYPE: PRT
<213> ORGANISM: Homo sapiens
<400> SEQUENCE: 2

Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Asn Gly Lys Thr Thr Tyr Thr Tyr Asn Pro Ser
50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
                85                  90                  95

Cys Ala Arg Trp Gly Ala Val Thr Gly Asp Tyr Tyr Tyr Gly Met Asp
            100                 105                 110

Val Trp Gly Pro Gly Thr Leu Val Thr Val Ser Ser
        115                 120

<210> SEQ ID NO 3
<211> LENGTH: 5
<212> TYPE: PRT
<213> ORGANISM: Homo sapiens
<400> SEQUENCE: 3

Asp Tyr Tyr Trp Ser
1               5

<210> SEQ ID NO 4
<211> LENGTH: 18
<212> TYPE: PRT
<213> ORGANISM: Homo sapiens
<400> SEQUENCE: 4

Arg Thr Tyr Thr Asn Gly Lys Thr Thr Tyr Thr Tyr Asn Pro Ser Leu
1               5                   10                  15

Glu Ser

<210> SEQ ID NO 5
<211> LENGTH: 14
<212> TYPE: PRT
<213> ORGANISM: Homo sapiens

<400> SEQUENCE: 5

Trp Gly Ala Val Thr Gly Asp Tyr Tyr Tyr Gly Met Asp Val
1               5                   10

<210> SEQ ID NO 6
<211> LENGTH: 336
<212> TYPE: DNA
<213> ORGANISM: Homo sapiens
<220> FEATURE:
<221> NAME/KEY: CDS
<222> LOCATION: (1)..(336)
<223> OTHER INFORMATION: /note="NI-308.5J10 variable light chain (VK)
      sequence"

<400> SEQUENCE: 6 gaa att gtg ctg act cag tct cca ctc tcc ctg tcc gtc acc cct gga      48
Glu Ile Val Leu Thr Gln Ser Pro Leu Ser Leu Ser Val Thr Pro Gly
1               5                   10                  15 gag ccg gcc tcc atc tcc tgc agg tct cct cgg agc ctt cta cat act      96
Glu Pro Ala Ser Ile Ser Cys Arg Ser Pro Arg Ser Leu Leu His Thr
                20                  25                  30 aat gga tat aca tat ttg gac tgg tac cta caa agg cca ggg cag tct     144
Asn Gly Tyr Thr Tyr Leu Asp Trp Tyr Leu Gln Arg Pro Gly Gln Ser
            35                  40                  45 cca caa ctc ctg atc ttt ttg gct tct aat cgg gcc tcc ggg gtc cct     192
Pro Gln Leu Leu Ile Phe Leu Ala Ser Asn Arg Ala Ser Gly Val Pro
        50                  55                  60 gac agg ttc agt ggc agc gga tca ggc aca aat ttt aca ctg aga atc     240
Asp Arg Phe Ser Gly Ser Gly Ser Gly Thr Asn Phe Thr Leu Arg Ile
65                  70                  75                  80 agc gga gtg gag gct gac gat gtt gga gtt tat tac tgc atg caa ggt     288
Ser Gly Val Glu Ala Asp Asp Val Gly Val Tyr Tyr Cys Met Gln Gly
                85                  90                  95 cta caa cct tcg tgg acg ttc ggc cag ggg acc aag gtg gaa atc aaa     336
Leu Gln Pro Ser Trp Thr Phe Gly Gln Gly Thr Lys Val Glu Ile Lys
            100                 105                 110

<210> SEQ ID NO 7
<211> LENGTH: 112
<212> TYPE: PRT
<213> ORGANISM: Homo sapiens

<400> SEQUENCE: 7

Glu Ile Val Leu Thr Gln Ser Pro Leu Ser Leu Ser Val Thr Pro Gly
1               5                   10                  15

Glu Pro Ala Ser Ile Ser Cys Arg Ser Pro Arg Ser Leu Leu His Thr
                20                  25                  30

Asn Gly Tyr Thr Tyr Leu Asp Trp Tyr Leu Gln Arg Pro Gly Gln Ser
            35                  40                  45

Pro Gln Leu Leu Ile Phe Leu Ala Ser Asn Arg Ala Ser Gly Val Pro
        50                  55                  60

Asp Arg Phe Ser Gly Ser Gly Ser Gly Thr Asn Phe Thr Leu Arg Ile
65                  70                  75                  80

```
Ser Gly Val Glu Ala Asp Asp Val Gly Val Tyr Tyr Cys Met Gln Gly
            85                  90                  95

Leu Gln Pro Ser Trp Thr Phe Gly Gln Gly Thr Lys Val Glu Ile Lys
            100                 105                 110

<210> SEQ ID NO 8
<211> LENGTH: 16
<212> TYPE: PRT
<213> ORGANISM: Homo sapiens

<400> SEQUENCE: 8

Arg Ser Pro Arg Ser Leu Leu His Thr Asn Gly Tyr Thr Tyr Leu Asp
1               5                   10                  15

<210> SEQ ID NO 9
<211> LENGTH: 7
<212> TYPE: PRT
<213> ORGANISM: Homo sapiens

<400> SEQUENCE: 9

Leu Ala Ser Asn Arg Ala Ser
1               5

<210> SEQ ID NO 10
<211> LENGTH: 9
<212> TYPE: PRT
<213> ORGANISM: Homo sapiens

<400> SEQUENCE: 10

Met Gln Gly Leu Gln Pro Ser Trp Thr
1               5

<210> SEQ ID NO 11
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(372)
<223> OTHER INFORMATION: /note="NI-308.5J10 variable heavy chain (VH)
      sequence - N54S mutation"

<400> SEQUENCE: 11 cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc act tac act gtc tta ggt ggc tcc gtc agt gat tac      96
Thr Leu Ser Leu Thr Tyr Thr Val Leu Gly Gly Ser Val Ser Asp Tyr
            20                  25                  30 tac tgg agc tgc atc cgg cag ccc gcc ggg aag gga ctg gag tgg att     144
Tyr Trp Ser Cys Ile Arg Gln Pro Ala Gly Lys Gly Leu Glu Trp Ile
        35                  40                  45 ggg cga aca tat act agc ggg aag acc act tac act tac aac ccc tcc     192
Gly Arg Thr Tyr Thr Ser Gly Lys Thr Thr Tyr Thr Tyr Asn Pro Ser
    50                  55                  60 ctc gag agt cga ctc agt ttg tct ata gac acg tcc atg aac caa ttc     240
Leu Glu Ser Arg Leu Ser Leu Ser Ile Asp Thr Ser Met Asn Gln Phe
65                  70                  75                  80 tcc ctg aag ttg acc tct gtg acg gcc gcg gac acg gcc gtc tat tac     288
Ser Leu Lys Leu Thr Ser Val Thr Ala Ala Asp Thr Ala Val Tyr Tyr
```

```
                        85                  90                  95
tgc gcg aga tgg ggg gcg gtg act ggt gac tac tac tac ggt atg gac        336
Cys Ala Arg Trp Gly Ala Val Thr Gly Asp Tyr Tyr Tyr Gly Met Asp
                100                 105                 110 gtc tgg ggc cca ggc acc ctg gtc acc gtc tcc tcg                        372
Val Trp Gly Pro Gly Thr Leu Val Thr Val Ser Ser
        115                 120
```

<210> SEQ ID NO 12
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Ser Gly Lys Thr Thr Tyr Thr Tyr Asn Pro Ser
    50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
                85                  90                  95

Cys Ala Arg Trp Gly Ala Val Thr Gly Asp Tyr Tyr Tyr Gly Met Asp
                100                 105                 110

Val Trp Gly Pro Gly Thr Leu Val Thr Val Ser Ser
        115                 120
```

<210> SEQ ID NO 13
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="NI-308.5J10 VH-CDR2 sequence - N54S mutation"

<400> SEQUENCE: 13

```
Arg Thr Tyr Thr Ser Gly Lys Thr Thr Tyr Thr Tyr Asn Pro Ser Leu
1               5                   10                  15

Glu Ser
```

<210> SEQ ID NO 14
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: CDS
<222> LOCATION: (1)..(372)

<223> OTHER INFORMATION: /note="NI-308.5J10 variable heavy chain (VH)
sequence - N54T Mutation"

<400> SEQUENCE: 14

```
cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc act tac act gtc tta ggt ggc tcc gtc agt gat tac      96
Thr Leu Ser Leu Thr Tyr Thr Val Leu Gly Gly Ser Val Ser Asp Tyr
                20                  25                  30 tac tgg agc tgc atc cgg cag ccc gcc ggg aag gga ctg gag tgg att     144
Tyr Trp Ser Cys Ile Arg Gln Pro Ala Gly Lys Gly Leu Glu Trp Ile
            35                  40                  45 ggg cga aca tat act acc ggg aag acc act tac act tac aac ccc tcc     192
Gly Arg Thr Tyr Thr Thr Gly Lys Thr Thr Tyr Thr Tyr Asn Pro Ser
        50                  55                  60 ctc gag agt cga ctc agt ttg tct ata gac acg tcc atg aac caa ttc     240
Leu Glu Ser Arg Leu Ser Leu Ser Ile Asp Thr Ser Met Asn Gln Phe
65                  70                  75                  80 tcc ctg aag ttg acc tct gtg acg gcc gcg gac acg gcc gtc tat tac     288
Ser Leu Lys Leu Thr Ser Val Thr Ala Ala Asp Thr Ala Val Tyr Tyr
                85                  90                  95 tgc gcg aga tgg ggg gcg gtg act ggt gac tac tac tac ggt atg gac     336
Cys Ala Arg Trp Gly Ala Val Thr Gly Asp Tyr Tyr Tyr Gly Met Asp
                100                 105                 110 gtc tgg ggc cca ggc acc ctg gtc acc gtc tcc tcg                     372
Val Trp Gly Pro Gly Thr Leu Val Thr Val Ser Ser
            115                 120
```

<210> SEQ ID NO 15
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 15

```
Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
                20                  25                  30

Tyr Trp Ser Cys Ile Arg Gln Pro Ala Gly Lys Gly Leu Glu Trp Ile
            35                  40                  45

Gly Arg Thr Tyr Thr Thr Gly Lys Thr Thr Tyr Thr Tyr Asn Pro Ser
        50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
                85                  90                  95

Cys Ala Arg Trp Gly Ala Val Thr Gly Asp Tyr Tyr Tyr Gly Met Asp
                100                 105                 110

Val Trp Gly Pro Gly Thr Leu Val Thr Val Ser Ser
            115                 120
```

<210> SEQ ID NO 16
<211> LENGTH: 18
<212> TYPE: PRT
<213> ORGANISM: Artificial Sequence
<220> FEATURE:

<210> SEQ ID NO 16 (continued)
<221> NAME/KEY: source
<223> OTHER INFORMATION: /note="Description of Artificial Sequence:
     Synthetic peptide"
<220> FEATURE:
<221> NAME/KEY: source
<223> OTHER INFORMATION: /note="NI-308.5J10 VH-CDR2 sequence - N54T
     mutation"

<400> SEQUENCE: 16

Arg Thr Tyr Thr Thr Gly Lys Thr Thr Tyr Thr Tyr Asn Pro Ser Leu
1               5                   10                  15

Glu Ser

<210> SEQ ID NO 17
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"
<220> FEATURE:
<221> NAME/KEY: CDS
<222> LOCATION: (1)..(372)
<223> OTHER INFORMATION: /note="NI-308.5J10 variable heavy chain (VH)
     sequence - G55S Mutation"

<400> SEQUENCE: 17 cag gtg cag ctg cag gag tcg ggc cca gga ctg gtg aag cct tcg gag        48
Gln Val Gln Leu Gln Glu Ser Gly Pro Gly Leu Val Lys Pro Ser Glu
1               5                   10                  15 acc ctg tcc ctc act tac act gtc tta ggt ggc tcc gtc agt gat tac        96
Thr Leu Ser Leu Thr Tyr Thr Val Leu Gly Gly Ser Val Ser Asp Tyr
            20                  25                  30 tac tgg agc tgc atc cgg cag ccc gcc ggg aag gga ctg gag tgg att       144
Tyr Trp Ser Cys Ile Arg Gln Pro Ala Gly Lys Gly Leu Glu Trp Ile
        35                  40                  45 ggg cga aca tat act aac agc aag acc act tac act tac aac ccc tcc       192
Gly Arg Thr Tyr Thr Asn Ser Lys Thr Thr Tyr Thr Tyr Asn Pro Ser
    50                  55                  60 ctc gag agt cga ctc agt ttg tct ata gac acg tcc atg aac caa ttc       240
Leu Glu Ser Arg Leu Ser Leu Ser Ile Asp Thr Ser Met Asn Gln Phe
65                  70                  75                  80 tcc ctg aag ttg acc tct gtg acg gcc gcg gac acg gcc gtc tat tac       288
Ser Leu Lys Leu Thr Ser Val Thr Ala Ala Asp Thr Ala Val Tyr Tyr
                85                  90                  95 tgc gcg aga tgg ggg gcg gtg act ggt gac tac tac tac ggt atg gac       336
Cys Ala Arg Trp Gly Ala Val Thr Gly Asp Tyr Tyr Tyr Gly Met Asp
            100                 105                 110 gtc tgg ggc cca ggc acc ctg gtc acc gtc tcc tcg                       372
Val Trp Gly Pro Gly Thr Leu Val Thr Val Ser Ser
        115                 120

<210> SEQ ID NO 18
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 18

Gln Val Gln Leu Gln Glu Ser Gly Pro Gly Leu Val Lys Pro Ser Glu
1               5                   10                  15

```
Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Asn Ser Lys Thr Thr Tyr Thr Tyr Asn Pro Ser
    50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
                85                  90                  95

Cys Ala Arg Trp Gly Ala Val Thr Gly Asp Tyr Tyr Tyr Gly Met Asp
            100                 105                 110

Val Trp Gly Pro Gly Thr Leu Val Thr Val Ser Ser
        115                 120
```

<210> SEQ ID NO 19
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: source
<223> OTHER INFORMATION: /note="NI-308.5J10 VH-CDR2 sequence - G55S
    mutation"

<400> SEQUENCE: 19

```
Arg Thr Tyr Thr Asn Ser Lys Thr Thr Tyr Thr Tyr Asn Pro Ser Leu
1               5                   10                  15

Glu Ser
```

<210> SEQ ID NO 20
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"
<220> FEATURE:
<221> NAME/KEY: CDS
<222> LOCATION: (1)..(372)
<223> OTHER INFORMATION: /note="NI-308.5J10 variable heavy chain (VH)
    sequence - G55T Mutation"

<400> SEQUENCE: 20

```
cag gtg cag ctg cag gag tcg ggc cca gga ctg gtg aag cct tcg gag        48
Gln Val Gln Leu Gln Glu Ser Gly Pro Gly Leu Val Lys Pro Ser Glu
1               5                   10                  15 acc ctg tcc ctc act tac act gtc tta ggt ggc tcc gtc agt gat tac        96
Thr Leu Ser Leu Thr Tyr Thr Val Leu Gly Gly Ser Val Ser Asp Tyr
            20                  25                  30 tac tgg agc tgc atc cgg cag ccc gcc ggg aag gga ctg gag tgg att       144
Tyr Trp Ser Cys Ile Arg Gln Pro Ala Gly Lys Gly Leu Glu Trp Ile
        35                  40                  45 ggg cga aca tat act aac acc aag acc act tac act tac aac ccc tcc       192
Gly Arg Thr Tyr Thr Asn Thr Lys Thr Thr Tyr Thr Tyr Asn Pro Ser
    50                  55                  60 ctc gag agt cga ctc agt ttg tct ata gac acg tcc atg aac caa ttc       240
Leu Glu Ser Arg Leu Ser Leu Ser Ile Asp Thr Ser Met Asn Gln Phe
65                  70                  75                  80
```

```
tcc ctg aag ttg acc tct gtg acg gcc gcg gac acg gcc gtc tat tac    288
Ser Leu Lys Leu Thr Ser Val Thr Ala Ala Asp Thr Ala Val Tyr Tyr
            85                  90                  95 tgc gcg aga tgg ggg gcg gtg act ggt gac tac tac tac ggt atg gac    336
Cys Ala Arg Trp Gly Ala Val Thr Gly Asp Tyr Tyr Tyr Gly Met Asp
            100                 105                 110 gtc tgg ggc cca ggc acc ctg gtc acc gtc tcc tcg                    372
Val Trp Gly Pro Gly Thr Leu Val Thr Val Ser Ser
            115                 120

<210> SEQ ID NO 21
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
                20                  25                  30

Tyr Trp Ser Cys Ile Arg Gln Pro Ala Gly Lys Gly Leu Glu Trp Ile
            35                  40                  45

Gly Arg Thr Tyr Thr Asn Thr Lys Thr Thr Tyr Thr Tyr Asn Pro Ser
50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
                85                  90                  95

Cys Ala Arg Trp Gly Ala Val Thr Gly Asp Tyr Tyr Tyr Gly Met Asp
            100                 105                 110

Val Trp Gly Pro Gly Thr Leu Val Thr Val Ser Ser
            115                 120

<210> SEQ ID NO 22
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="NI-308.5J10 VH-CDR2 sequence - G55T
      mutation"

<400> SEQUENCE: 22

Arg Thr Tyr Thr Asn Thr Lys Thr Thr Tyr Thr Tyr Asn Pro Ser Leu
1               5                   10                  15

Glu Ser

<210> SEQ ID NO 23
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
```

```
<221> NAME/KEY: CDS
<222> LOCATION: (1)..(336)
<223> OTHER INFORMATION: /note="NI-308.5J10 variable light chain (VK)
      sequence - N75D Mutation"

<400> SEQUENCE: 23 gaa att gtg ctg act cag tct cca ctc tcc ctg tcc gtc acc cct gga      48
Glu Ile Val Leu Thr Gln Ser Pro Leu Ser Leu Ser Val Thr Pro Gly
1               5                   10                  15 gag ccg gcc tcc atc tcc tgc agg tct cct cgg agc ctt cta cat act      96
Glu Pro Ala Ser Ile Ser Cys Arg Ser Pro Arg Ser Leu Leu His Thr
            20                  25                  30 aat gga tat aca tat ttg gac tgg tac cta caa agg cca ggg cag tct     144
Asn Gly Tyr Thr Tyr Leu Asp Trp Tyr Leu Gln Arg Pro Gly Gln Ser
        35                  40                  45 cca caa ctc ctg atc ttt ttg gct tct aat cgg gcc tcc ggg gtc cct     192
Pro Gln Leu Leu Ile Phe Leu Ala Ser Asn Arg Ala Ser Gly Val Pro
    50                  55                  60 gac agg ttc agt ggc agc gga tca ggc aca gac ttt aca ctg aga atc     240
Asp Arg Phe Ser Gly Ser Gly Ser Gly Thr Asp Phe Thr Leu Arg Ile
65                  70                  75                  80 agc gga gtg gag gct gac gat gtt gga gtt tat tac tgc atg caa ggt     288
Ser Gly Val Glu Ala Asp Asp Val Gly Val Tyr Tyr Cys Met Gln Gly
                85                  90                  95 cta caa cct tcg tgg acg ttc ggc cag ggg acc aag gtg gaa atc aaa     336
Leu Gln Pro Ser Trp Thr Phe Gly Gln Gly Thr Lys Val Glu Ile Lys
            100                 105                 110

<210> SEQ ID NO 24
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Glu Ile Val Leu Thr Gln Ser Pro Leu Ser Leu Ser Val Thr Pro Gly
1               5                   10                  15

Glu Pro Ala Ser Ile Ser Cys Arg Ser Pro Arg Ser Leu Leu His Thr
            20                  25                  30

Asn Gly Tyr Thr Tyr Leu Asp Trp Tyr Leu Gln Arg Pro Gly Gln Ser
        35                  40                  45

Pro Gln Leu Leu Ile Phe Leu Ala Ser Asn Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Gly Val Glu Ala Asp Asp Val Gly Val Tyr Tyr Cys Met Gln Gly
                85                  90                  95

Leu Gln Pro Ser Trp Thr Phe Gly Gln Gly Thr Lys Val Glu Ile Lys
            100                 105                 110

<210> SEQ ID NO 25
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
```

<223> OTHER INFORMATION: /note="NI-308.5J10 variable light chain (VK) plasmid (SDD 152)"

<400> SEQUENCE: 25

Glu Ile Val Leu Thr Gln Ser Pro Leu Ser Leu Ser Val Thr Pro Gly
1               5                   10                  15

Glu Pro Ala Ser Ile Ser Cys Arg Ser Pro Arg Ser Leu Leu His Thr
            20                  25                  30

Asn Gly Tyr Thr Tyr Leu Asp Trp Tyr Leu Gln Arg Pro Gly Gln Ser
        35                  40                  45

Pro Gln Leu Leu Ile Phe Leu Ala Ser Asn Arg Ala Ser Gly Val Pro
    50                  55                  60

Asp Arg Phe Ser Gly Ser Gly Ser Gly Thr Asn Phe Thr Leu Arg Ile
65                  70                  75                  80

Ser Gly Val Glu Ala Asp Asp Val Gly Val Tyr Tyr Cys Met Gln Gly
                85                  90                  95

Leu Gln Pro Ser Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 26
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="NI-308.5J10-hIgG1 variable heavy chain (VH) plasmid (SDD 151)"

<400> SEQUENCE: 26

Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Asn Gly Lys Thr Thr Tyr Tyr Asn Pro Ser
    50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr

```
                85                  90                  95
Cys Ala Arg Trp Gly Ala Val Thr Gly Asp Tyr Tyr Tyr Gly Met Asp
            100                 105                 110

Val Trp Gly Pro Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 27
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                             Synthetic polypeptide"
<220> FEATURE:
<221> NAME/KEY: source
<223> OTHER INFORMATION: /note="NI-308.5J10 variable light chain (VK)
      plasmid (SDD 177) - N75D mutation"

<400> SEQUENCE: 27

Glu Ile Val Leu Thr Gln Ser Pro Leu Ser Leu Ser Val Thr Pro Gly
1               5                   10                  15

Glu Pro Ala Ser Ile Ser Cys Arg Ser Pro Arg Ser Leu Leu His Thr
            20                  25                  30

Asn Gly Tyr Thr Tyr Leu Asp Trp Tyr Leu Gln Arg Pro Gly Gln Ser
        35                  40                  45

Pro Gln Leu Leu Ile Phe Leu Ala Ser Asn Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Gly Val Glu Ala Asp Asp Val Gly Val Tyr Tyr Cys Met Gln Gly
                85                  90                  95

Leu Gln Pro Ser Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 28
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="NI-308.5J10-hIgG1 variable heavy chain
      (VH) plasmid (SDD 173) - N54S mutation"

<400> SEQUENCE: 28

Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Ser Gly Lys Thr Thr Tyr Thr Tyr Asn Pro Ser
    50                  55                  60

Leu Glu Ser Arg Leu Ser Leu Ser Ile Asp Thr Ser Met Asn Gln Phe
```

-continued

```
                65                  70                  75                  80
        Ser Leu Lys Leu Thr Ser Val Thr Ala Ala Asp Thr Ala Val Tyr Tyr
                        85                  90                  95

Cys Ala Arg Trp Gly Ala Val Thr Gly Asp Tyr Tyr Gly Met Asp
                    100                 105                 110

Val Trp Gly Pro Gly Thr Leu Val Thr Val Ser Ser Ala Ser Thr Lys
                    115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
        145                 150                 155                 160

Val Thr Val Ser Trp Asn Ser Gly Ala Leu Thr Ser Gly Val His Thr
                        165                 170                 175

Phe Pro Ala Val Leu Gln Ser Ser Gly Leu Tyr Ser Leu Ser Ser Val
                    180                 185                 190

Val Thr Val Pro Ser Ser Ser Leu Gly Thr Gln Thr Tyr Ile Cys Asn
                    195                 200                 205

Val Asn His Lys Pro Ser Asn Thr Lys Val Asp Lys Lys Val Glu Pro
            210                 215                 220

Lys Ser Cys Asp Lys Thr His Thr Cys Pro Pro Cys Pro Ala Pro Glu
        225                 230                 235                 240

Leu Leu Gly Gly Pro Ser Val Phe Leu Phe Pro Pro Lys Pro Lys Asp
                        245                 250                 255

Thr Leu Met Ile Ser Arg Thr Pro Glu Val Thr Cys Val Val Val Asp
                    260                 265                 270

Val Ser His Glu Asp Pro Glu Val Lys Phe Asn Trp Tyr Val Asp Gly
                    275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
        305                 310                 315                 320

Leu Asn Gly Lys Glu Tyr Lys Cys Lys Val Ser Asn Lys Ala Leu Pro
                        325                 330                 335

Ala Pro Ile Glu Lys Thr Ile Ser Lys Ala Lys Gly Gln Pro Arg Glu
                    340                 345                 350

Pro Gln Val Tyr Thr Leu Pro Pro Ser Arg Asp Glu Leu Thr Lys Asn
                    355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
        385                 390                 395                 400

Thr Pro Pro Val Leu Asp Ser Asp Gly Ser Phe Phe Leu Tyr Ser Lys
                        405                 410                 415

Leu Thr Val Asp Lys Ser Arg Trp Gln Gln Gly Asn Val Phe Ser Cys
                    420                 425                 430

Ser Val Met His Glu Ala Leu His Asn His Tyr Thr Gln Lys Ser Leu
                    435                 440                 445

Ser Leu Ser Pro Gly
            450

<210> SEQ ID NO 29
<211> LENGTH: 453
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="NI-308.5J10-hIgG1 variable heavy chain (VH) plasmid (SDD 174) - N54T mutation"

<400> SEQUENCE: 29

```
Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Thr Gly Lys Thr Thr Tyr Thr Tyr Asn Pro Ser
50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
                85                  90                  95

Cys Ala Arg Trp Gly Ala Val Thr Gly Asp Tyr Tyr Gly Met Asp
            100                 105                 110

Val Trp Gly Pro Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365
```

```
Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 30
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="NI-308.5J10-hIgG1 variable heavy chain
      (VH) plasmid (SDD 175) - G55S mutation"

<400> SEQUENCE: 30

Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Asn Ser Lys Thr Thr Tyr Thr Tyr Asn Pro Ser
    50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
            85                  90                  95

Cys Ala Arg Trp Gly Ala Val Thr Gly Asp Tyr Tyr Gly Met Asp
        100                 105                 110

Val Trp Gly Pro Gly Thr Leu Val Thr Val Ser Ser Ala Ser Thr Lys
    115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Leu Gly Thr Gln Thr Tyr Ile Cys Asn
    195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240
```

```
Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 31
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="NI-308.5J10-hIgG1 variable heavy chain
      (VH) plasmid (SDD 176) - G55T mutation"

<400> SEQUENCE: 31

Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Asn Thr Lys Thr Thr Tyr Tyr Asn Pro Ser
    50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
                85                  90                  95

Cys Ala Arg Trp Gly Ala Val Thr Gly Asp Tyr Tyr Tyr Gly Met Asp
            100                 105                 110
```

Val Trp Gly Pro Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 32
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: source
<223> OTHER INFORMATION: /note="NI-308.5J10-Fab-6His variable heavy chain (VH) plasmid (SDD 178)"

<400> SEQUENCE: 32

Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Asn Gly Lys Thr Thr Tyr Thr Tyr Asn Pro Ser
    50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
                85                  90                  95

Cys Ala Arg Trp Gly Ala Val Thr Gly Asp Tyr Tyr Tyr Gly Met Asp
            100                 105                 110

Val Trp Gly Pro Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys His His His His His His
225                 230

<210> SEQ ID NO 33
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note=" NI-308.5J10-Fab-6His variable heavy
      chain (VH) plasmid (SDD 179) - N54S mutation"

<400> SEQUENCE: 33

Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Ser Gly Lys Thr Thr Tyr Thr Tyr Asn Pro Ser
    50                  55                  60

Leu Glu Ser Arg Leu Ser Leu Ser Ile Asp Thr Ser Met Asn Gln Phe
65                  70                  75                  80

```
Ser Leu Lys Leu Thr Ser Val Thr Ala Ala Asp Thr Ala Val Tyr Tyr
            85                  90                  95

Cys Ala Arg Trp Gly Ala Val Thr Gly Asp Tyr Tyr Gly Met Asp
            100                 105                 110

Val Trp Gly Pro Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
            210                 215                 220

Lys Ser Cys His His His His His His
225                 230
```

<210> SEQ ID NO 34
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="NI-308.5J10-Fab-6His variable heavy chain (VH) plasmid (SDD 180) - N54T mutation"

<400> SEQUENCE: 34

```
Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
            35                  40                  45

Gly Arg Thr Tyr Thr Thr Gly Lys Thr Thr Tyr Thr Tyr Asn Pro Ser
50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
            85                  90                  95

Cys Ala Arg Trp Gly Ala Val Thr Gly Asp Tyr Tyr Gly Met Asp
            100                 105                 110

Val Trp Gly Pro Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175
```

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
            210                 215                 220

Lys Ser Cys His His His His His His
225                 230

<210> SEQ ID NO 35
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="NI-308.5J10-Fab-6His variable heavy
      chain (VH) plasmid (SDD 181) - G55S mutation"

<400> SEQUENCE: 35

Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
            35                  40                  45

Gly Arg Thr Tyr Thr Asn Ser Lys Thr Thr Tyr Thr Tyr Asn Pro Ser
50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
            85                  90                  95

Cys Ala Arg Trp Gly Ala Val Thr Gly Asp Tyr Tyr Tyr Gly Met Asp
            100                 105                 110

Val Trp Gly Pro Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
            210                 215                 220

Lys Ser Cys His His His His His His
225                 230

<210> SEQ ID NO 36
<211> LENGTH: 233
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="NI-308.5J10-Fab-6His variable heavy
      chain (VH) plasmid (SDD 182) - G55T mutation"

<400> SEQUENCE: 36

Gln Val Gln Leu Gln Glu Ser Gly Pro Gly Leu Val Lys Pro Ser Glu
1               5                   10                  15

Thr Leu Ser Leu Thr Tyr Thr Val Leu Gly Gly Ser Val Ser Asp Tyr
            20                  25                  30

Tyr Trp Ser Cys Ile Arg Gln Pro Ala Gly Lys Gly Leu Glu Trp Ile
        35                  40                  45

Gly Arg Thr Tyr Thr Asn Thr Lys Thr Thr Tyr Thr Tyr Asn Pro Ser
    50                  55                  60

Leu Glu Ser Arg Leu Ser Leu Ser Ile Asp Thr Ser Met Asn Gln Phe
65                  70                  75                  80

Ser Leu Lys Leu Thr Ser Val Thr Ala Ala Asp Thr Ala Val Tyr Tyr
                85                  90                  95

Cys Ala Arg Trp Gly Ala Val Thr Gly Asp Tyr Tyr Gly Met Asp
            100                 105                 110

Val Trp Gly Pro Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys His His His His His His
225                 230

<210> SEQ ID NO 37
<211> LENGTH: 471
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Met Gly Trp Ser Leu Ile Leu Leu Phe Leu Val Ala Val Ala Thr Arg
1               5                   10                  15

Val Leu Ser Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
        35                  40                  45

Ser Asn His Ala Met His Trp Val Arg Gln Ala Pro Gly Lys Gly Leu
    50                  55                  60
```

Glu Trp Val Ala Val Ile Ser Tyr Asp Gly Glu Asn Thr Tyr Tyr Ala
65                  70                  75                  80

Asp Ser Ile Glu Gly Arg Phe Thr Ile Ser Arg Asp Asn Phe Lys Asn
            85                  90                  95

Thr Leu Phe Leu Gln Met Tyr Ser Leu Thr Ala Asp Asp Thr Ala Met
        100                 105                 110

Tyr Phe Cys Ala Arg Gly Gly Arg Arg Gly His Phe Thr Ser Tyr Tyr
        115                 120                 125

Leu Asp Tyr Trp Gly Gln Gly Thr Leu Val Thr Val Ser Ser Ala Ser
        130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
            245                 250                 255

Pro Glu Leu Leu Gly Gly Pro Ser Val Phe Leu Phe Pro Pro Lys Pro
        260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
        340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
        370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
        420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly
465                 470

```
<210> SEQ ID NO 38
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Asn His
            20                  25                  30

Ala Met His Trp Val Arg Gln Ala Pro Gly Lys Gly Leu Glu Trp Val
        35                  40                  45

Ala Val Ile Ser Tyr Asp Gly Glu Asn Thr Tyr Tyr Ala Asp Ser Ile
    50                  55                  60

Glu Gly Arg Phe Thr Ile Ser Arg Asp Asn Phe Lys Asn Thr Leu Phe
65                  70                  75                  80

Leu Gln Met Tyr Ser Leu Thr Ala Asp Asp Thr Ala Met Tyr Phe Cys
                85                  90                  95

Ala Arg Gly Gly Arg Arg Gly His Phe Thr Ser Tyr Tyr Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
```

```
                355                 360                 365
Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly
        450

<210> SEQ ID NO 39
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 40
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn His
            20                  25                  30

Ala Met His Trp Val Arg Gln Ala Pro Gly Lys Gly Leu Glu Trp Val
        35                  40                  45

Ala Val Ile Ser Tyr Asp Gly Glu Asn Thr Tyr Tyr Ala Asp Ser Ile
    50                  55                  60

Glu Gly Arg Phe Thr Ile Ser Arg Asp Asn Phe Lys Asn Thr Leu Phe
65                  70                  75                  80

Leu Gln Met Tyr Ser Leu Thr Ala Asp Thr Ala Met Tyr Phe Cys
                85                  90                  95

Ala Arg Gly Gly Arg Arg Gly His Phe Thr Ser Tyr Tyr Leu Asp Tyr
            100                 105                 110

Trp Gly Gln Gly Thr Leu Val Thr Val Ser Ser
            115                 120
```

<210> SEQ ID NO 41
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

```
Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asn Ile Asp Lys Tyr Leu Asn Trp Tyr Gln Gln Ile Pro Gly Lys
    50                  55                  60

Ala Pro Lys Leu Leu Ile Tyr Ala Ala Ser Ser Leu His Ser Gly Val
65                  70                  75                  80
```

```
Pro Ser Arg Phe Ser Gly Ser Gly Thr Asp Phe Ser Leu Thr
            85                  90                  95

Ile Ser Ser Leu Gln Pro Glu Asp Phe Ala Ile Tyr Tyr Cys Gln Gln
        100                 105                 110

Ser Tyr Ser Ser Phe Arg Thr Phe Gly Gln Gly Thr Lys Leu Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 42
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Lys Tyr
            20                  25                  30

Leu Asn Trp Tyr Gln Gln Ile Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Ile Tyr Tyr Cys Gln Gln Ser Tyr Ser Ser Phe Arg
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

Phe Asn Arg Gly Glu Cys
            210

<210> SEQ ID NO 43
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 44
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Lys Tyr
            20                  25                  30

Leu Asn Trp Tyr Gln Gln Ile Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Ile Tyr Tyr Cys Gln Gln Ser Tyr Ser Ser Phe Arg
                85                  90                  95

Thr Phe Gly Gln Gly Thr Lys Leu Glu Ile Lys
            100                 105

<210> SEQ ID NO 45
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:

```
           Synthetic peptide"

<400> SEQUENCE: 45

Gly Phe Thr Phe Ser Asn His Ala Met His
1               5                   10

<210> SEQ ID NO 46
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 46

Val Ile Ser Tyr Asp Gly Glu Asn Thr Tyr Tyr Ala Asp Ser Ile Glu
1               5                   10                  15

Gly

<210> SEQ ID NO 47
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 47

Gly Gly Arg Arg Gly His Phe Thr Ser Tyr Tyr Leu Asp Tyr
1               5                   10

<210> SEQ ID NO 48
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 48

Arg Ala Ser Gln Asn Ile Asp Lys Tyr Leu Asn
1               5                   10

<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 49

Ala Ala Ser Ser Leu His Ser
1               5

<210> SEQ ID NO 50
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"
```

<400> SEQUENCE: 50

Gln Gln Ser Tyr Ser Ser Phe Arg Thr
1               5

<210> SEQ ID NO 51
<211> LENGTH: 1416
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51

```
atgggttgga gcctcatctt gctgtttctt gtcgctgttg ctacgcgtgt cctgtcgcag      60
gtgcagctgg tggagtctgg gggaggcgta gtccagcctg gaggtccct  gagactgtcc    120
tgtgcagcct ctggattcac cttcagtaat catgctatgc actgggtccg ccaggctcca    180
ggcaaggggc tggagtgggt ggcagttata tcatatgatg gcgagaacac atattatgca    240
gactccattg agggccgatt caccatttcc agagacaatt caagaacac  actctttcta    300
caaatgtaca gcctgacagc tgatgacacg gctatgtact tctgtgcgag agggggccgt    360
cggggggcact tcacctcata ctaccttgac tactggggcc agggaaccct ggtcaccgtc    420
tcctcggcta gtaccaaggg cccatcggtc ttccccctgg cacctcctc  caagagcacc    480
tctgggggca gcggccctg  ggctgcctg  gtcaaggact acttccccga acccgtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa gactcacaca tgcccaccgt gcccagcacc tgaactcctg    780
gggggaccgt cagtcttcct cttccccca  aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat   1020
ggcaaggagt acaagtgcaa ggtttccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga caactacaa  gaccacgcct   1260
cccgtgttgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaaa aaagcctctc cctgtctccc ggttga                             1416
```

<210> SEQ ID NO 52
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52

```
caggtgcagc tggtggagtc tggggggaggc gtagtccagc ctggggaggtc cctgagactg      60
```

| | |
|---|---|
| tcctgtgcag cctctggatt caccttcagt aatcatgcta tgcactgggt ccgccaggct | 120 |
| ccaggcaagg ggctggagtg ggtggcagtt atatcatatg atggcgagaa cacatattat | 180 |
| gcagactcca ttgagggccg attcaccatt tccagagaca atttcaagaa cacactcttt | 240 |
| ctacaaatgt acagcctgac agctgatgac acggctatgt acttctgtgc gagagggggc | 300 |
| cgtcggggc acttcaccct atactacctt gactactggg gccagggaac cctggtcacc | 360 |
| gtctcctcgg ctagtaccaa gggcccatcg gtcttccccc tggcaccctc ctccaagagc | 420 |
| acctctgggg gcacagcggc cctgggctgc ctggtcaagg actacttccc cgaacccgtg | 480 |
| acggtgtcgt ggaactcagg cgccctgacc agcggcgtgc acaccttccc ggctgtccta | 540 |
| cagtcctcag gactctactc cctcagcagc gtggtgaccg tgccctccag cagcttgggc | 600 |
| acccagacct acatctgcaa cgtgaatcac aagcccagca acaccaaggt ggacaagaaa | 660 |
| gttgagccca aatcttgtga caagactcac acatgcccac cgtgcccagc acctgaactc | 720 |
| ctggggggac cgtcagtctt cctcttcccc ccaaaaccca aggacaccct catgatctcc | 780 |
| cggacccctg aggtcacatg cgtggtggtg gacgtgagcc acgaagaccc tgaggtcaag | 840 |
| ttcaactggt acgtggacgg cgtggaggtg cataatgcca agacaaagcc gcggaggag | 900 |
| cagtacaaca gcacgtaccg tgtggtcagc gtcctcaccg tcctgcacca ggactggctg | 960 |
| aatggcaagg agtacaagtg caaggtttcc aacaaagccc tcccagcccc catcgagaaa | 1020 |
| accatctcca aagccaaagg gcagcccga gaaccacagg tgtacaccct gcccccatcc | 1080 |
| cgggatgagc tgaccaagaa ccaggtcagc ctgacctgcc tggtcaaagg cttctatccc | 1140 |
| agcgacatcg ccgtggagtg ggagagcaat gggcagccgg agaacaacta caagaccacg | 1200 |
| cctcccgtgt ggactccga cggctccttc ttcctctaca gcaagctcac cgtggacaag | 1260 |
| agcaggtggc agcaggggaa cgtcttctca tgctccgtga tgcatgaggc tctgcacaac | 1320 |
| cactacacgc aaaaaagcct ctccctgtct cccggttga | 1359 |

<210> SEQ ID NO 53
<211> LENGTH: 990
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53

| | |
|---|---|
| gctagtacca agggcccatc ggtcttcccc ctggcaccct cctccaagag cacctctggg | 60 |
| ggcacagcgg ccctgggctg cctggtcaag gactacttcc ccgaacccgt gacggtgtcg | 120 |
| tggaactcag cgccctgac cagcggcgtg cacaccttcc cggctgtcct acagtcctca | 180 |
| ggactctact ccctcagcag cgtggtgacc gtgccctcca gcagcttggg cacccagacc | 240 |
| tacatctgca acgtgaatca caagcccagc aacaccaagg tggacaagaa agttgagccc | 300 |
| aaatcttgtg acaagactca cacatgccca ccgtgcccag cacctgaact cctgggggga | 360 |
| ccgtcagtct tcctcttccc cccaaaaccc aaggacaccc tcatgatctc ccggacccct | 420 |
| gaggtcacat gcgtggtggt ggacgtgagc cacgaagacc ctgaggtcaa gttcaactgg | 480 |
| tacgtggacg gcgtggaggt gcataatgcc aagacaaagc cgcggaggga gcagtacaac | 540 |
| agcacgtacc gtgtggtcag cgtcctcacc gtcctgcacc aggactggct gaatggcaag | 600 |
| gagtacaagt gcaaggtttc caacaaagcc ctcccagccc catcgagaa aaccatctcc | 660 |
| aaagccaaag ggcagccccg agaaccacag gtgtacaccc tgcccccatc ccgggatgag | 720 |

```
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ttggactccg acggctcctt cttcctctac agcaagctca ccgtggacaa gagcaggtgg    900
cagcagggga acgtcttctc atgctccgtg atgcatgagg ctctgcacaa ccactacacg    960
caaaaaagcc tctccctgtc tcccggttga                                    990
```

<210> SEQ ID NO 54
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54

```
caggtgcagc tggtggagtc tgggggaggc gtagtccagc ctgggaggtc cctgagactg     60
tcctgtgcag cctctggatt caccttcagt aatcatgcta tgcactgggt ccgccaggct    120
ccaggcaagg ggctggagtg ggtggcagtt atatcatatg atggcgagaa cacatattat    180
gcagactcca ttgagggccg attcaccatt tccagagaca atttcaagaa cacactcttt    240
ctacaaatgt acagcctgac agctgatgac acggctatgt acttctgtgc gagaggggc    300 cgtcggggc acttcacctc atactacctt gactactggg gccagggaac cctggtcacc    360
gtctcctcg                                                           369
```

<210> SEQ ID NO 55
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55

```
atggacatgc gggtgcccgc ccagctgctg ggcctgctgc tgctgtggtt ccccggctct     60
agatgcgaca tccagatgac ccagtctcca tcctccctgt ctgcatctgt aggagacaga    120
gtcaccatca cttgccgggc aagccagaac atagacaagt acttaaattg gtatcagcag    180
ataccgggga aagcccctaa gctcctgatc tatgctgcat cgagtttgca cagtggggtc    240
ccatcaaggt tcagtggcag tggatctggg acagatttct ctctcaccat cagcagtctg    300
caacctgaag attttgcaat ttactactgt caacagagtt acagttcctt ccggacgttc    360
ggccaaggga ccaagctgga gatcaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gttcgcccgt cacaaagagc ttcaacaggg gagagtgttg a             711
```

<210> SEQ ID NO 56
<211> LENGTH: 645
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic polynucleotide"

<400> SEQUENCE: 56

```
gacatccaga tgacccagtc tccatcctcc ctgtctgcat ctgtaggaga cagagtcacc    60
atcacttgcc gggcaagcca gaacatagac aagtacttaa attggtatca gcagataccg   120
gggaaagccc ctaagctcct gatctatgct gcatcgagtt tgcacagtgg ggtcccatca   180
aggttcagtg gcagtggatc tgggacagat ttctctctca ccatcagcag tctgcaacct   240
gaagattttg caatttacta ctgtcaacag agttacagtt ccttccggac gttcggccaa   300
gggaccaagc tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagttcgc ccgtcacaaa gagcttcaac aggggagagt gttga                  645
```

<210> SEQ ID NO 57
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57

```
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagttcgcc cgtcacaaag   300
agcttcaaca ggggagagtg ttga                                          324
```

<210> SEQ ID NO 58
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58

```
gacatccaga tgacccagtc tccatcctcc ctgtctgcat ctgtaggaga cagagtcacc    60
atcacttgcc gggcaagcca gaacatagac aagtacttaa attggtatca gcagataccg   120
gggaaagccc ctaagctcct gatctatgct gcatcgagtt tgcacagtgg ggtcccatca   180
aggttcagtg gcagtggatc tgggacagat ttctctctca ccatcagcag tctgcaacct   240
gaagattttg caatttacta ctgtcaacag agttacagtt ccttccggac gttcggccaa   300
gggaccaagc tggagatcaa a                                             321
```

<210> SEQ ID NO 59
<211> LENGTH: 19

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Met Gly Trp Ser Leu Ile Leu Leu Phe Leu Val Ala Val Ala Thr Arg
1               5                   10                  15

Val Leu Ser

<210> SEQ ID NO 60
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Met Asp Met Arg Val Pro Ala Gln Leu Leu Gly Leu Leu Leu Leu Trp
1               5                   10                  15

Phe Pro Gly Ser Arg Cys
            20

<210> SEQ ID NO 61
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein (GA)15"

<400> SEQUENCE: 61

Cys His His His His His His Gly Ala Gly Ala Gly Ala Gly Ala Gly
1               5                   10                  15

Ala Gly Ala Gly Ala Gly Ala Gly Ala Gly Ala Gly Ala Gly Ala Gly
            20                  25                  30

Ala Gly Ala Gly Ala
        35

<210> SEQ ID NO 62
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein (GP)15"

<400> SEQUENCE: 62

Cys Gly Pro Gly Pro Gly Pro Gly Pro Gly Pro Gly Pro Gly Pro Gly
1               5                   10                  15

Pro Gly Pro Gly Pro Gly Pro Gly Pro Gly Pro Gly Pro Gly Pro
            20                  25                  30

<210> SEQ ID NO 63
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic dipeptide repeat protein (GR)15"

<400> SEQUENCE: 63

Cys Gly Arg Gly Arg Gly Arg Gly Arg Gly Arg Gly Arg Gly Arg Gly
1               5                   10                  15

Arg Gly Arg Gly Arg Gly Arg Gly Arg Gly Arg Gly Arg Gly Arg
            20                  25                  30

<210> SEQ ID NO 64
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic dipeptide repeat protein (PA)15"

<400> SEQUENCE: 64

Cys Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala
            20                  25                  30

<210> SEQ ID NO 65
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic dipeptide repeat protein (PR)15"

<400> SEQUENCE: 65

Cys Pro Arg Pro Arg Pro Arg Pro Arg Pro Arg Pro Arg Pro Arg Pro
1               5                   10                  15

Arg Pro Arg Pro Arg Pro Arg Pro Arg Pro Arg Pro Arg
            20                  25                  30

<210> SEQ ID NO 66
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic dipeptide repeat protein peptide GA"

<400> SEQUENCE: 66

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala
            20                  25                  30

<210> SEQ ID NO 67
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic dipeptide repeat protein peptide GP"

<400> SEQUENCE: 67

Gly Pro Gly Pro Gly Pro Gly Pro Gly Pro Gly Pro Gly Pro Gly Pro
1               5                   10                  15

```
Gly Pro Gly Pro Gly Pro Gly Pro Gly Pro Gly Pro
            20                  25                  30

<210> SEQ ID NO 68
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein peptide GR"

<400> SEQUENCE: 68

Gly Arg Gly Arg Gly Arg Gly Arg Gly Arg Gly Arg Gly Arg Gly Arg
1               5                   10                  15

Gly Arg Gly Arg Gly Arg Gly Arg Gly Arg Gly Arg Gly Arg
            20                  25                  30

<210> SEQ ID NO 69
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein peptide PA"

<400> SEQUENCE: 69

Pro Ala Pro Ala Pro Ala Pro Ala Pro Ala Pro Ala Pro Ala Pro Ala
1               5                   10                  15

Pro Ala Pro Ala Pro Ala Pro Ala Pro Ala Pro Ala Pro Ala
            20                  25                  30

<210> SEQ ID NO 70
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein peptide PR"

<400> SEQUENCE: 70

Pro Arg Pro Arg Pro Arg Pro Arg Pro Arg Pro Arg Pro Arg Pro Arg
1               5                   10                  15

Pro Arg Pro Arg Pro Arg Pro Arg Pro Arg Pro Arg Pro Arg
            20                  25                  30

<210> SEQ ID NO 71
<211> LENGTH: 46
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein (GA)20"

<400> SEQUENCE: 71

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Gly Ala Gly Ala Gly Ala His His His His His His
        35                  40                  45
```

```
<210> SEQ ID NO 72
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein (GA)10"

<400> SEQUENCE: 72

Gly Ala Gly Ala Gly Ala Gly Ala Gly Ala Gly Ala Gly Ala Gly Ala
1               5                   10                  15

Gly Ala Gly Ala His His His His His His
            20                  25

<210> SEQ ID NO 73
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein (GA)6"

<400> SEQUENCE: 73

Gly Ala Gly Ala Gly Ala Gly Ala Gly Ala Gly Ala His His His His
1               5                   10                  15

His His

<210> SEQ ID NO 74
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein (GA)5"

<400> SEQUENCE: 74

Gly Ala Gly Ala Gly Ala Gly Ala Gly Ala His His His His His His
1               5                   10                  15

<210> SEQ ID NO 75
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein (GA)4"

<400> SEQUENCE: 75

Gly Ala Gly Ala Gly Ala Gly Ala His His His His His His
1               5                   10

<210> SEQ ID NO 76
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein (GA)3"

<400> SEQUENCE: 76

Gly Ala Gly Ala Gly Ala His His His His His His
1               5                   10
```

```
<210> SEQ ID NO 77
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic dipeptide repeat protein (GA)2"

<400> SEQUENCE: 77

Gly Ala Gly Ala His His His His His His
1               5                   10

<210> SEQ ID NO 78
<211> LENGTH: 10
<212> TYPE: PRT
<213> ORGANISM: Homo sapiens

<400> SEQUENCE: 78

Gly Gly Ser Val Ser Asp Tyr Tyr Trp Ser
1               5                   10

<210> SEQ ID NO 79
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gly Ala Gly Ala Gly Ala Gly Ala Gly Ala Gly Ala Gly Ala Gly Ala
1               5                   10                  15

Gly Ala Gly Ala
            20

<210> SEQ ID NO 80
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gly Ala Gly Ala Gly Ala Gly Ala Gly Ala Gly Ala
1               5                   10

<210> SEQ ID NO 81
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Gly Ala Gly Ala Gly Ala Gly Ala Gly Ala Gly Ala Gly Ala Gly Ala
1               5                   10                  15

<210> SEQ ID NO 82
<211> LENGTH: 40
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 82

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Gly Ala Gly Ala Gly Ala
        35                  40

<210> SEQ ID NO 83
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(30)
<223> OTHER INFORMATION: /note="This sequence may encompass 6-15
      "Gly Ala" repeating units"

<400> SEQUENCE: 83

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala
            20                  25                  30

<210> SEQ ID NO 84
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 84

His His His His His His
1               5
```